(12) United States Patent
Nadir et al.

(10) Patent No.: US 9,366,684 B2
(45) Date of Patent: Jun. 14, 2016

(54) METHODS AND KITS FOR ASSESSING HEPARANASE PROCOAGULANT ACTIVITY, COMPOSITIONS COMPRISING HEPARANASE, AND METHODS FOR THE TREATMENT OF COAGULATION RELATED DISORDERS

(75) Inventors: Yona Nadir, Zichron Yaakovv (IL); Benjamin Brenner, Haifa (IL); Israel Vlodavsky, Haifa (IL)

(73) Assignee: RAMBAM MED-TECH, Haifa (IL)

( * ) Notice: Subject to any disclaimer, the term of this patent is extended or adjusted under 35 U.S.C. 154(b) by 0 days.

(21) Appl. No.: 13/980,530

(22) PCT Filed: Jan. 18, 2012

(86) PCT No.: PCT/IL2012/000027
§ 371 (c)(1),
(2), (4) Date: Sep. 10, 2013

(87) PCT Pub. No.: WO2012/098542
PCT Pub. Date: Jul. 26, 2012

(65) Prior Publication Data
US 2014/0140977 A1    May 22, 2014

Related U.S. Application Data

(60) Provisional application No. 61/433,529, filed on Jan. 18, 2011, provisional application No. 61/511,939, filed on Oct. 27, 2011.

(51) Int. Cl.
| | | |
|---|---|---|
| *G01N 33/86* | (2006.01) | |
| *C07K 14/81* | (2006.01) | |
| *C07K 14/745* | (2006.01) | |
| *A61K 38/10* | (2006.01) | |
| *A61K 38/08* | (2006.01) | |
| *A61K 38/36* | (2006.01) | |
| *A61K 38/55* | (2006.01) | |
| *A61K 31/727* | (2006.01) | |
| *A61K 45/06* | (2006.01) | |
| *A61K 38/47* | (2006.01) | |
| *A61K 31/5377* | (2006.01) | |
| *A61K 38/51* | (2006.01) | |

(52) U.S. Cl.
CPC ............ *G01N 33/86* (2013.01); *A61K 31/5377* (2013.01); *A61K 31/727* (2013.01); *A61K 38/08* (2013.01); *A61K 38/10* (2013.01); *A61K 38/36* (2013.01); *A61K 38/47* (2013.01); *A61K 38/51* (2013.01); *A61K 38/55* (2013.01); *A61K 45/06* (2013.01); *C07K 14/745* (2013.01); *C07K 14/8114* (2013.01); *C12Y 302/01166* (2013.01)

(58) Field of Classification Search
None
See application file for complete search history.

(56) References Cited

U.S. PATENT DOCUMENTS

| 5,696,088 A | * | 12/1997 | Innis .................. C07K 14/8114 |
|---|---|---|---|
| | | | 435/69.6 |
| 2001/0029034 A1 | | 10/2001 | Gentz et al. |
| 2009/0099087 A1 | | 4/2009 | Kisiel et al. |
| 2011/0104140 A1 | | 5/2011 | Vlodavsky et al. |

FOREIGN PATENT DOCUMENTS

WO    9504158 A1    2/1995

OTHER PUBLICATIONS

Christiansen, S.C. et al. 2005. Thrombophilia, clinical factors, and recurrent venous thrombotic events. Journal of the American Medical Association. 293(19):2352-2361. specif. pp. 2352, 2353.*
Rawden, H.C. et al. 2000. Relative contribution of cytochromes P-450 and flavin-containing monoxygenases to the metabolism of albendazole by human liver microsomes. Journal of Clincal Pharmacology 49:313-322. specif. pp. 313, 320.*
Huang, K-S. et al. 2004. High-throughput methods for measuring heparanase activity and screening potential antimetastatic and anti-inflammatory agents. Analytical Biochemistry 333: 389-398.*
Axelman et al., (2014) Novel peptides that inhibit heparanase activation of the coagulation system. Thromb Haemost 112(3): 466-77.
Udagawa et al., (2002) Subcellular localization of PP5/TFPI-2 in human placenta: a possible role of PP5/TFPI-2 as an anti-coagulant on the surface of syncytiotrophoblasts. Placenta 23(2-3): 145-153.
Van den Hoven et al., (2006) Increased expression of heparanase in overt diabetic nephropathy. Kidney Int 70(12): 2100-2108.
Vlodavsky and Friedmann (2001) Molecular properties and involvement of heparanase in cancer metastasis and angiogenesis. J Clin Invest 108(3): 341-347.
Vlodavsky et al., (1992) Expression of heparanase by platelets and circulating cells of the immune system: possible involvement in diapedesis and extravasation. Invasion Metastasis 12(2): 112-127.
Vlodavsky et al., (1999) Mammalian heparanase: gene cloning, expression and function in tumor progression and metastasis. Nat Med 5(7): 793-802.
Vlodavsky et al., (2007) Heparanase, heparin and the coagulation system in cancer progression. Thromb Res 120 (Suppl 2): S112-S120.
Walker et al., (1997) Changes in activated protein C resistance during normal pregnancy. Am J Obstet Gynecol 177(1): 162-169.
Wang et al., (2010) Genome-wide association study of esophageal squamous cell carcinoma in Chinese subjects identifies susceptibility loci at PLCE1 and C20orf54. Nat Genet 42(9): 759-763.
Wijnhoven et al., (2008) Heparanase induces a differential loss of heparan sulphate domains in overt diabetic nephropathy. Diabetologia 51(2): 372-382.

(Continued)

*Primary Examiner* — Renee Claytor
*Assistant Examiner* — Sharon M Papciak
(74) *Attorney, Agent, or Firm* — The Roy Gross Law Firm, LLC; Roy Gross

(57) ABSTRACT

The present invention relates to methods and kits for determining heparanase procoagulant activity in a biological sample. The invention also relates to diagnostic methods for the detection and/or monitoring of a coagulation-related pathologic disorder in a mammalian subject. The invention further relates to compositions comprising heparanase and at least one tissue factor, uses and methods based thereon in the treatment, amelioration and prevention of coagulation-related pathologic conditions. The invention still further relates to methods for screening a coagulation modulatory compound, methods and uses based thereon in the treatment, amelioration and prevention of coagulation-related pathologic conditions.

10 Claims, 30 Drawing Sheets

(56) References Cited

OTHER PUBLICATIONS

Xiong et al., (2010) Changes of plasma and placental tissue factor pathway inhibitor-2 in women with preeclampsia and normal pregnancy. Thromb Res 125(6): e317-322.
Zetser et al., (2003) Heparanase affects adhesive and tumorigenic potential of human glioma cells. Cancer Res 63(22): 7733-7741.
Zetser et al., (2004) Processing and activation of latent heparanase occurs in lysosomes. J Cell Sci 117(Pt 11): 2249-2258.
Zetser et al., (2006) Heparanase induces vascular endothelial growth factor expression: correlation with p38 phosphorylation levels and Src activation. Cancer Res 66(3): 1455-1463.
Baker et al., (2012) Heparanase Regulates Thrombosis in Vascular Injury and Stent-Induced Flow Disturbance. J Am Coll Cardiol 59(17): 1551-1560.
Ben-Zaken et al., (2007) Heparanase induces Akt phosphorylation via a lipid raft receptor. Biochem Biophys Res Commun 361(4): 829-834.
Boer et al., (2007) Tissue factor-dependent blood coagulation is enhanced following delivery irrespective of the mode of delivery. J Thromb Haemost 5(12): 2415-2420.
Brill et al., (2004) Differential role of platelet granular mediators in angiogenesis. Cardiovasc Res 63(2): 226-235.
Camera et al., (1999) Cooperation between VEGF and TNF-alpha is necessary for exposure of active tissue factor on the surface of human endothelial cells. Arterioscler Thromb Vasc Biol 19(3): 531-537.
Cofrancesco et al., (1996) Markers of hemostatic system activation during thromboprophylaxis with recombinant hirudin in total hip replacement. Thromb Haemost 75(3): 407-411.
Craig et al., (1989) Transient kinetics of heparin-catalyzed protease inactivation by antithrombin III. Characterization of assembly, product formation, and heparin dissociation steps in the factor Xa reaction. J Biol Chem 264(10): 5452-5461.
Dahl et al., (1995) Increased activation of coagulation and formation of late deep venous thrombosis following discontinuation of thromboprophylaxis after hip replacement surgery. Thromb Res 80(4): 299-306.
Dempsey et al., (2000) Heparanase expression in invasive trophoblasts and acute vascular damage. Glycobiology 10(5): 467-475.
El-Assal et al., (2001) The clinicopathological significance of heparanase and basic fibroblast growth factor expressions in hepatocellular carcinoma. Clin Cancer Res 7(5): 1299-1305.
Freeman and Parish (1998) Human platelet heparanase: purification, characterization and catalytic activity. Biochem J 330( Pt 3): 1341-1350.
Geerts et al., (2008) Prevention of venous thromboembolism: American College of Chest Physicians Evidence-Based Clinical Practice Guidelines (8th Edition). Chest 133(6 Suppl): 381S-453S.
Gingis-Velitski et al., (2004) Heparanase induces endothelial cell migration via protein kinase B/Akt activation. J Biol Chem 279(22): 23536-23541.
Gingis-Velitski et al., (2004) Heparanase uptake is mediated by cell membrane heparan sulfate proteoglycans. J Biol Chem 279(42): 44084-44092.
Gohji et al., (2001) Expression of three extracellular matrix degradative enzymes in bladder cancer. Int J Cancer 95(5): 295-301.
Goldshmidt et al., (2003) Heparanase mediates cell adhesion independent of its enzymatic activity. FASEB J 17(9): 1015-1025.
Haimov-Kochman et al., (2002) Localization of heparanase in normal and pathological human placenta. Mol Hum Reprod 8(6): 566-573.
Hulett et al., (2000) Identification of Active-Site Residues of the Pro-Metastatic Endoglycosidase Heparanase. Biochemistry 39(51): 15659-15667.
Kelly et al., (2003) High heparanase activity in multiple myeloma is associated with elevated microvessel density. Cancer Res 63(24): 8749-8756.
Kim et al., (2000) Changes of plasma tissue factor and tissue factor pathway inhibitor antigen levels and induction of tissue factor expression on the monocytes in coronary artery disease. Cardiology 93(1-2): 31-36.

Lanir et al., (2003) Procoagulant and anticoagulant mechanisms in human placenta. Semin Thromb Hemost 29(2): 175-184.
Li et al., (2008) Dramatic regulation of heparanase activity and angiogenesis gene expression in synovium from patients with rheumatoid arthritis. Arthritis Rheum 58(6): 1590-1600.
Lopez et al., (1997) Hemostatic markers in surgery: a different fibrinolyfic activity may be of pathophysiological significance in orthopedic versus abdominal surgery. Int J Clin Lab Res 27(2-4): 233-237.
Mahieu et al., (2007) Haemostatic changes and acquired activated protein C resistance in normal pregnancy. Blood Coagul Fibrinolysis 18(7): 685-688.
Mandal et al., (2006) Cellular localization and trafficking of tissue factor. Blood 107(12): 4746-4753.
Mannucci (2001) How I treat patients with von Willebrand disease. Blood 97(7): 1915-1919.
Maxhimer et al., (2005) Heparanase-1 gene expression and regulation by high glucose in renal epithelial cells: a potential role in the pathogenesis of proteinuria in diabetic patients. Diabetes 54(7): 2172-2178.
McKenzie et al., (2003) Biochemical characterization of the active heterodimer form of human heparanase (Hpa1) protein expressed in insect cells. Biochemical J 373(Pt 2): 423-435.
Myler and West (2002) Heparanase and platelet factor-4 induce smooth muscle cell proliferation and migration via bFGF release from the ECM. J Biochem 131(6): 913-922.
Nadir and Brenner (2012) Heparanase—A Link between Coagulation, Angiogenesis, and Cancer. Rambam Maimonides Med J 3(1): e0002, pp. 1-9.
Nadir et al., (2006) Heparanase induces tissue factor expression in vascular endothelial and cancer cells. J Thromb Haemost 4(11): 2443-2451.
Nadir et al., (2008) Heparanase induces tissue factor pathway inhibitor expression and extracellular accumulation in endothelial and tumor cells. Thromb Haemost 99(1): 133-141.
Nadir et al., (2010) Heparanase enhances the generation of activated factor X in the presence of tissue factor and activated factor VII. Haematologica 95(11): 1927-1934.
Nadir et al., (2010) Involvement of heparanase in vaginal and cesarean section deliveries. Thromb Res 126(6): e444-e450.
Nadir et al., (2011) An assay to evaluate heparanase procoagulant activity. Thromb Res 128(4): e3-e8.
Ostrovsky et al., (2007) Association of heparanase gene (HPSE) single nucleotide polymorphisms with hematological malignancies. Leukemia 21(11): 2296-2303.
Ostrovsky et al., (2007) Characterization of HPSE gene single nucleotide polymorphisms in Jewish populations of Israel. Acta Haematol 117(1): 57-64.
Ostrovsky et al., (2010) Genetic variations in the heparanase gene (HPSE) associate with increased risk of GVHD following allogeneic stem cell transplantation: effect of discrepancy between recipients and donors. Blood 115(11): 2319-2328.
Ralph et al., (2007) Heparanase gene haplotype (CGC) is associated with stage of disease in patients with ovarian carcinoma. Cancer Sci 98(6): 844-849.
Rohloff et al., (2002) Heparanase expression is a prognostic indicator for postoperative survival in pancreatic adenocarcinoma. Br J Cancer 86(8): 1270-1275.
Samama and Gerotziafas (2003) Evaluation of the pharmacological properties and clinical results of the synthetic pentasaccharide (fondaparinux). Thromb Res 109(1): 1-11.
Schecter et al., (1997) Tissue factor expression in human arterial smooth muscle cells. TF is present in three cellular pools after growth factor stimulation. J Clin Invest 100(9): 2276-2285.
Shafat et al., (2006) An ELISA method for the detection and quantification of human heparanase. Biochem Biophys Res Commun 341(4): 958-963.
Shafat et al., (2006) Characterization of mechanisms involved in secretion of active heparanase. J Biol Chem 281(33): 23804-23811.
Shafat et al., (2007) Heparanase levels are elevated in the plasma of pediatric cancer patients and correlate with response to anticancer treatment. Neoplasia 9(11): 909-916.

(56) References Cited

OTHER PUBLICATIONS

Shafat et al., (2011) Heparanase levels are elevated in the urine and plasma of type 2 diabetes patients and associate with blood glucose levels. PLoS One 6(2): e17312; pp. 1-8.

Steffel et al., (2005) Histamine induces tissue factor expression: implications for acute coronary syndromes. Circulation 112(3): 341·349.

Szecsi et al., (2010) Haemostatic reference intervals in pregnancy. Thromb Haemost 103(4): 718-727.

Tang et al., (2002) Heparanase: a key enzyme in invasion and metastasis of gastric carcinoma. Mod Pathol 15(6): 593-598.

Toyoshima and Nakajima (1999) Human heparanase. Purification, characterization, cloning, and expression. J Biol Chem 274(34): 24153-24160.

\* cited by examiner

TF + heparanase activity:
TF / Heparanase + VIIa + X + chromogenic substrate to Xa = Xa level

TF activity:
TF / Heparanase +heparin + VIIa + X + chromogenic substrate to Xa = Xa level (TF + heparanase activity) − (TF activity) = heparanase procoagulant activity

Fig. 8

Table 1

| | CS (n=10) | Vaginal (n=16) | IUGR (n=9) | Control (n=20) |
|---|---|---|---|---|
| Age | 34 ± 5.2 (25–40) | 31.3 ± 5.6 (25–40) | 31.4 ± 3.1 (26–35) | 33 ± 4.2 (25–40) |
| Birth weight | 3340 ± 456*** (2595–3985) | 2090 ± 252 (1650–2475) | 3370 ± 440*** (2605–3925) | N/A |
| Birth week | 38.4 ± 0.4* (38–40) | 36.6 ± 3.2 (36–40) | 39.3 ± 0.6* (38.3–42) | N/A |
| Blood pressure (mean) | 80 ± 12.7 (59–98) | 93 ± 12.8 (70–110) | 85 ± 12.2 (60–107) | 90 ± 13.1# (75–105) |

Student T-test for independent samples was applied. Values are reported as mean ± SD and range.
*p<0.05 compared to IUGR group, ***p<0.0005 compared to IUGR group. # Blood pressure was measured in 12 controls.

Fig. 11

Table 2

| | Hepa ELISA (pg/ml) | TF + Hepa (absorbance 405-490 nm) | TF (absorbance 405-490 nm) | Hepa (absorbance 405-490 nm) | Hepa relative contribution (%) |
|---|---|---|---|---|---|
| All pregnant/ | 334 ± 113 | 0.53 ± 0.29 | 0.2 ± 0.08 | 0.33 ± 0.26 | 60 ± 3 |
| Non-pregnant | 346 ± 105 | 0.17 ± 0.08** | 0.12 ± 0.04* | 0.05 ± 0.03** | 31 ± 5*** |
| CS/ | 272 ± 91 | 0.8 ± 0.34 | 0.24 ± 0.11 | 0.56 ± 0.32 | 65 ± 6 |
| Non-pregnant | 346 ± 105* | 0.17 ± 0.08*** | 0.12 ± 0.04** | 0.05 ± 0.03*** | 31 ± 5*** |
| Vaginal/ | 380 ± 124 | 0.4 ± 0.14 | 0.15 ± 0.06 | 0.24 ± 0.1 | 60 ± 4 |
| Non-pregnant | 346 ± 105 | 0.17 ± 0.08*** | 0.12 ± 0.04 | 0.05 ± 0.03*** | 31 ± 5*** |
| IUGR/ | 328 ± 116 | 0.4 ± 0.15 | 0.2 ± 0.07 | 0.23 ± 0.09 | 58 ± 3 |
| Non-pregnant | 346 ± 105 | 0.17 ± 0.08*** | 0.12 ± 0.04*** | 0.05 ± 0.03*** | 31 ± 5*** |

Hepa – heparanase. All pregnant (n = 35), non-pregnant (n = 20), CS (n = 10), vaginal (n = 16), IUGR (n = 9). Each of the 55 samples was tested in duplicates in all assays and the mean of two results is presented. *p<0.05, p<0.005, *p<0.0001.

Fig. 12

Table 3

| | Xa (absorbance 405–490 nm) | Thrombin (absorbance 405–490 nm) | Free TFPI (ng/ml) | Antithrombin activity (%) |
|---|---|---|---|---|
| All pregnant/ | 0.34 ± 0.09 | 0.4 ± 0.1 | 6 ± 2 | 94 ± 2.2 |
| Non-pregnant | 0.22 ± 0.2** | 0.26 ± 0.2** | 6.9 ± 1.5 | 99 ± 2.4 |
| CS/ | 0.33 ± 0.08 | 0.4 ± 0.1 | 6.5 ± 1.8 | 98 ± 3.9 |
| Non-pregnant | 0.22 ± 0.2** | 0.26 ± 0.2** | 6.9 ± 1.5 | 99 ± 2.4 |
| Vaginal/ | 0.34 ± 0.1 | 0.43 ± 0.03 | 6 ± 1.4 | 93 ± 3.5 |
| Non-pregnant | 0.22 ± 0.2** | 0.26 ± 0.2** | 6.9 ± 1.5 | 99 ± 2.4 |
| IUGR/ | 0.41 ± 0.03 | 0.4 ± 0.02 | 5.7 ± 2.2 | 91 ± 4.3 |
| Non-pregnant | 0.22 ± 0.2** | 0.26 ± 0.2** | 6.9 ± 1.5 | 99 ± 2.4 |

All pregnant (n = 35), non-pregnant (n = 20), CS (n = 10), vaginal (n = 16), IUGR (n = 9). Each of the 55 samples was tested in duplicates in all assays and the mean of two results is presented. **$p < 0.005$.

Fig. 13

Table 4

| | |
|---|---|
| Age | 66.3 ± 14.6 |
| Gender | 30 females |
| | 20 males |
| Type of surgery | 31 hip |
| | 19 knee |
| Trauma | 15, all hip |
| Osteoarthrosis | 35 |
| Active cancer | 1, breast |
| Thrombotic event | *MI, **PE, ***DVT |

*MI – Myocardial infarction in a 77 years old patient one day after surgery, PE – pulmonary emboli 6 weeks post operative date and one week after LMWH was stopped. *DVT – deep vein thrombosis proximal, in the affected leg, 6 weeks post operative date and one week after LMWH was stopped. The patient had active breast cancer.

Fig. 14

TAT

D-Dimer

METHODS AND KITS FOR ASSESSING HEPARANASE PROCOAGULANT ACTIVITY, COMPOSITIONS COMPRISING HEPARANASE, AND METHODS FOR THE TREATMENT OF COAGULATION RELATED DISORDERS

FIELD OF THE INVENTION

The present invention relates to a method for determining heparanase procoagulant activity in a biological sample. More particularly, the present invention relates to a method for the diagnosis of a coagulation-related disorder in a subject, associated with an elevation of the procoagulant activity of heparanase. The invention further provides combination therapy for the treatment of coagulation-related disorders. More particularly, the invention relates to compositions combining heparanase with tissue factor (TF). The compositions of the invention may particularly be used for the treatment of coagulation-related disorders. The invention further provides methods of treatment of such disorders using these combined compositions and methods of screening for modulators of coagulation processes.

BACKGROUND OF THE INVENTION

All publications mentioned throughout this application are fully incorporated herein by reference, including all references cited therein.

One of the major physiological roles of the endothelium is to preserve the integrity of the vasculature by its permeability barrier properties, and to provide a non-thrombogenic surface. Therefore, the endothelial cell surface serves as a prime regulatory site of coagulation responses. Under normal circumstances, an injury to vascular endothelial cells lining a blood vessel triggers a haemostatic response through a sequence of events commonly referred to as the "coagulation cascade". The cascade culminates in the conversion of soluble fibrinogen to insoluble fibrin which, together with platelets, forms a localized clot or thrombus which prevents extravasation of blood components. Wound healing can then occur followed by clot dissolution and restoration of blood vessel integrity and flow.

The events which occur between injury and clot formation are carefully regulated and linked series of reactions, involving number of plasma coagulation proteins in inactive proenzyme forms and cofactors circulate in the blood. Active enzyme complexes are assembled at an injury site and are sequentially activated to serine proteases, with each successive serine protease catalyzing the subsequent proenzyme to protease activation. This enzymatic cascade results in each step magnifying the effect of the succeeding step. In brief, the blood coagulation cascade is usually initiated as soon as the cell surface glycoprotein tissue factor (TF) comes into contact with circulating activated factor VII (VIIa), resulting in the formation of TF-FVIIa complex. The TF-VIIa complex activates X to factor Xa. Subsequently, factor Xa catalyzes the conversion of prothrombin to thrombin, thereby leading to fibrin formation, platelet activation, and, ultimately, generation of a thrombus. Tissue factor pathway inhibitor (TFPI) is a potent direct inhibitor of factor Xa, and in a factor Xa dependent fashion, produces inhibition of the factor VIIa-TF complex.

While efficient clotting limits the loss of blood at an injury site, inappropriate formation of thrombi in veins or arteries is a common cause of disability and death. Abnormal clotting activity can result in and/or from pathologies or treatments such as myocardial infarction, unstable angina, atrial fibrillation, stroke, renal damage, percutaneous translumenal coronary angioplasty, disseminated intravascular coagulation, sepsis, gestational vascular complications, pulmonary embolism and deep vein thrombosis. The formation of clots on foreign surfaces of artificial organs, shunts and prostheses such as artificial heart valves is also problematic.

Approved anticoagulant agents currently used in treatment of these pathologies and other thrombotic and embolic disorders include the sulfated heteropolysaccharides heparin and low molecular weight heparin (LMWH). These agents are administered parenteral and can cause rapid and complete inhibition of clotting.

Heparanase is an endo-β-D-glucuronidase capable of cleaving heparan sulfate (HS) side chains at a limited number of sites, yielding HS fragments of still appreciable size (~5-7 kDa) [Freeman, C. and Parish, C. R. Biochem. J. 330:1341-1350 (1998); Pikas, D. S. et al. J. Biol. Chem. 273:18770-18777 (1998)]. Expression of heparanase is restricted primarily to the placenta, platelets, keratinocytes, and activated cells of the immune system, with little or no expression in connective tissue cells and most normal epithelia [Parish, C. R. et al. Biochem. Biophys. Acta 1471:M99-108 (2001); Vlodaysky, I. and Friedmann, Y. J. Clin. Invest. 108:341-347 (2001)]. During embryogenesis, the enzyme is preferentially expressed in cells of the developing vascular and nervous systems. Heparanase activity was implicated in tumor growth, neovascularization, inflammation and autoimmunity [Parish (2001) ibid.; Vlodaysky (2001) ibid.; Dempsey, L. A. et al. Trends Biochem. Sci. 25:349-351 (2000)]. A single human heparanase cDNA sequence was independently reported by several groups [Hulett, M. D. et al. Nat. Med. 5:803-809 (1999); Kussie, P. H. et al. Biochem. Biophys. Res. Commun. 261:183-187 (1999); Toyoshima, M. and Nakajima, M. J. Biol. Chem. 274:24153-24160 (1999); Vlodaysky, I. et al. Nat. Med. 5:793-802 (1999)]. Thus, unlike the large number of proteases that can degrade polypeptides in the extra-cellular matrix (ECM), one major heparanase appears to be used by cells to degrade the HS side chains of HS proteolycans.

Heparanase is synthesized as a latent 65 kDa precursor whose activation involves proteolytic cleavage at two potential sites located at the N-terminal region of the molecule (Glu109-Ser110 and Gln157-lys158), resulting in the formation of two protein subunits, 8 and 50 kDa polypeptides, that heterodimerize and form the active heparanase enzyme [McKenzie, E. et al. Biochemical J. 373: 423-35 (2003); Levy-Adam F. et al. Biochem. Biophy. Res. Commun. 308: 885-91 (2003)]. One of the prime physiological sources for heparanase are platelets [Hulett (1999) ibid.; Freeman and Parish (1998) ibid.]. The 50 and 8 kDa heparanase polypeptides were biochemically purified from platelets, which also contain significant amounts of the 65 kDa proenzyme [Hulett (1999) ibid; Freeman (1998) ibid.]. Moreover, the heparanase gene was previously cloned from human platelets [Hulett (1999) ibid.]. Heparanase released by activated platelets or platelet-derived microparticles, is biologically active, stimulates angiogenesis and modulates endothelial cell activities [Brill, A. et al. Cardiovasc. Res. 63:226-235 (2004); Myler, H. A. and West, J. L. J. Biochem. 131:913-922 (2002)].

It has been previously shown by applying heparanase which lacks enzymatic activity that heparanase exerts also non-enzymatic activities, independent of its involvement in ECM degradation and alterations in the extracellular microenvironment associated with angiogenesis, cell survival, and migration [Goldshmidt, O. Faseb. J. 17:1015-1025

(2003); Gingis-Velitski, S. et al. J. Biol. Chem. 279:23536-23541 (2004); Zetser, A. et al. Cancer Res. 66:1455-1463 (2006)].

The inventors have recently demonstrated that heparanase is also involved in the hemostatic system. Heparanase was shown to up-regulate TF expression [Nadir, Y. J. et al. Thromb. Haemost. 4:2443-2451 (2006)] and interact with TFPI on the cell surface, leading to dissociation of TFPI from the cell membrane and increased cell surface coagulation activity [Nadir, Y. et al. Thromb. Haemost. 99:133-141 (2008)].

When the present inventors further examined the role of heparanase in coagulation modulation, they surprisingly and unexpectedly found, as shown by the present invention, that heparanase is directly involved in the activation of the coagulation system by enhancing factor Xa production in the presence of TF/VIIa complex.

More particularly, addition of heparanase to TF and factor VIIa resulted in three to four fold increase in activation of the coagulation cascade as depicted by increased factor Xa and thrombin production. When heparanase was added to pooled normal plasma a seven to eight fold increase in Xa level was observed. Subsequently, the inventors looked for clinical data supporting the existence of this innovative role of heparanase. Plasma samples of thirty five patients with acute leukemia at presentation, and twenty healthy controls were studied for heparanase and factor Xa levels using ELISA and chromogenic assay, respectively. A strong positive correlation was found between plasma heparanase and Xa levels (r=0.735, p=0.001). In addition, unfractionated-heparin and an anti-Xa derivative abolished the effect of heparanase, while, TFPI and TFPI-2 only attenuated the procoagulant effect. Finally, co-immunoprecipitation and far-western analyses demonstrated that heparanase directly interacts with TF. Altogether, the results presented herein support the notion that heparanase is a modulator of blood homeostasis, and suggest a novel mechanism by which heparanase is involved in direct activations of the coagulation cascade by direct interaction with TF.

For the purpose of better assessing the procoagulant role of heparanase in various medical conditions, the inventors have developed an original assay to evaluate heparanase procoagulant activity in biological samples. Heparanase procoagulant activity was preliminary studied using purified proteins of heparanase, TF, factor VIIa and factor X. The methodology was verified in fifty five plasma samples and compared to heparanase and tissue factor pathway inhibitor (TFPI) levels by ELISA and factor Xa, thrombin levels and antithrombin activity by chromogenic substrates. Thirty five samples were of third-trimester pregnant women (weeks 36-41) who were in labor or came for appointed elective cesarean section and 20 control samples were of non-pregnant healthy women. The heparanase procoagulant activity assay was shown to differentiate heparanase procoagulant effect from TF activity, in purified proteins model. Heparanase procoagulant activity was significantly higher in the plasma of pregnant women compared to non-pregnant (p<0.005). Heparanase relative contribution to the TF heparanase complex activity was significantly higher in the plasma of pregnant women compared to non-pregnant (29% increase, p<0.0001). Differences in heparanase procoagulant activity were more prominent than changes in heparanase levels by ELISA, TF activity, factor Xa, thrombin and free TFPI levels. The results presented therein demonstrate that heparanase procoagulant activity can be determined by the assay and the methodology of the present invention. In this particular case, the assay of the invention revealed a significant contribution of heparanase to the procoagulant state in late third-trimester pregnancy and at delivery.

The methodology and the assay developed in the present invention were then applied to the field of orthopedic hip and knee surgeries which are followed by a hypercoagulable state. Heparanase level and procoagulant activity in patients undergoing orthopedic surgery were assessed. The study group included fifty orthopedic patients. Thirty one patients underwent hip surgery and nineteen had knee operation. Fifteen individuals suffered from traumatic hip fractures and thirty five had osteoarthrosis of hip or knee joints. All patients received prophylactic dose of enoxaparin (a low molecular weight heparin) starting 6-8 hours post operation and lasting for five weeks. Plasma samples were drawn preoperatively and at 1 hour, 1 week and 1 month post operation. Samples were tested for heparanase levels by ELISA and TF/heparanase complex activity, TF activity, heparanase procoagulant activity (with the assay of the present invention), factor Xa and thrombin levels using chromogenic substrates. Heparanase levels were significantly higher 1 hour and 1 week post operatively compared to preoperative levels (p<0.05, p<0.005, respectively). The most dramatic changes were observed in heparanase procoagulant activity reaching a 2 fold increase 1 week postoperatively and 1.7 fold increase 1 month after surgery (p<0.0001, p<0.0001, respectively). Levels of factor Xa and thrombin did not significantly change. In conclusion, the inventors demonstrated that heparanase is involved in coagulation activation of orthopedic surgery patients. Heparanase procoagulant activity is highest 1 week postoperatively and remains high 1 month after operation. In view of the above, considering extending prophylactic anticoagulant therapy or evaluating heparanase procoagulant activity may potentially prevent late thrombotic events.

It is therefore one object of the invention to provide a composition comprising a combination of heparanase or any fragments, derivative or peptides thereof and TF or any fragments, derivatives or peptides thereof, specifically for use in modulation of coagulation processes.

In yet another object, the invention provides a method for the activation of a pro-coagulation process in a subject in need thereof, using the combined heparanase-TF compositions of the invention. These methods are specifically applicable in the treatment, amelioration and prevention of coagulation-related pathologic conditions In yet another object, the invention provides the use of the novel heparanase-TF interaction as a target in a screening method for identification of coagulation-modulating compounds. Such compounds modulate the heparanase-TF mediated coagulation activity in a subject suffering of a coagulation-related disorder.

In yet another object, the invention provides a method for determining heparanase procoagulant activity in a biological sample of a mammalian subject.

In yet another object, the invention provides a diagnostic method for the detection and/or monitoring of a coagulation-related pathologic disorder in a mammalian subject.

In yet another object, the invention provides a diagnostic kit for the detection and/or monitoring of a coagulation-related pathologic condition in a mammalian subject.

These and other objects of the invention will become apparent as the description proceeds.

SUMMARY OF THE INVENTION

In a first aspect, the present invention provides a method for determining heparanase procoagulant activity in a biological sample of a mammalian subject, said method comprising the steps of:

(a) preparing a first test solution (TS1) comprising a buffer solution, factor VIIa, and factor X;
(b) preparing a second test solution (TS2) comprising a buffer solution, factor VIIa, factor X, and an inhibitor capable of disrupting the Heparanase/Tissue Factor (Hepa/TF) complex;
(c) contacting aliquots of said biological sample with TS1 and TS2;
(d) adding to TS1 and to TS2 a substrate to factor Xa suitable to produce an optically detectable product;
(e) measuring the level of said optically detectable product in TS1 (L1); and
(f) measuring the level of said optically detectable product in TS2 (L2); wherein heparanase procoagulant activity (HPA) is obtained by subtracting L2 from L1, and heparanase relative contribution to the coagulation system is obtained by dividing HPA by L1.

In another aspect, the invention provides a diagnostic method for the detection and/or monitoring of a coagulation-related pathologic disorder in a mammalian subject, comprising the steps of:
(a) determining the level of heparanase procoagulant activity in a biological sample of said subject; and optionally determining the value of heparanase procoagulant activity in a control biological sample;
(b) comparing the value of heparanase procoagulant activity of said biological sample to a predetermined control value or to the value of heparanase procoagulant activity of said control sample;
wherein a higher or lower level of heparanase procoagulant activity in said biological sample as compared to said control sample or said predetermined control value is indicative of a coagulation-related pathologic disorder in said subject.

In yet another aspect, the present invention provides a diagnostic kit for the detection and/or monitoring of a coagulation-related pathologic condition in a mammalian subject, comprising:
(a) coagulating agents comprising factor X and factor VIIa;
(b) a compound inhibiting the interaction of heparanase and TF;
(c) substrate to factor Xa; and optionally
(d) one or more components selected from the group consisting of instructions for carrying out the detection of the procoagulant activity of heparanase in said subject; control samples; and predetermined calibration curve and instructions for using the same.

In a further aspect, the present invention provides a composition comprising a combination of at least one heparanase molecule and any fragments, derivative or peptides thereof and at least one tissue factor (TF) molecule and any fragments, derivatives or peptides thereof, said composition optionally further comprising at least one additional therapeutic agent and pharmaceutically acceptable carrier, diluent, excipient and/or additive.

In yet a further aspect, the invention provides a pharmaceutical composition for treating, preventing or ameliorating a coagulation-related pathologic condition in a subject in need thereof, said composition comprising as active ingredient a therapeutically effective amount of a combination of at least one heparanase molecule and any fragments, derivative or peptides thereof and at least one tissue factor (TF) molecule and any fragments, derivatives or peptides thereof. Said composition optionally further comprises at least one additional therapeutic agent and at least one of a pharmaceutically acceptable carrier, diluent, excipient or additive.

In yet another aspect, the present invention provides a method for the activation of a pro-coagulation process in a subject in need thereof, said method comprising the step of administrating to said subject a therapeutically effective amount of a combination of at least one heparanase molecule and any fragments, derivative or peptides thereof and at least one tissue factor (TF) molecule and any fragments, derivatives or peptides thereof, or any composition comprising the same, said composition optionally further comprising at least one additional therapeutic agent and a pharmaceutically acceptable carrier, diluent, excipient and/or additive.

In a further aspect, the present invention provides a method for the treatment, amelioration and prevention of a coagulation-related pathologic condition, said method comprising the step of administering to a subject in need thereof an effective amount of a combination of at least one heparanase molecule and any fragments, derivative or peptides thereof and at least one tissue factor (TF) molecule and any fragments, derivatives or peptides thereof, or any composition comprising the same, said composition optionally further comprising at least one additional therapeutic agent and pharmaceutically acceptable carrier, diluent, excipient and/or additive.

In yet a further aspect, the present invention provides the use of a therapeutically effective amount of a combination of at least one heparanase molecule and any fragments, derivative or peptides thereof and at least one tissue factor (TF) molecule and any fragments, derivatives or peptides thereof, in the preparation of a medicament for the treatment of a coagulation-related pathologic condition.

In an even further aspect, the present invention provides a kit for achieving a therapeutic effect in a subject suffering of a coagulation-related pathologic condition comprising:
(a) at least of any heparanase molecule, or any pharmaceutically acceptable fragments, derivatives, peptides thereof, and a pharmaceutically acceptable carrier or diluent, optionally, in a first unit dosage form;
(b) at least one TF molecule, any pharmaceutically acceptable fragments, derivatives, peptides thereof and a pharmaceutically acceptable carrier or diluent, optionally, in a second unit dosage form; and
(c) container means for containing said first and second dosage forms.

Even further, in another aspect the present invention provides a method for treating, preventing or ameliorating a coagulation-related pathologic condition in a subject in need thereof, said method comprising the step of administering to said subject a therapeutically effective amount of a first and second unit dosage forms comprised in the kit as described above.

In another aspect, the present invention provides a screening method for a coagulation modulatory compound, wherein said compound binds the heparanase-TF binding site within any one of the heparanase molecule or the TF molecule, and modulates the interaction of heparanase and TF and thereby modulates the coagulation activity in a subject suffering from a coagulation-related disorder, said screening method comprising the steps of:
(a) obtaining a candidate compound which binds to any one of heparanase molecule or to any fragment, variant, derivative and mutant thereof or to TF molecule or to any fragment, variant, derivative and mutant thereof;
(b) selecting from the candidate compounds obtained in step (a) a compound that modulates the direct interaction between said TF and heparanase or to any fragment, variant, derivative and mutant thereof; and
(c) determining the effect of the compound selected in step (b) on the heparanase-TF complex mediated pro-coagulation activity.

The invention will be further described by the hand of the following figures.

Heparanase Increases Factor Xa Levels

Figure 1A:
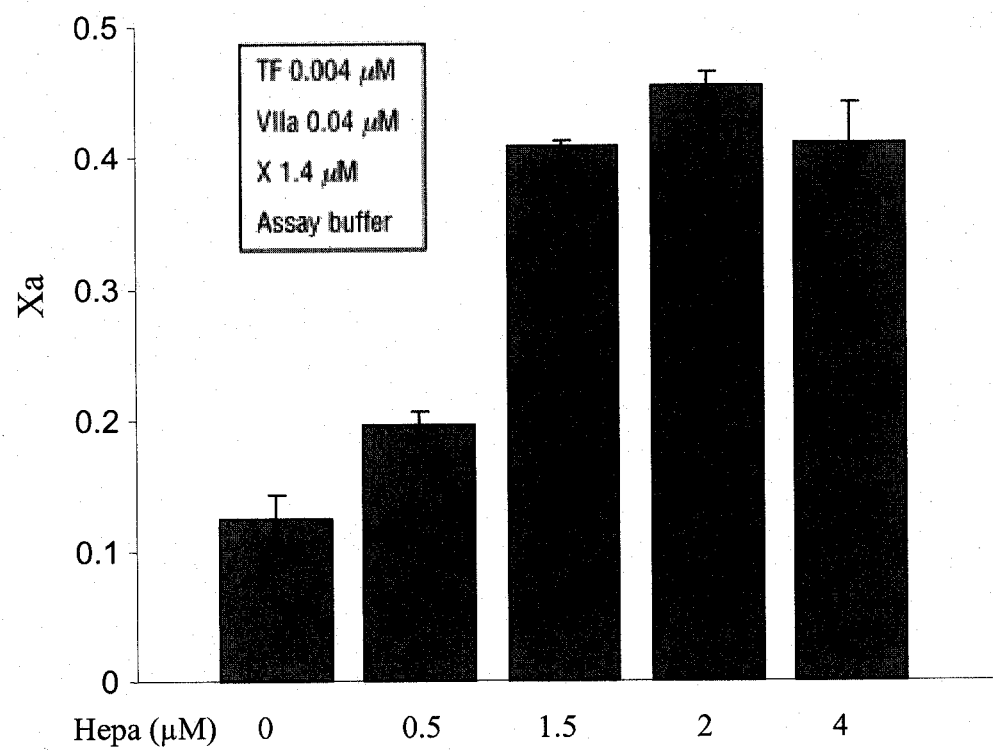
FIGS. 1A-1E

FIG. 1A. Recombinant human TF, recombinant human factor VIIa, and plasma-derived human factor X were incubated (15 min, 37° C.) in a total assay volume of 125 µL. Chromogenic substrate for the detection of factor Xa was then added (final concentration 1 mM). Recombinant active heparanase GS3 (Hepa) was added prior to the addition of the coagulation factors. The mean value±SD of three independent experiments in shown. A 3- to 4-fold increase in coagulation activity was obtained in the presence of heparanase.

Figure 1B:
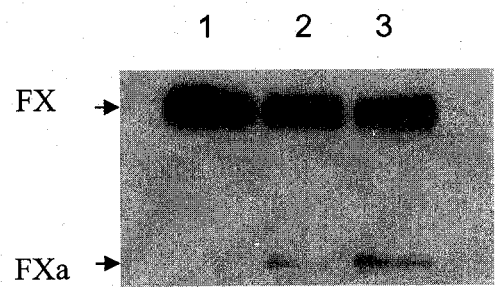

FIG. 1B. Western blot analysis. Lane 1: 50 ng of human factor X served as a control on SDS/PAGE followed by immunoblotting in which anti-human monoclonal antibody directed against the heavy chain of factor X and Xa was employed. Lane 2: sample, incubated as in A, in a reaction mixture containing 50 ng factor X (7 µM), was subjected to immunoblotting. Lane 3: Same as lane 2, except that heparanase (2 µM) was added prior to the addition of the coagulation factors. Note an increased generation of Xa in the presence of heparanase.

Figure 1C:
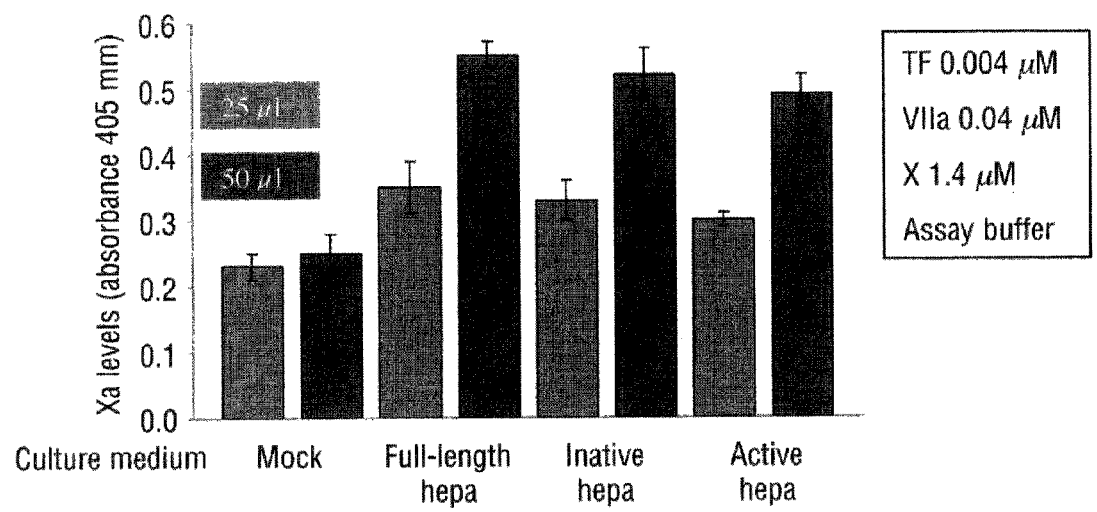

FIG. 1C. 25 µL or 50 µL of overnight serum-free medium without phenol of 293 HEK cells over-expressing full-length heparanase (65 kDa), enzymatically inactive heparanase (double mutant), active heparanase (GS3 8+50) and mock were incubated with TF, factor VIIa and X. After 15 min at 37° C., chromogenic substrate for Xa detection was added. The mean value of two experiments is shown. Note a 2-fold increase in coagulation activity when the medium contained heparanase or its derivatives.

Figure 1D:
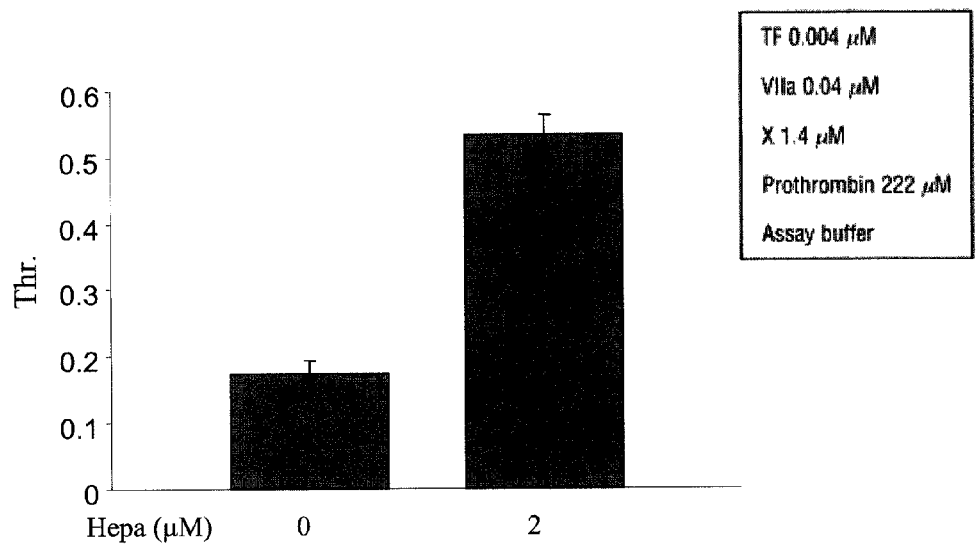

FIG. 1D. Heparanase increases thrombin levels. Recombinant human TF, recombinant human factor VIIa, plasma-derived human factor X, and plasma-derived human pro-thrombin were incubated (15 min, 37° C.) in a total volume of 125 µL. Chromogenic substrate for the detection of thrombin was then added (1 mM). Human recombinant heparanase (Hepa) was added prior to the addition of the coagulation factors. The mean value±SD of three independent experiments is shown. Note a 3-fold increase in coagulation activity in the presence of heparanase.

Figure 1E:
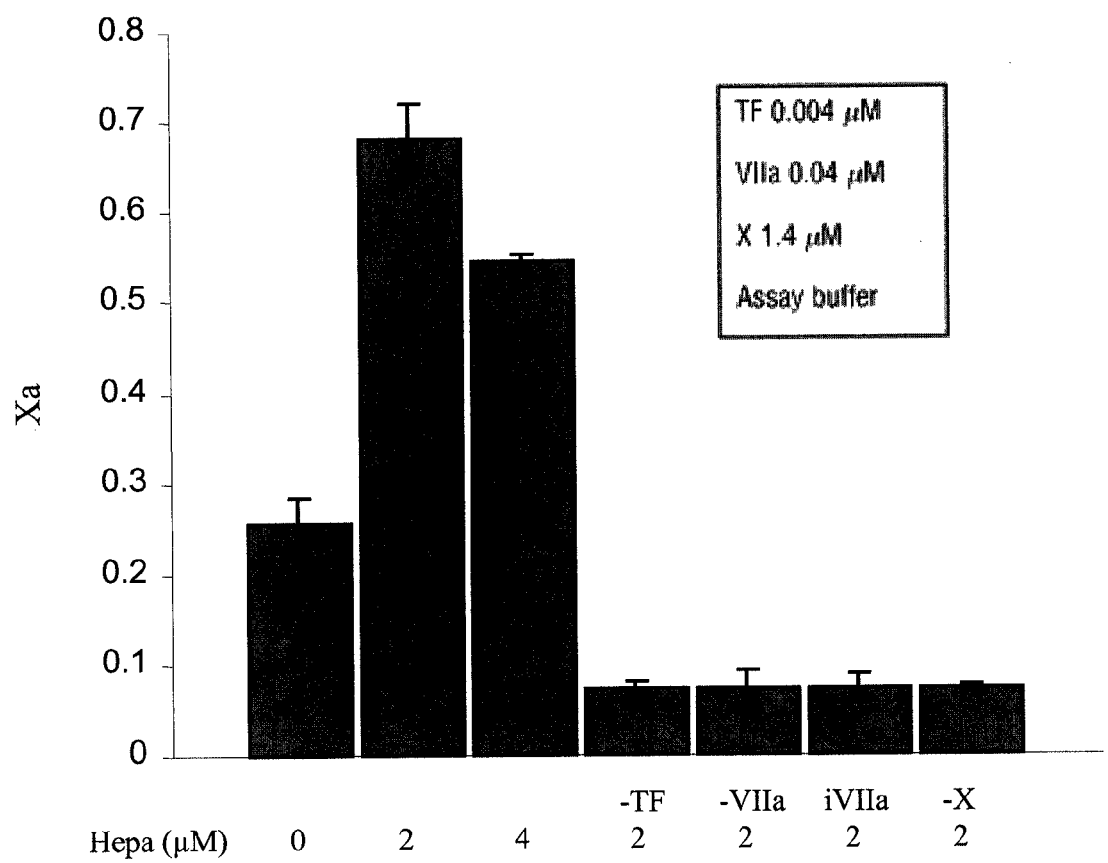

FIG. 1E. Each of the coagulation factors is needed for the heparanase-mediated increase in coagulation. Recombinant heparanase was incubated as described in FIG. 1A with either complete reaction mixture, reaction mixture lacking TF, factor VIIa, or factor X, or reaction mixture containing inactivated factor VIIa instead of factor VIIa. The mean value±SD of three independent experiments is shown. The results imply that the heparanase preparation is neither contaminated with, nor does it replace, any of the coagulation factors.

FIG. 2

Heparanase Increases Coagulation in Normal Human Plasma

Increasing doses of heparanase were added to pooled normal human plasma (25 µL plasma). After 15 min at 37° C., chromogenic substrate for the detection of factor Xa was added (1 mM). The mean value±SD of three independent experiments is shown. Note a 7- to 8-fold increase in coagulation activity in the presence of heparanase.

FIG. 3

Heparanase Reduces Time to Clot Formation and Increases Thrombus Strength

Thromboelastogram studies. The assay includes addition of factor VIIa, X and calcium to blood drawn into citrate in the presence or absence of heparanase. Each time, a sample with addition of heparanase (Hepa) and a sample without (Con)—were analyzed in parallel. R—The period of latency from the time that the blood was placed in the analyzer until the initial fibrin formation: this represents the coagulation factor activation. Angle—measures the rapidity of fibrin build-up and cross-linking: this represents the coagulation factor amplification. MA—A direct function of the maximum dynamic properties of fibrin and platelet bonding: signifies the ultimate strength of the clot. Note that in the presence of heparanase the clot is formed significantly faster and is stronger. At the highest dose, no effect on R is detected. The assays were done in pooled whole blood from three healthy donors and were repeated three times at each concentration revealing consistency. Representative results are shown.

FIG. 4

Correlation Between Plasma Heparanase and Factor Xa Levels

Plasma samples drawn from 35 patients with acute leukemia at presentation and from 20 healthy donors were evaluated for heparanase levels using ELISA and for factor Xa levels present in plasma (50 µL plasma, 50 µL assay buffer) applying a chromogenic substrate (1 mM, 30 min incubation). A strong positive correlation was found between the two parameters, suggesting an effect of heparanase on factor Xa levels.

FIGS. 5A-5B

Figure 5A:
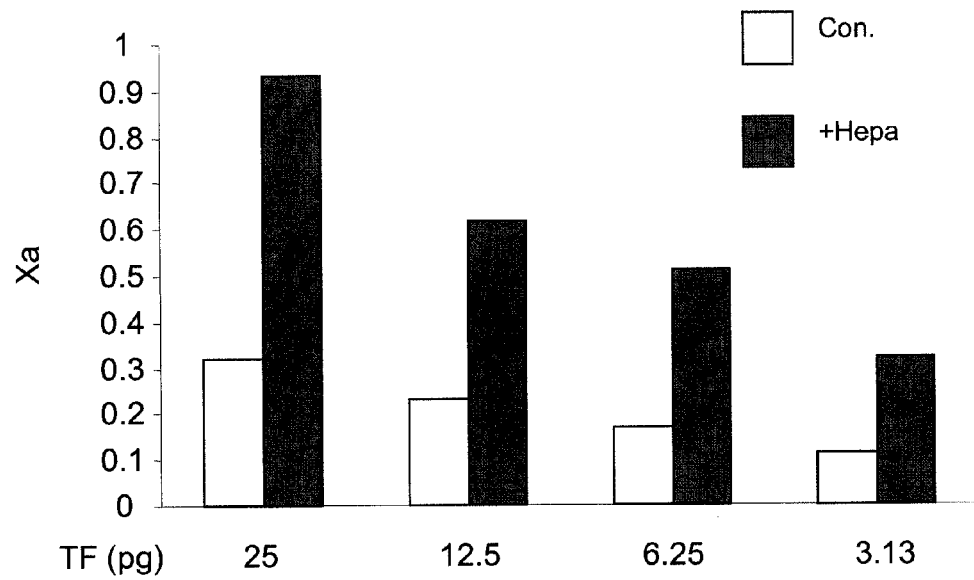

Heparanase Increases Coagulation by Enhancing TF Activity Rather than VIIa Activity FIG. 5A. The experiment in FIG. 1A was repeated using reduced levels of TF. White bars represent samples with no heparanase serving as controls. Gray bars represent samples with heparanase. Xa levels were determined by absorbance at 405 nm.

Figure 5B:
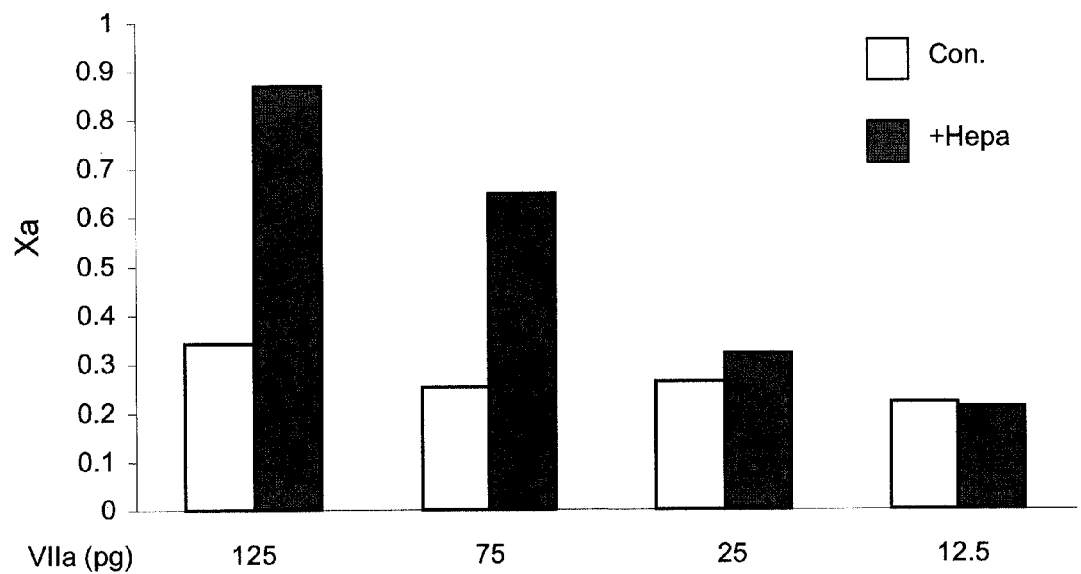

FIG. 5B. The experiment in FIG. 1A was repeated, but in this experiment the levels of VIIa were gradually reduced. White bars represent samples with no heparanase serving as controls. Gray bars represent samples with heparanase. Xa levels were determined by absorbance at 405 nm. Results of 6A and 6B are the mean if two separate experiments. Abbreviations: Hepa (heparanase); Con (control).

FIGS. 6A-6C

Inhibition of Heparanase Procoagulant Activity

Figure 6A:
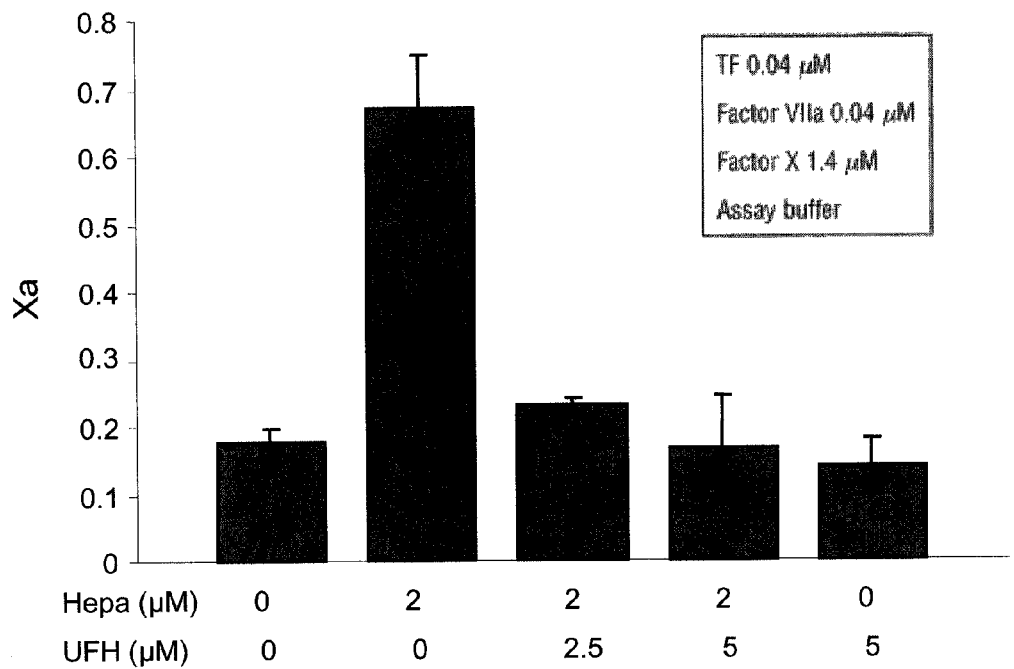

FIG. 6A. Heparanase procoagulant activity is abrogated by heparin. Same as FIG. 1A, except that unfractionated heparin (UFH) was added (2.5 µM=7.5 IU/mL) prior to heparanase.

Note that UFH abolished heparanase activity.

Figure 6B:
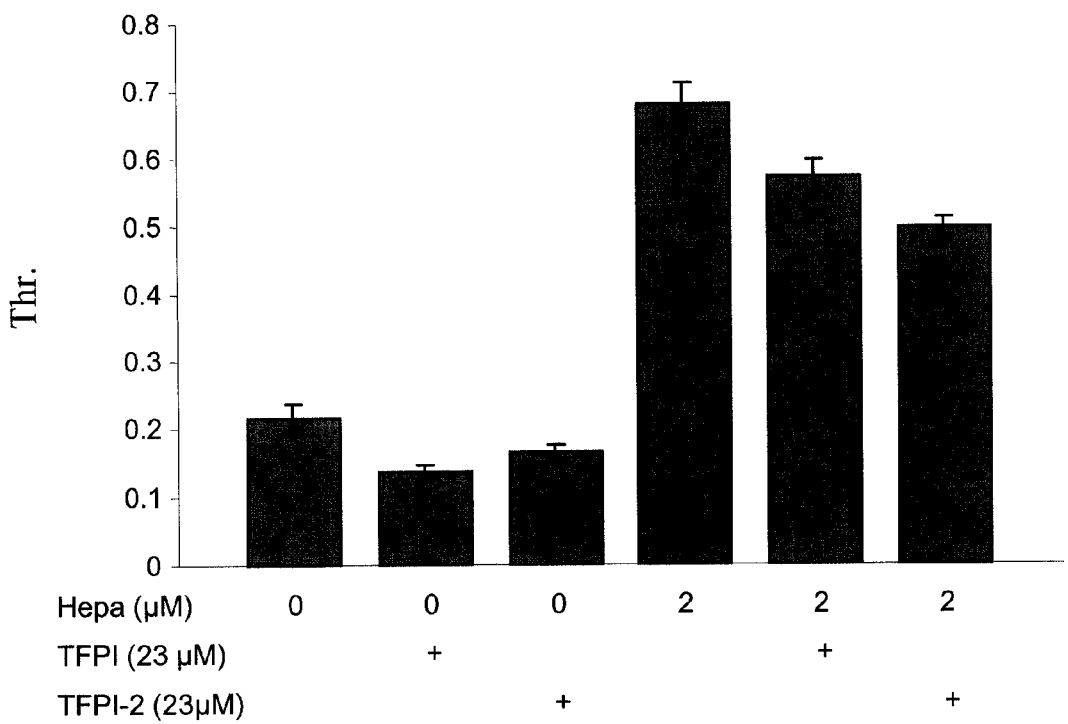

FIG. 6B. Heparanase procoagulant activity is attenuated by TFPI and TFPI-2. Same as FIG. 1D, except that recombinant human TFPI and TFPI-2 were added prior to heparanase addition. The mean value±SD of three independent experiments is shown. Note that TFPI and TFPI-2 mildly attenuated thrombin generation but failed to abolish the procoagulant effect of heparanase. TFPI-2 was more potent than TFPI in the presence of heparanase.

Figure 6C:
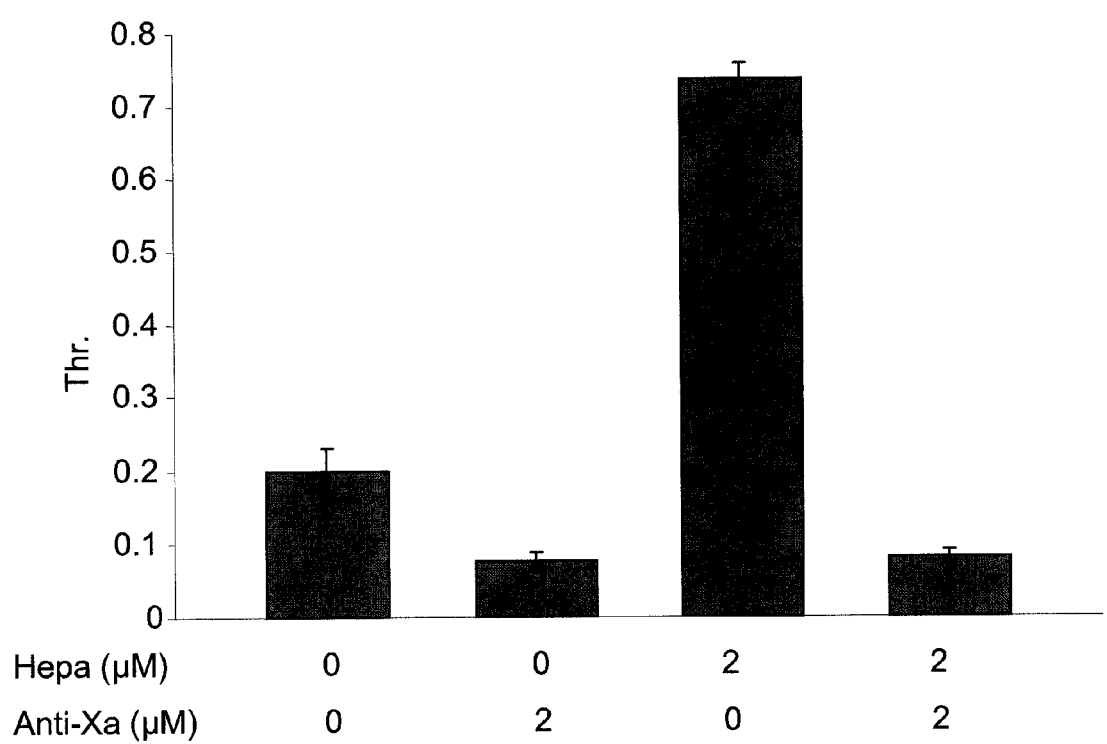

FIG. 6C. Heparanase procoagulant activity is abrogated by an anti-Xa derivative. Same as FIG. 1D, except that an anti-Xa derivative (Rivaroxaban) was added after factor X. Note that the anti-Xa derivative abolished the effect of heparanase, resembling the effect of UFH.

FIGS. 7A-7B

Direct Interaction Between Heparanase and TF

Figure 7A:
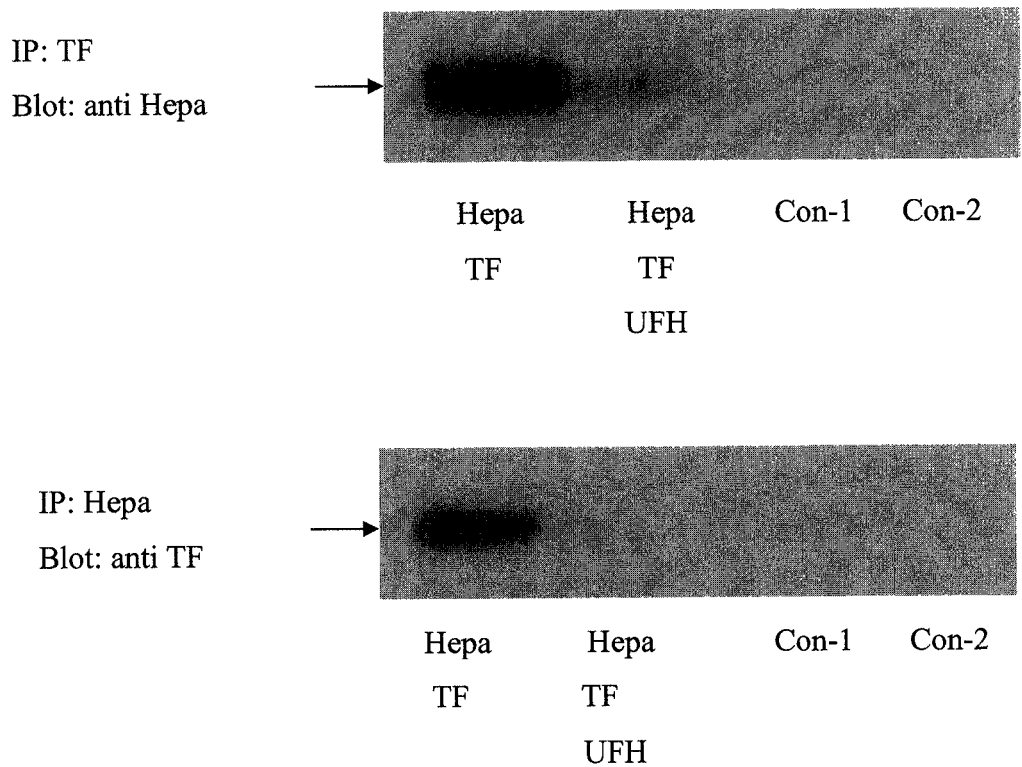

FIG. 7A. Co-immunoprecipitation. Purified TF (1 µg/mL) and GS3 active heparanase (1 µg/mL) proteins were incubated with beads coupled to polyclonal anti-TF (upper panel), or anti-heparanase (lower panel) antibodies. Bound proteins were analyzed by immunoblotting for the presence of heparanase (upper panel) or TF (lower panel), using the respective monoclonal antibody. Note the interaction between TF and heparanase, reduced or lack of interaction in the presence of unfractionated heparin (1 µg/mL=0.2 IU/mL), and lack of interaction with beads coupled to irrelevant anti-GST polyclonal antibody (Con-1), or to uncoupled beads (Con-2).

Figure 7B:
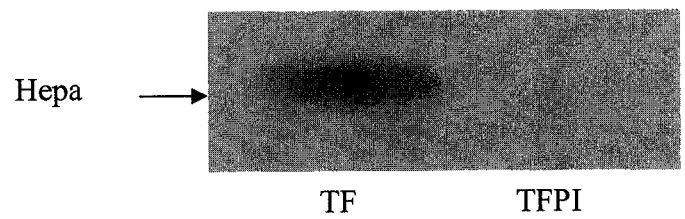

FIG. 7B. Far-western analysis. Recombinant TF (100 ng) and TFPI (100 ng) were resolved by SDS-PAGE under reducing conditions using a 10% gradient polyacrylamide gel. After electrophoresis, proteins were transferred to a polyvinylidene fluoride membrane. The membrane was incubated for 2 h with GS3 active heparanase protein (1 µg/mL, 4° C.). Next, the membrane was probed with anti-heparanase antibody followed by horseradish peroxidase-conjugated secondary antibody and chemiluminescence substrate, as described in the Design and Methods section. A clear band was revealed in the TF-heparanase lane but not in the TFPI-heparanase lane.

FIG. 8

Schematic Description of the Assay

Two parallel stages. In the first stage effect of TF in complex with heparanase is determined by level of Xa. In the second stage heparin interrupts the complex and as a result, effect of only TF is determined. The subtraction of TF/heparanase activity from the TF activity alone results in the determination of heparanase procoagulant contribution to TF.

FIGS. 9A-9C and 10A-10C

Figure 9A:
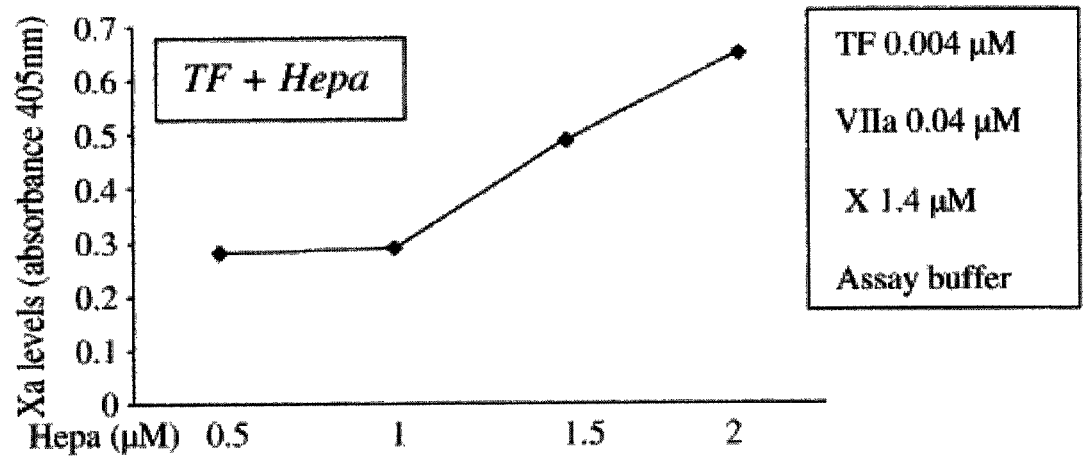
Figure 9B:
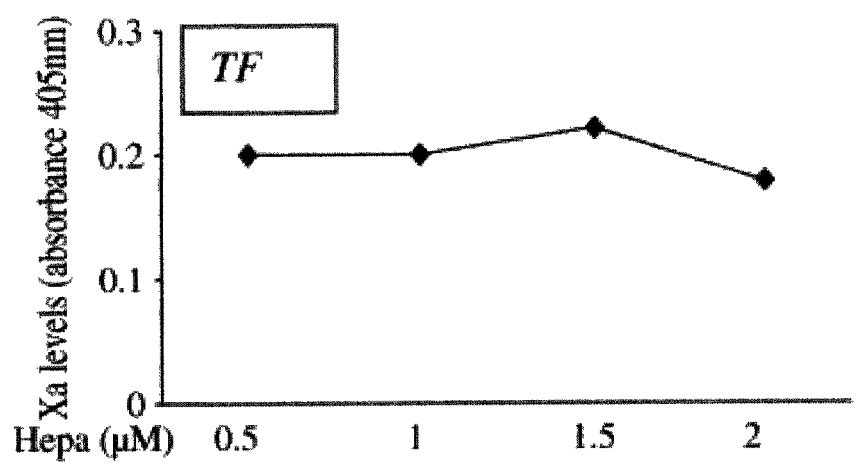
Figure 9C:
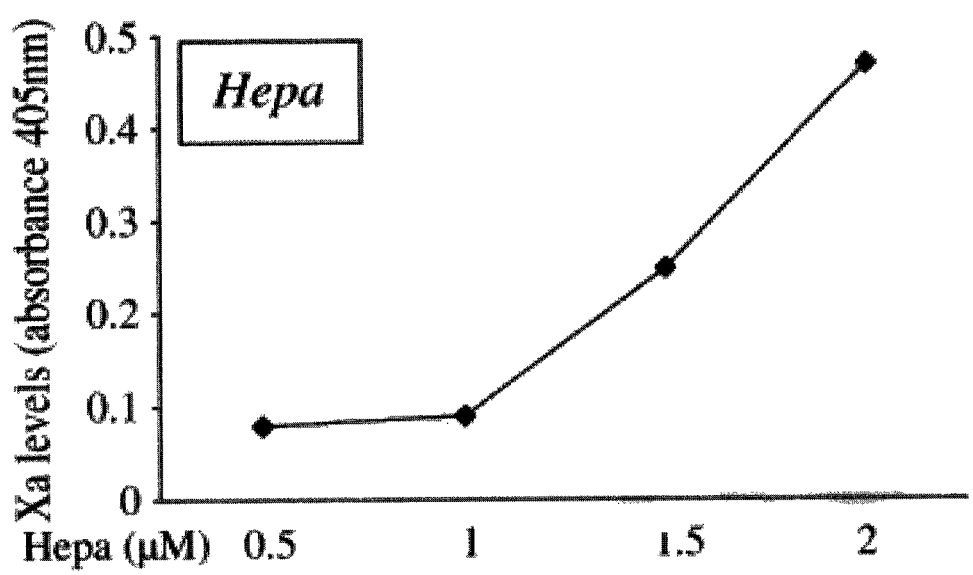

The Assay Discriminates Between TF Activity and Heparanase Procoagulant Activity FIGS. 9A-9C. Recombinant human TF, recombinant human factor VIIa, and plasma-derived human factor X were incubated (15 min, 37° C.) in a total assay volume of 125 µl. Chromogenic substrate for detection of Xa was then added (final concentration 1 mM). Recombinant active heparanase GS3 (Hepa) was added prior to the addition of the coagulation factors in increasing doses as indicated the result is shown in (TF+Hepa) [FIG. 9A]. Next, the same experiment was repeated with the addition of fondaparinux (10 µg/ml) prior to the addition of heparanase. The result is shown in (TF) [FIG. 9B]. (TF+Hepa)—TF determines heparanase procoagulant activity (Hepa) [FIG. 9C]. Shown is the mean of two independent experiments.

Figure 10A:
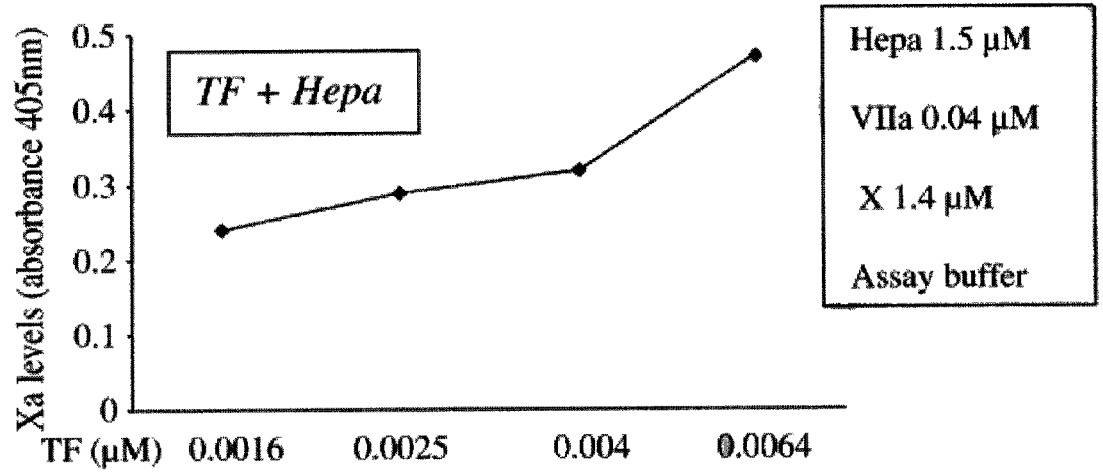
Figure 10B:
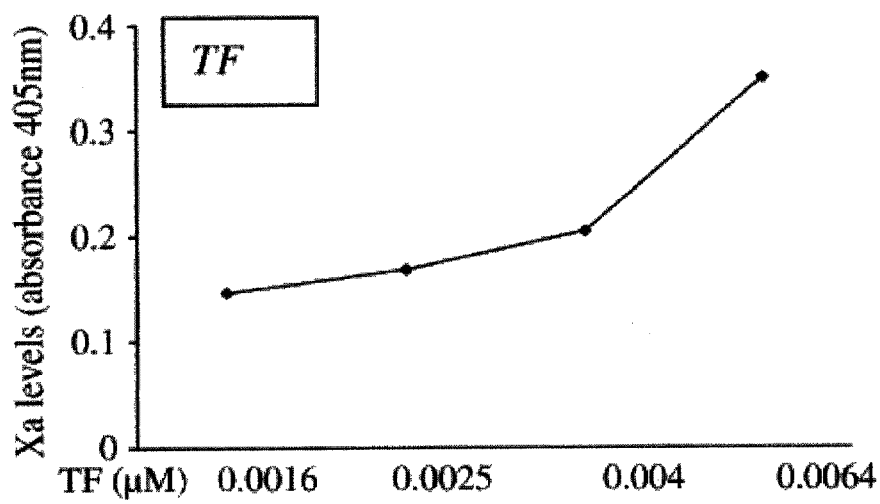
Figure 10C:
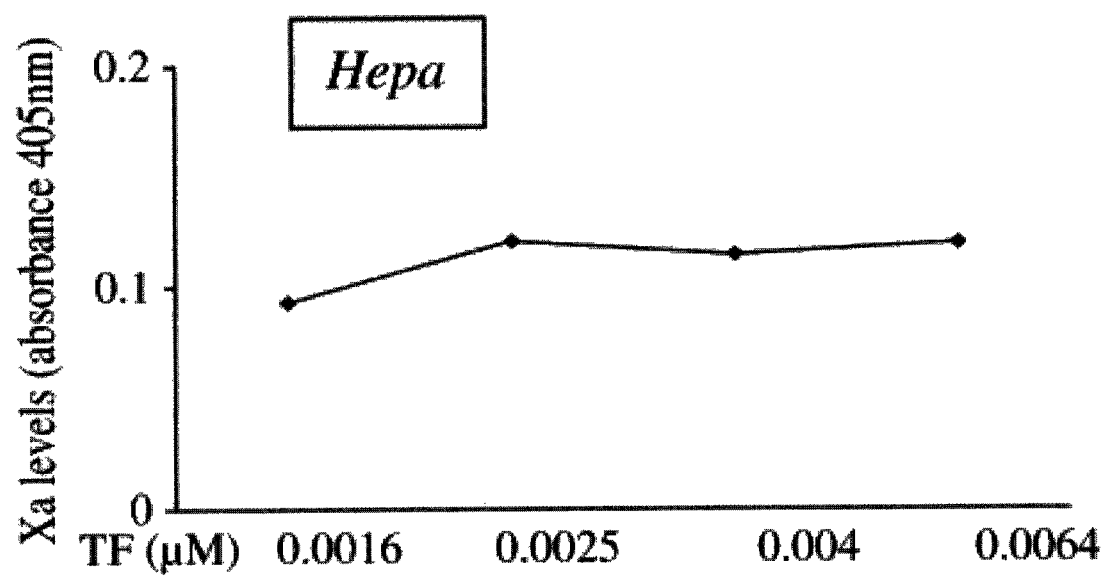

FIG. 10A-10C: Recombinant human TF, recombinant human factor VIIa, and plasma-derived human factor X were incubated (15 min, 37° C.) in a total assay volume of 125 µl. Chromogenic substrate for detection of Xa was then added (final concentration 1 mM). Recombinant human TF was added prior to the addition of the coagulation factors in increasing doses as indicated the result is shown in (TF+Hepa) [FIG. 10A]. Next, the same experiment was repeated with the addition of fondaparinux (10 µg/ml) prior to the addition of TF. The result is shown in (TF) [FIG. 10B]. (TF+Hepa)—Hepa determines Hepa procoagulant activity [FIG. 10C]. Shown is the mean of two independent experiments.

FIG. 11 is table 1. Table 1 discloses the demographic characteristics of the pregnant woman.

FIG. 12 is table 2. Table 2 discloses heparanase levels by ELISA and heparanase procoagulant assay in the pregnant women.

FIG. 13 is table 3. Table 3 discloses antithrombin activity, Factor Xa, thrombin and free TFPI levels in the pregnant women.

FIG. 14 is table 4. Table 4 discloses the demographic characteristics of the study group.

FIGS. 15A-15D

TF/Heparanase and Heparanase Procoagulant Activity Significantly Increase after Surgery and Reach Maximal Levels 1 Week Post Operation Plasma samples of 50 orthopedic patients were analyzed 1 hour preoperatively (n=50), 1 hour after operation (n=50), 1 week post operation (n=50) and 1 month post operation (n=30). *p<0.05, p<0.005, *p<0.0001. Results represent mean±SEM.

Figure 15A:
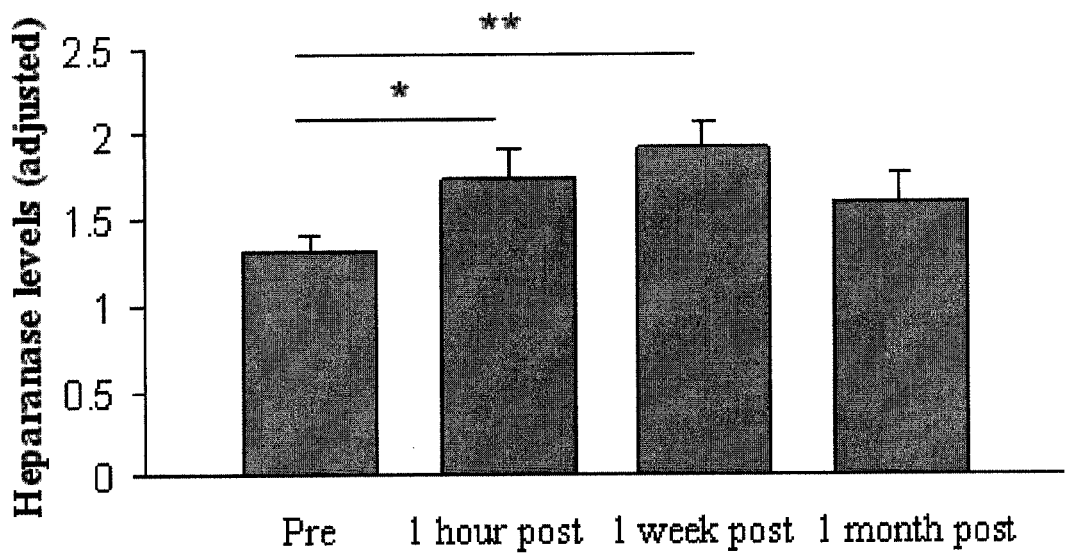
Figure 15B:
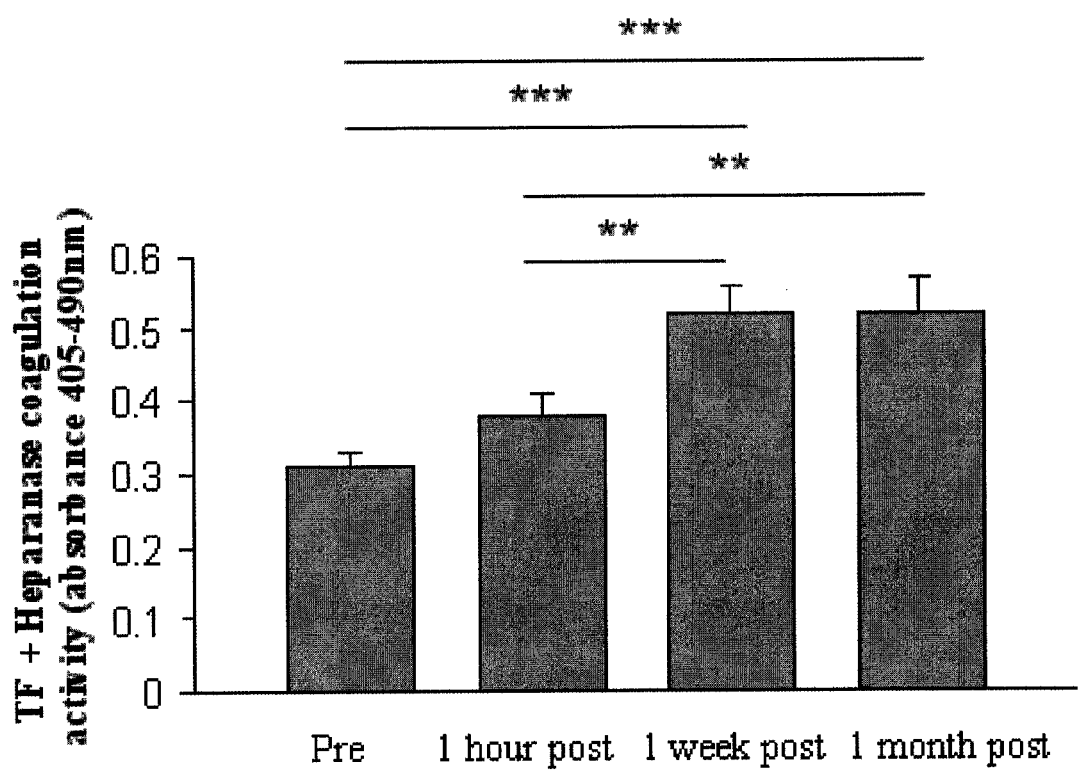
Figure 15C:
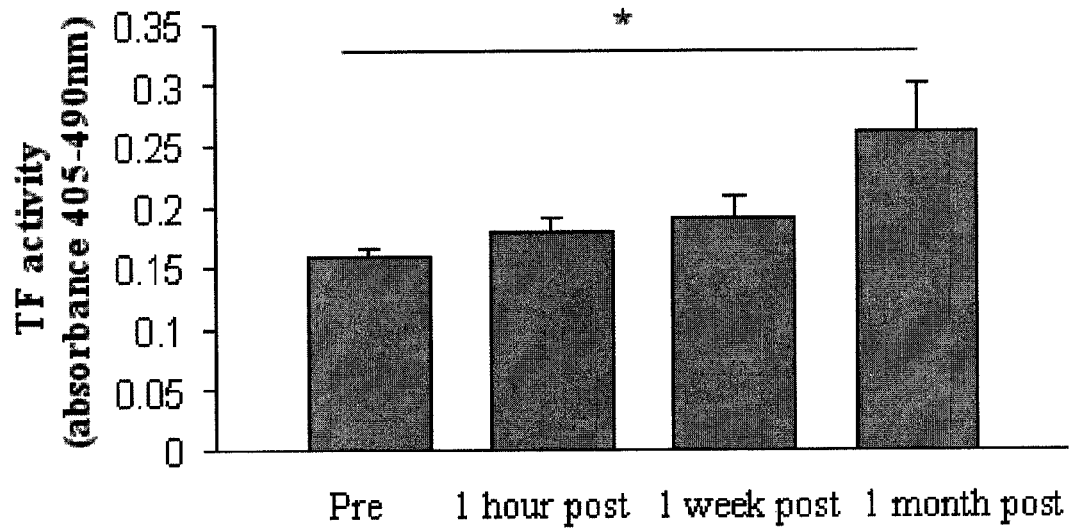
Figure 15D:
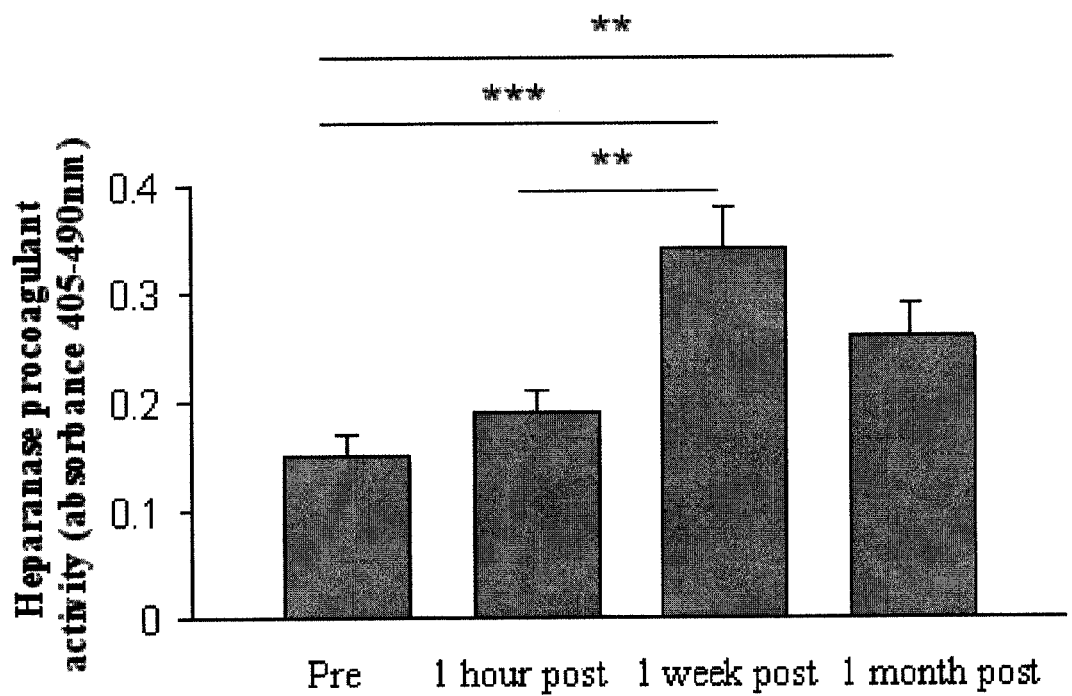

FIG. 15A. Heparanase levels.
FIG. 15B. TF+Heparanase coagulation activity.
FIG. 15C. TF activity
FIG. 15D. Heparanase procoagulant activity.

FIGS. 16A-16B

Factor Xa and Thrombin Levels do not Change Significantly in the Post Operative Period Plasma samples of 50 orthopedic patients were analyzed 1 hour preoperatively (n=50), 1 hour after operation (n=50), 1 week post operation (n=50) and 1 month post operation (n=30). * p<0.05. Results represent mean±SEM.

Figure 16A:
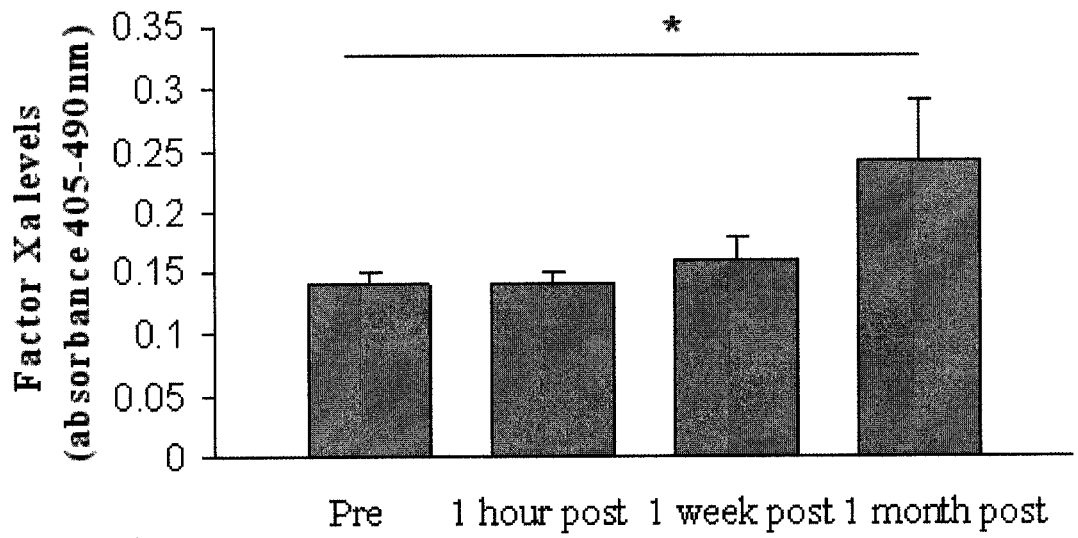
Figure 16B:
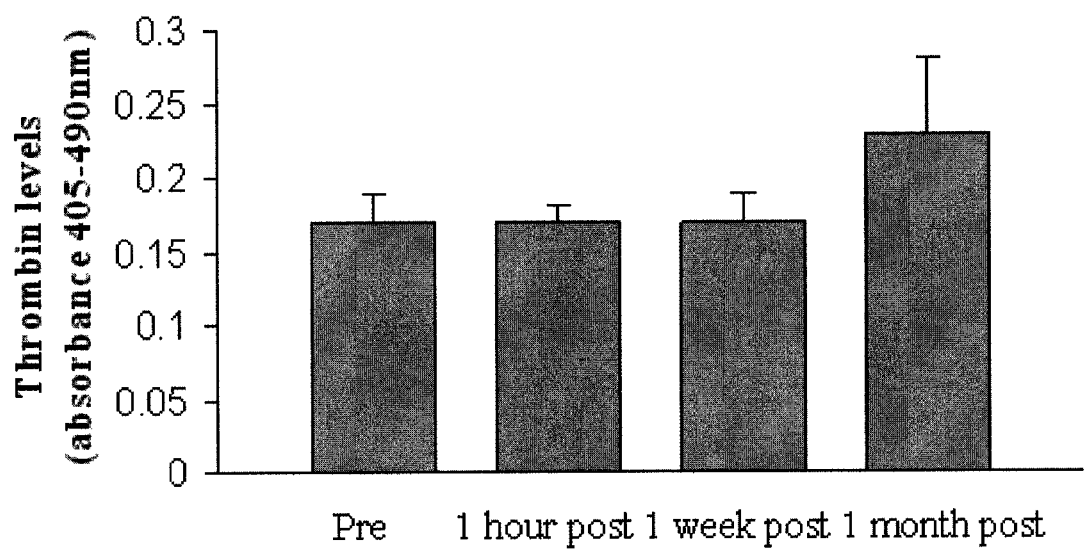

FIG. 16A. Factor X levels.
FIG. 16B. Thrombin levels.

FIGS. 17A-17B

Figure 17A:
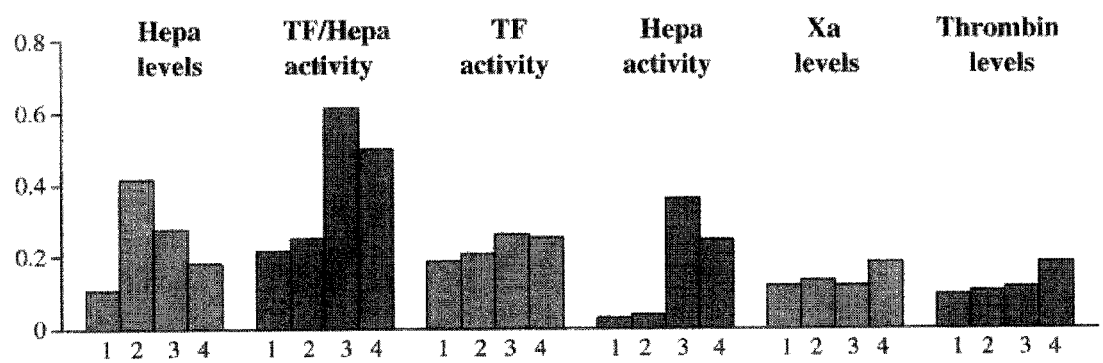

Hemostatic Balance of Two Patients with Thrombotic Events 6 Weeks after Operation FIG. 17A. A 70 years old female patient with PE one week after enoxaparin cessation. In her coagulation tests, the most dramatic change is the increased heparanase procoagulant activity at 1 month post operation (number 4), reaching 8 fold increase, compared to baseline levels (number 1).

Figure 17B:
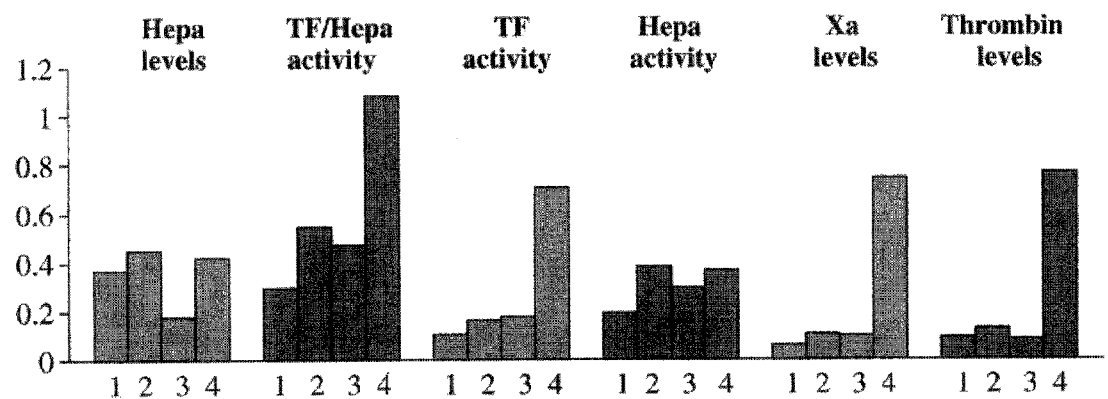

FIG. 17B. A 76 years old female with active breast cancer and DVT one week after enoxaparin cessation. In the coagulation tests, although heparanase procoagulant activity was two fold increased compared to baseline, the most striking increase was in TF activity (4 fold increase) as well as in factor Xa and thrombin levels, reaching 9 fold increase.

FIGS. 18A-18B

Heparanase Increases Coagulation Activation in Mice Model

Heparanase or LPS were injected to ICR mice and blood was drawn after 4 hours. Intra-peritoneal injection of heparanase (0.5 μg/mg) compared to PBS injection increased TAT ($p<0.05$) (18A) and D-Dimer ($p<0.05$) (18B) levels to similar levels induced by LPS (5 μg/mg).

Figure 18A:
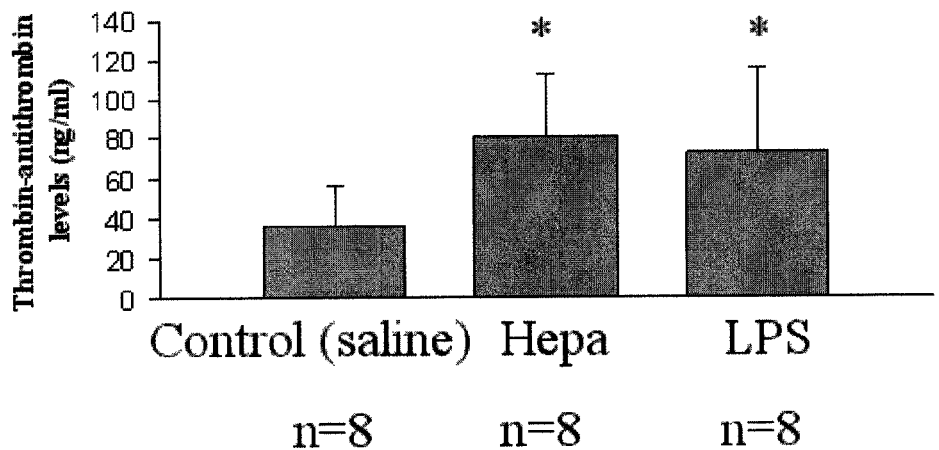
Figure 18B:
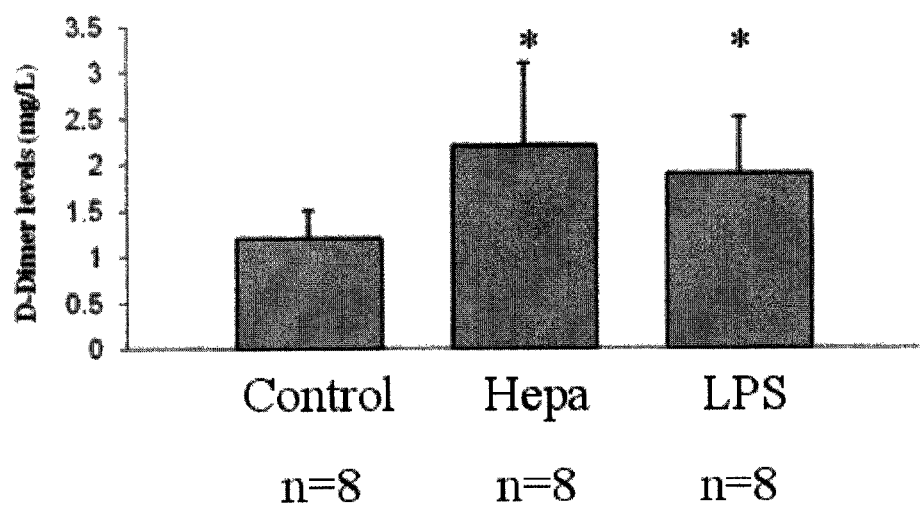
Figure 19:
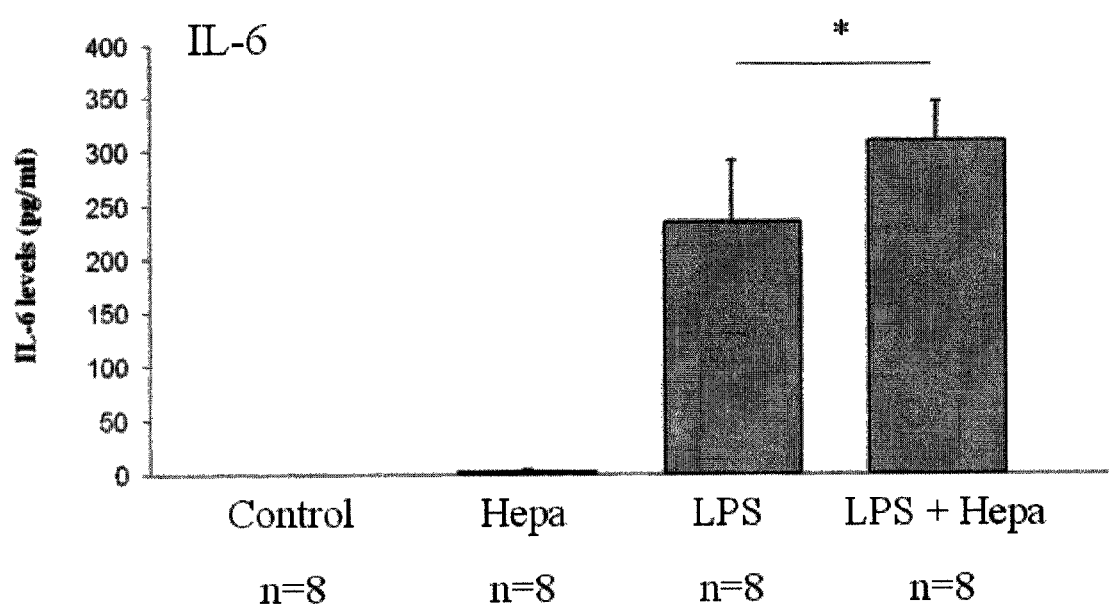

FIG. 18A. Thrombin-antithrombin levels.
FIG. 18B. D-dimer levels.

FIG. 19

IL-6 as a Marker of Sepsis Severity

Heparanase, LPS and LPS+heparanase were injected intra-peritoneal to ICR mice. Four hours later the blood was drawn and IL-6 level was measured by ELISA. Heparanase did not increase IL-6 level while addition of heparanase to LPS further augmented IL-6 level compared to LPS alone ($p<0.05$).

FIGS. 20A-20B

Heparanase Contributes to Consumption Coagulopathy in Sepsis

Heparanase, LPS and LPS+heparanase were injected intra-peritoneal to ICR mice. Four hours later the blood was drawn and thrombin-antithrombin (TAT) (20A) and D-dimer (20B) levels were evaluated by ELISA. Levels of TAT and D-dimer were reduced in the LPS+heparanase group compared to LPS alone in accordance with a severe activation of the coagulation system ($p<0.05$).

Figure 20A:
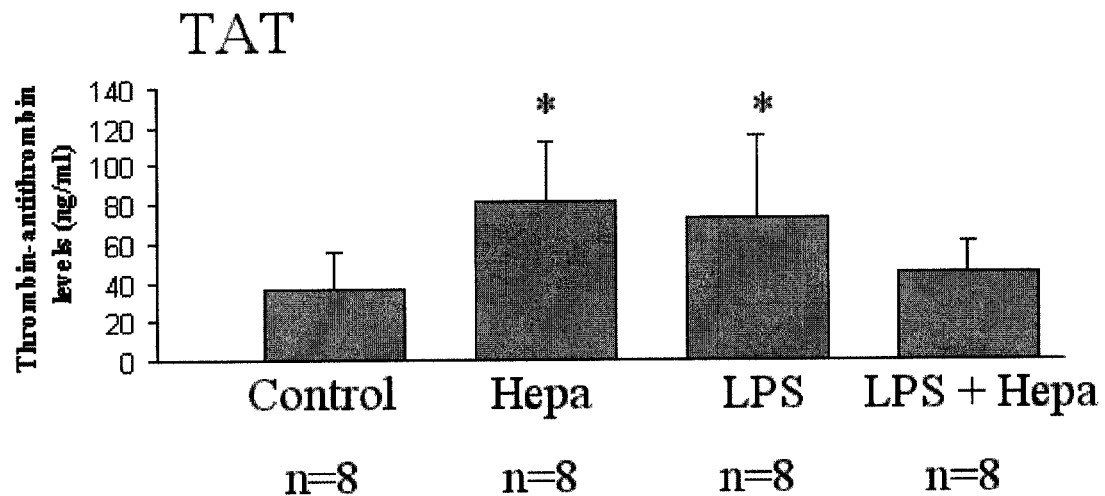
Figure 20B:
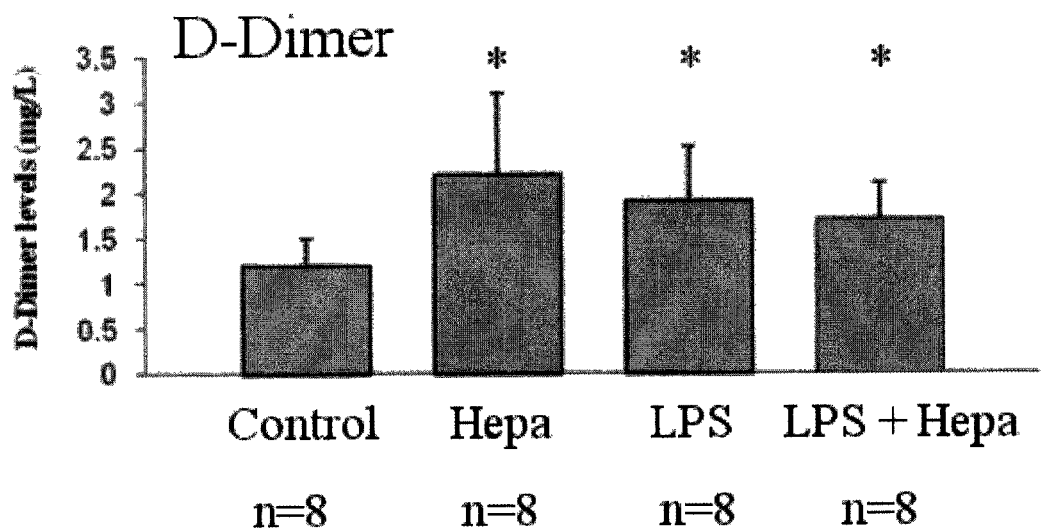

FIG. 20A. Thrombin-antithrombin levels.
FIG. 20B. D-dimer levels.

FIGS. 21A-21B

Heparanase Contributes to Coagulation Activation in Sepsis (1)

LPS was injected intra-peritoneal to heparanase over-expression mice. Four hours later the blood was drawn and IL-6 (21A) and thrombin-antithrombin (TAT) (21B) were evaluated by ELISA. Level of IL-6 was extremely high, mice were severely ill and TAT level was significantly reduced in the heparanase over-expression mice compared to wild type (WT) mice ($p<0.0001$), in accordance with a severe consumption coagulopathy.

Figure 21A:
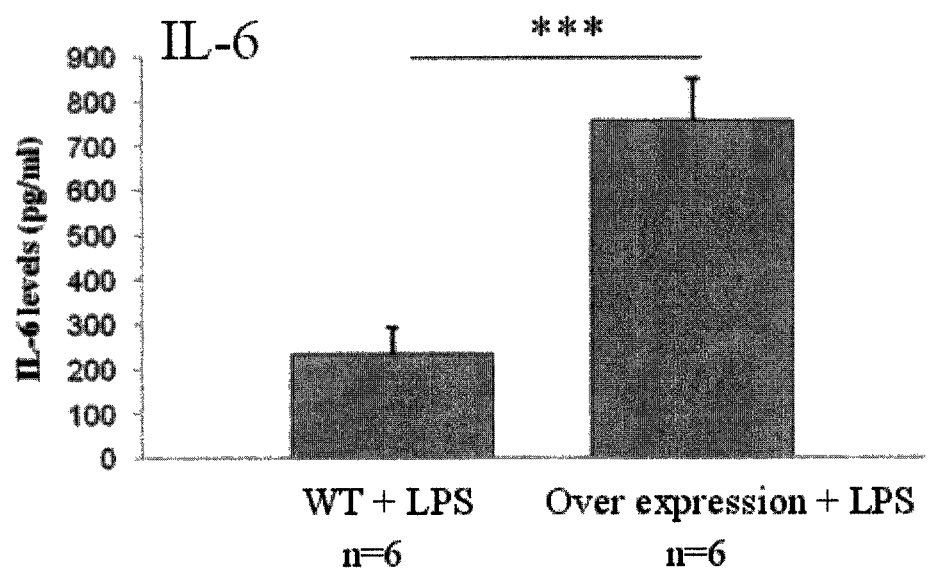
Figure 21B:
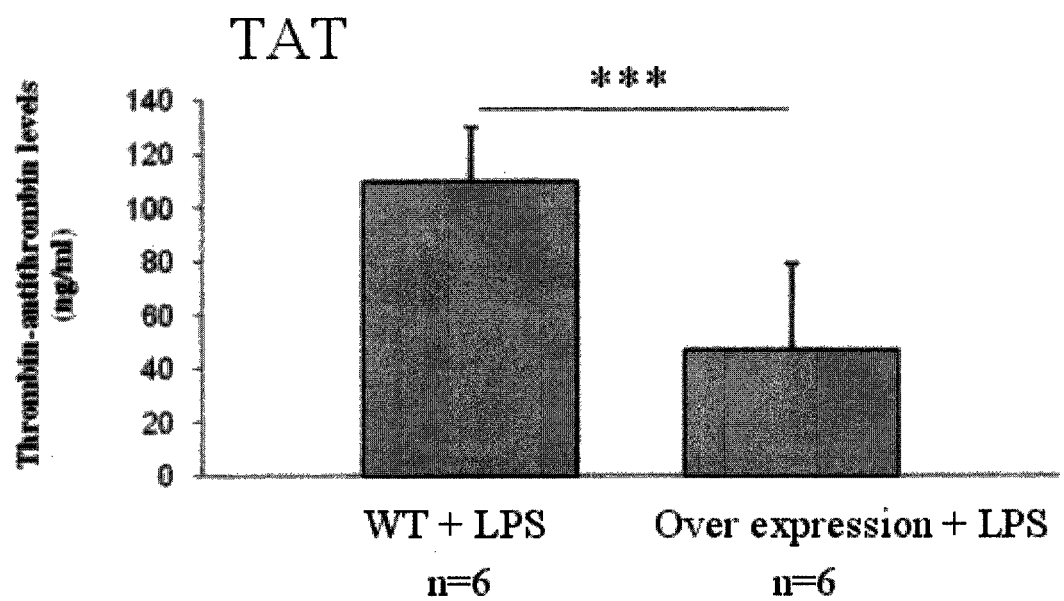

FIG. 21A. IL-6 levels.
FIG. 21B. Thrombin-antithrombin levels.

FIGS. 22A-22B

Heparanase Contributes to Coagulation Activation in Sepsis (2)

LPS was injected intra-peritoneal to heparanase knock-out (KO) mice compared to wild type mice (WT). Four hours later the blood was drawn and IL-6 (22A) and thrombin-antithrombin (TAT) (22B) were evaluated by ELISA. IL-6 and TAT were reduced in the KO mice compared to control ($p<0.005$), indicating reduced sepsis severity and decreased activation of the coagulation system.

Figure 22A:
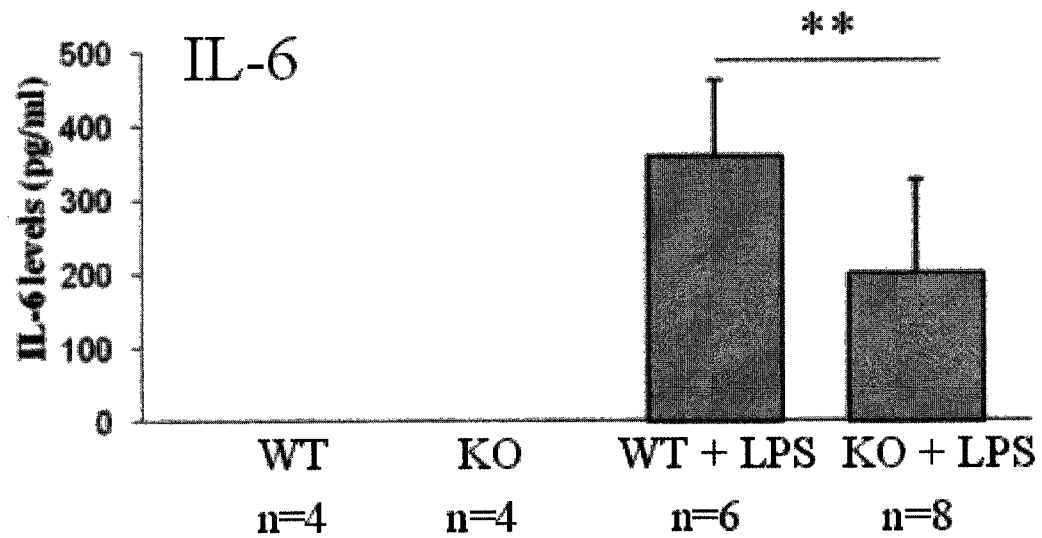
Figure 22B:
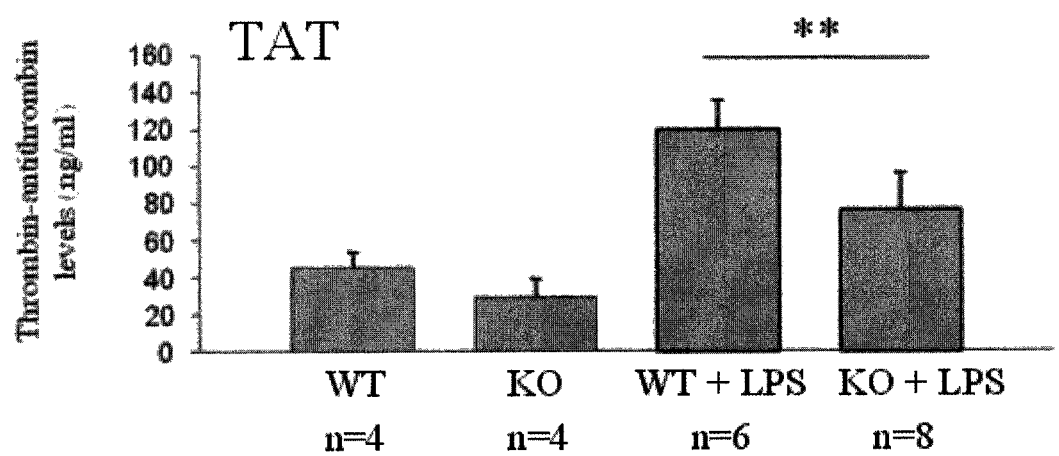

FIG. 22A. IL-6 levels.
FIG. 22B. Thrombin-antithrombin levels.

FIGS. 23A-23B

Inhibitors of TF—Heparanase Complex In-Vitro And In Vivo

Figure 23A:
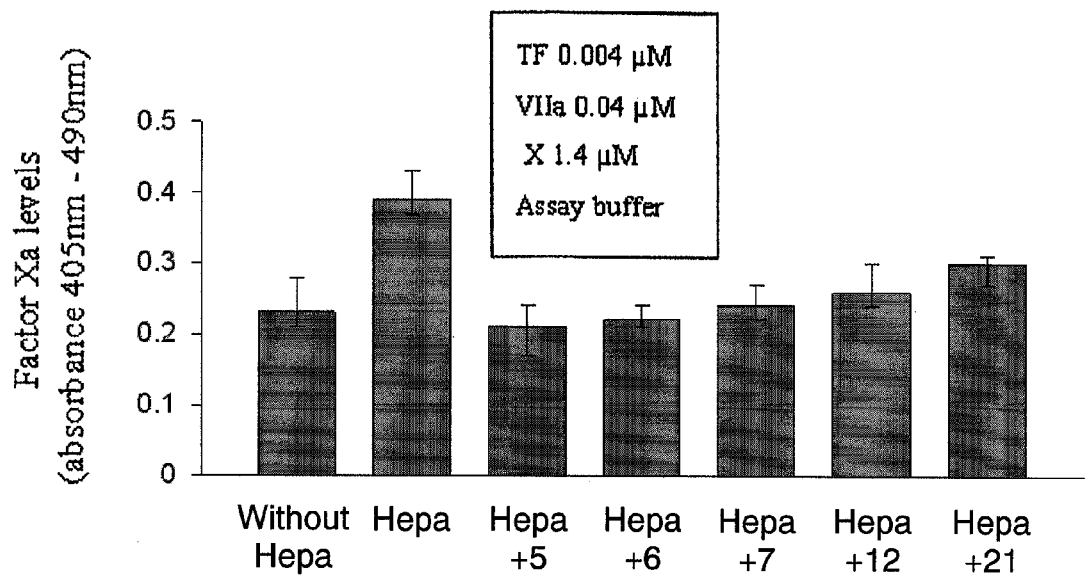

FIG. 23A. Factor Xa levels was evaluated by chromogenic substrate in an in-vitro assay including purified proteins of tissue factor (TF), factor VIIa, factor X and assay buffer. Addition of heparanase induced 2 folds increase in Xa level, while co-addition of TF/heparanase inhibitory peptides (5, 6, 7, 12, 21) abolished the procoagulant effect of heparanase.

Figure 23B:
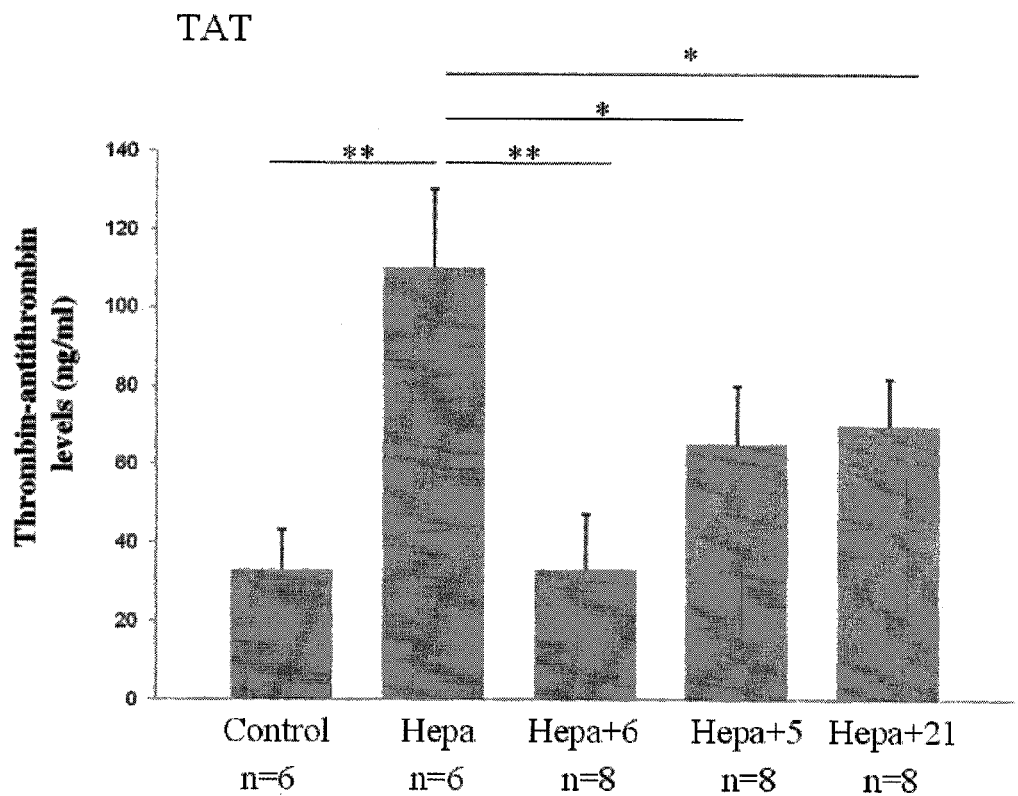

FIG. 23B. Heparanase was injected intra-peritoneal to ICR mice. Inhibitory peptides to TF/heparanase complex (number 5, 6, 21) were injected intra-peritoneal half an hour after heparanase. Four hours later the blood was drawn and Thrombin-antithrombin (TAT) level was measured by ELISA. Peptide 6 completely abolished the procoagulant effect of heparanase ($p<0.005$), while peptides 5 and 21 markedly decreased heparanase effect ($p<0.05$).

FIGS. 24A-24C

Heparanase Procoagulant Activity is Elevated in Women Taking Oral Contraceptives Plasma samples of 34 healthy women taking OC and 41 control women not on hormonal therapy were investigated. TF/heparanase complex activity, TF activity, heparanase procoagulant activity and factor Xa levels were studied using chromogenic substrate. Heparanase and thrombin-antithrombin (TAT) levels were analyzed by ELISA. TF/heparanase activity ($p<0.0001$), TF activity ($p<0.005$), heparanase procoagulant activity ($p<0.0001$) and factor Xa ($p<0.005$) were significantly higher in the OC group compared to the control group (24A). The most dramatic difference was observed in heparanase procoagulant activity, reaching a 3.3 fold increase ($p<0.0001$) and a 24% elevation in heparanase contribution to TF/heparanase complex. Levels of heparanase (24B) and TAT (24C) measured by ELISA did not statistically differ among the study groups.

Figure 24A:
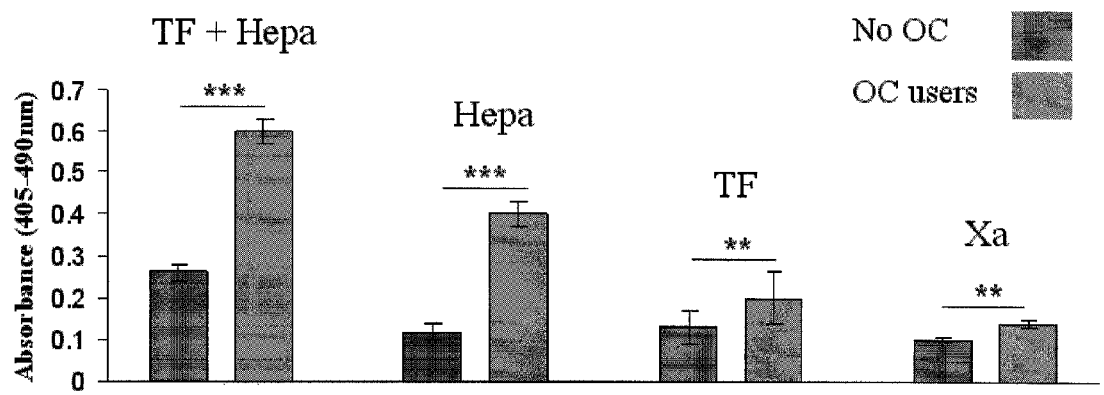
Figure 24B:
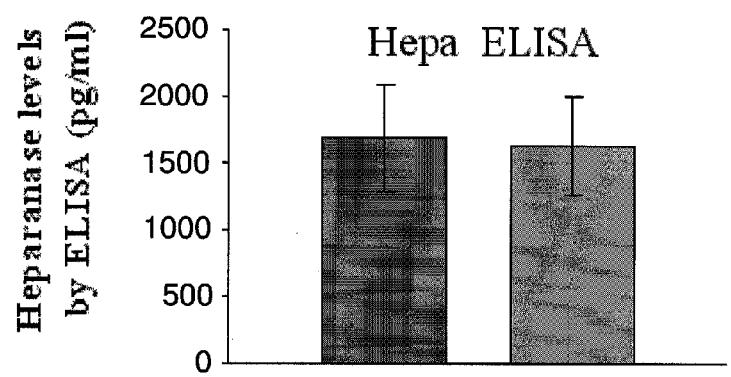
Figure 24C:
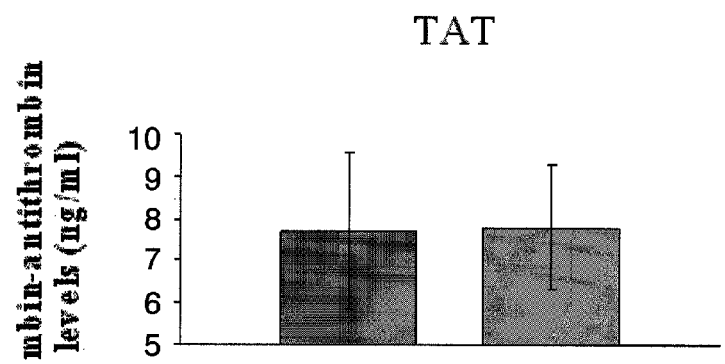

FIG. 24A. Heparanase, TF and Xa levels in oral contraceptive (OC) users and non users
FIG. 24B. Heparanase levels by ELISA.
FIG. 24C. Thrombin-antithrombin levels.

FIGS. 25A-25B

Heparanase Procoagulant Activity in Healthy Women

Figure 25A:
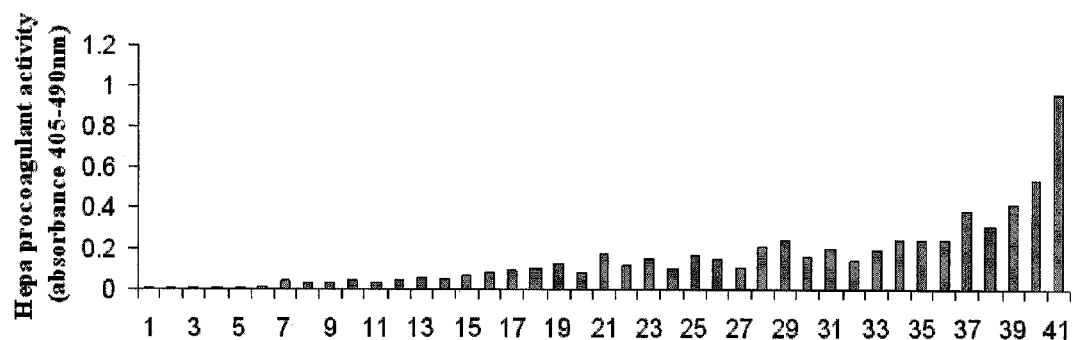
Figure 25B:
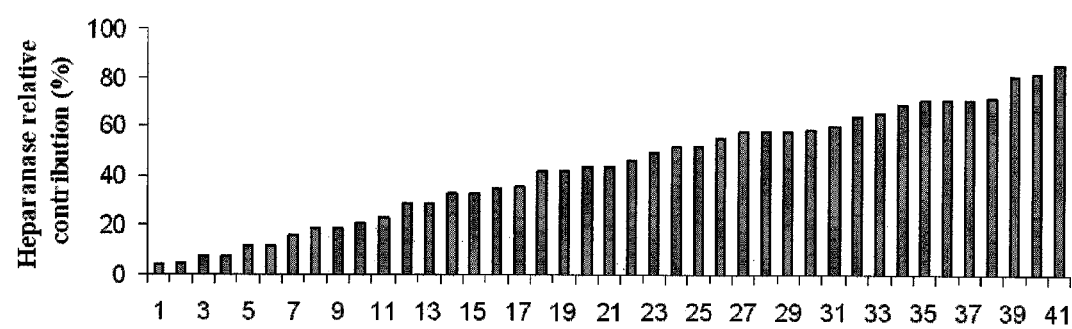

Plasma samples of 41 healthy women (age 26.4±0.5) not pregnant and not on hormonal therapy were investigated. Heparanase procoagulant activity (25A) and heparanase relative contribution to the complex (heparanase activity/TF+ heparanase activity) (25B) were studied using chromogenic substrate to Xa level. FIGS. 25A and 25B demonstrate results of the normal distribution in healthy young women.

FIG. 25A. Heparanase procoagulant activity.
FIG. 25B. Heparanase relative contribution.
No oral contraceptive or other medications

DETAILED DESCRIPTION OF THE INVENTION

Before explaining at least one embodiment of the invention in detail, it is to, be understood that the invention is not limited in its application to the details set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 4:
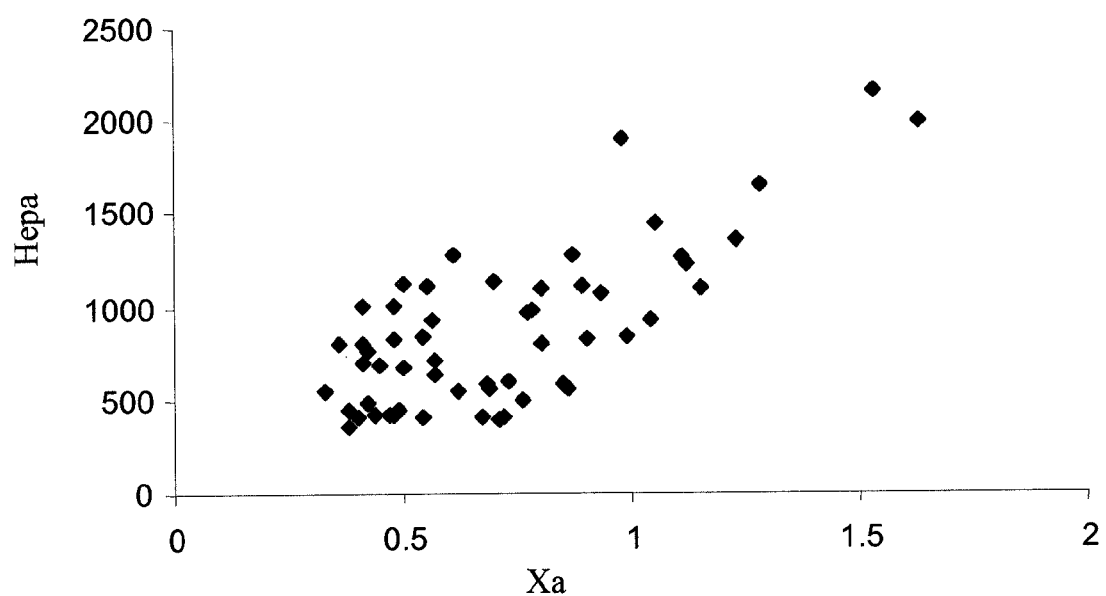

TF is the main initiator of blood coagulation. The results presented by the invention indicate that heparanase is an important cofactor to TF and thus heparanase is directly involved in activation of the coagulation cascade. The findings of the present invention are supported by basic experiments indicating that heparanase increases factor Xa levels in the presence of TF/VIIa complex. The generated Xa is in the same molecular weight of Xa cleaved by TF/VIIa and it is an active Xa as depicted by increased conversion of prothrombin to thrombin (FIG. 1B and FIG. 1D, respectively). Heparanase preparation was shown not to be contaminated with the relevant coagulation factors (FIG. 1E) and was not able to activate factor X or prothrombin directly. This novel mechanism was shown to be relevant in clinical practice. In addition to heparanase ability to increase Xa levels in normal human plasma (FIG. 2), a statistically significant positive correlation between heparanase plasma levels and Xa plasma levels, was found in patients with acute leukemia and healthy controls (FIG. 4). The invention now specifies heparanase mechanism of interaction by showing that heparanase increase TF activity rather than VIIa activity (FIGS. 5A-5B) and that there is a direct protein-protein interaction between TF and heparanase as illustrated by the co-IP and far-western blot methods (FIGS. 7A-7B). UFH was shown to completely abolish heparanase procoagulant activity (FIG. 6A) and the mechanism suggested is the disruption of the TF-heparanase interaction as was demonstrated by the co-IP study (FIGS. 7A-7B). This data widens the understanding of heparins anticoagulant activity; UFH enhances anti-thrombin activity but also inhibits heparanase procoagulant effect. Interestingly, a direct anti-Xa derivative (Rivaroxaban) was also found to abolish the procoagulant effect of heparanase (FIG. 6C). Given the multiple pathologic clinical situations that heparanase is involved in, the ability to completely inhibit heparanase haemostatic effect positions the direct anti-Xa derivatives as potential strong inhibitors in proangiogenic and prometastatic states. TFPI and TFPI-2 attenuated the effect of heparanase but even at high doses were not able to abolish heparanase effect (FIG. 6B). Notably, TFPI-2 was a stronger inhibitor than TFPI in the presence of heparanase. Taking into a count the high levels of heparanase and TFPI-2 in the placenta [Parish (2001) ibid.; Vlodaysky (2001) ibid.; Udagawa, K. et al. Placenta 23:145-153 (2002)], a potential regulatory role in placental hemostasis may be suggested.

The majority of TF resides in various intracellular compartments, predominantly in the Golgi. TF at the cell surface is localized in cholesterol-rich lipid rafts and extensively colocalized with caveolin-1 [Mandal, S. K. et al. Blood 107: 4746-4753 (2006)]. Recently it was found that heparanase induces Akt phosphorylation via a lipid raft receptor suggesting that lipid raft-resident receptor mediates heparanase signaling [Ben-Zaken, O. et al. Biochem. Biophys. Res. Commun. 361:829-834 (2007)]. It is possible that TF which is a transmembrane receptor concentrated in the lipid rafts interact with heparanase at the cell surface and in addition to enhancing coagulation also induces intracellular signaling.

The extent of TF protein induction in vascular cells does not always correlate well with TF activity [Steffel, J. et al. Circulation 112:341-349 (2005); Camera, M. et al. Arterioscler. Thromb. Vasc. Biol. 19:531-537 (1999)]. One possible explanation is the concomitant secretion of TFPI, the endogenous inhibitor of TF. Another possible reason is the distribution of TF in several cellular compartments. Biologically active TF is indeed located at the cell surface, whereas intracellular TF constitutes a pool that is only released upon cell damage [Camera (1999) ibid.; Schecter, A. D. et al. J. Clin. Invest. 100:2276-2285 (1997)]. Discrepancies between TF protein expression and activity can further be accounted for by the induction of a functionally inactive form of TF at the cell surface, termed latent or encrypted tissue factor. Expression of encrypted TF enables a cell to rapidly increase TF activity in response to certain stimuli without the need for de novo protein synthesis. De-encryption of TF has been observed secondary to changes in intracellular calcium levels, alterations in membrane phosphatidylserine expression, or modifications in the quaternary structure of TF [Wolberg, A. S. et al. Blood Coagul Fibrinolysis 10:201-210 (1999)]. Hence, the relative contribution of TF protein induction, cellular localization, and structural modification appears to determine the net procoagulant effect elicited by a given mediator. In view of the inventors new data it is possible that the procoagulant effect of TF also depends on the presence and level of its cofactor-heparanase.

Platelets are main contributors to thrombus formation. In view of heparanase abundance in platelets, elevated levels of heparanase generated locally upon degranulation of platelets [Vlodaysky, I. et al. Invasion Metastasis 12:112-127 (1992)] may further facilitate blood coagulation. Previously it was demonstrated that secretion of active heparanase from malignant cells was observed upon cell stimulation with physiological concentrations of adenosine, ADP, and ATP [Shafat, I. et al. J. Biol. Chem. 281:23804-23811 (2006)]. Although activated platelets secret ADP and ATP from α-granules, and thus may contribute to heparanase secretion from tumor cells, the specific mechanism involved in heparanase degranulation from platelets is not yet defined.

Overall, the results of the present invention support the notion that heparanase is a modulator of blood hemostasis, and suggest a novel mechanism by which heparanase is involved in direct activation of the coagulation cascade. Previous findings regarding the regulation of TF [Nadir (2006) ibid.] and TFPI [Nadir (2008) ibid.] serve as the base for a more fundamental role of heparanase in coagulation. The elevation of heparanase levels in human tumors together with the pro-thrombotic state of most neoplasms, suggest a possible clinical relevance of the procoagulant function of heparanase, as was demonstrated for leukemia patients (FIG. 4). Targeting domains of heparanase that mediate its enzymatic-dependent and independent activity functions may prove beneficial for patients with cancer and pro-thrombotic conditions.

In a first aspect, the present invention provides a composition comprising a combination of at least one heparanase molecule, any fragments, derivative or peptides thereof and at least one tissue factor (TF) molecule, any fragments, derivatives or peptides thereof, said composition optionally further comprising at least one additional therapeutic agent and pharmaceutically acceptable carrier, diluent, excipient and/or additive.

According to one embodiment, the heparanase used for the combined composition of the invention comprises both 50 KD and 8 KD subunits of heparanase forming the active molecule. According to another embodiment, the heparanase used for the combined composition of the invention may be a human heparanase molecule comprising the amino acid sequence as denoted by GenBank Accession No. AF144325. According to another embodiment, a fragment or peptide of heparanase used for the combined composition of the invention comprises the TF binding site within the heparanase molecule, which site mediates the interaction between heparanase and TF.

As referred to herein, the terms "active molecule" or "active compound" relate to a molecule capable of performing a biological function, the function being determined according to the context. For example, heparanase is referred to as the active molecule in such places where the combination of the 50 KD and 8 KD subunits of heparanase impart a pro-coagulatory effect, or when any other fragments of said heparanase impart the same effect. In other places, reference to heparanase as an active molecule relate to its capacity as a co-factor enhancing TF activity.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. "Amino acid analogs" refers to compounds that have the same fundamental chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission. With respect to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologues, and alleles of the invention.

For example, substitutions may be made wherein an aliphatic amino acid (G, A, I, L, or V) is substituted with another member of the group, or substitution such as the substitution of one polar residue for another, such as arginine for lysine, glutamic for aspartic acid, or glutamine for asparagine. Each of the following eight groups contains other exemplary amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M).

"Homology" with respect to a native heparanase polypeptide and its functional derivative, is defined herein as the percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Neither N- nor C-terminal extensions nor insertions shall be construed as reducing identity or homology. Methods and computer programs for the alignment are well known.

By "functional fragments" is meant "fragments", "variants", "analogs" or "derivatives" of the molecule. A "fragment" of a molecule, such as any of the amino acid sequence of heparanase, TF, or any mutants thereof used by the present invention is meant to refer to any amino acid subset of the molecule, including The TF binding site within the heparanase molecule or the heparanase binding site within the TF molecule, respectively. A "variant" of such molecule is meant to refer to a naturally occurring molecule substantially similar to either the entire molecule or a fragment thereof. An "analog" of a molecule is a homologous molecule from the same species or from different species. By "functional" is meant having same biological function, for example, required for said interaction.

More specifically, the terms "analogs" and "derivatives" as used herein mean heparanase, TF molecules or inhibitory peptides, with any insertions, deletions, substitutions and modifications to the molecule that do not interfere with the ability of said molecules to interact with each other and thereby enhance the pro-coagulating activity (hereafter referred to as "derivative/s"). A derivative should maintain a minimal homology to the amino acid sequence comprised within said molecules, e.g. between 20 to 90%, or between 40 to 75%, or in some cases less than 30%. It should be appreciated that by the term "insertions" as used herein is meant any addition of amino acid residues to the protein molecules of the invention or any fragments thereof, between 1 to 50 amino acid residues, specifically, between 20 to 1 amino acid residues and more specifically, between 1 to 10 amino acid residues, particularly any one of 1, 2, 3, 4, 5, 6, 7, 8, 9 and 10 amino acid residues.

As used herein, the term "mutant" means any heritable variation from the wild-type heparanase sequence that is the result of a mutation, e.g., single nucleotide polymorphism, deletion, insertion or truncation.

In one embodiment, the combined composition of the invention may be particularly applicable for modulating a coagulation process in a subject in need thereof.

Modulation, as referred to herein, relates to the imparting of an effect, including an induction, an increase, attenuation, a decrease, activation, inhibition, prevention or any other effect that changes the present state.

In another embodiment of the composition of the invention, modulation of a coagulation process may lead to activation of a pro-coagulation cascade in the treated subject.

The term "activation" as referred to herein, relates to the stimulation of a process or the induction of an increase in its rate by any one of about 1% to 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%.

Similarly, the terms "induction" and "increase" relate to the augmentation or amplification of a process or quantity, by any one of about 1% to 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%.

In yet another embodiment, the combined composition of the invention may further lead to attenuation and inhibition of an anti-coagulation process in a subject in need thereof.

The term "attenuation", as referred to herein, relates to a decrease or a reduction in value, amount, or rate. A decrease or a reduction as referred to herein, relate to the a reduction or lessening of a process or quantity by any one of about 1% to 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%.

The term "inhibition" as referred to herein, relates to the retardation, retraining or reduction of a process by any one of about 1% to 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%.

More specifically, the combined composition of the invention may lead to an increase in the serum levels of at least one of factor Xa and thrombin, in a subject in need thereof, thereby activating a pro-coagulation activity in said subject. More particularly, the combined composition of the invention enhances factor Xa generation, thereby promoting the pro-coagulation activity. More particularly, factor Xa catalyzes the conversion of prothrombin to thrombin, thereby leading to fibrin formation, platelets activation and generation of a thrombus in the treated subject.

It should be specifically appreciated that according to another embodiment, the combined composition of the invention is particularly applicable for treating a subject suffering of a coagulation-related pathologic condition.

Disclosed herein is a therapeutic combination that contains at least one therapeutically active form of heparanase and at least one therapeutically active form of TF and optionally at least one additional other therapeutic agent. The additional therapeutic agent may be capable of addressing at least one coagulation-related abnormality. Moreover, it should be noted that different combinations of different ratios at different concentrations of heparanase and TF may be used for different disorders.

Thus, it should be further appreciated that in certain embodiments the combined composition of the invention may further comprise at least one therapeutic agent, for example, a coagulation agent such as the factor VIIa molecule.

Thus, in an even further embodiment, the composition of the invention is for the treatment, amelioration and prevention of a coagulation-related pathologic condition in a subject in need thereof. More particularly, a coagulation disorder associated with impaired or reduced coagulation activity. As referred to herein, such coagulation-related pathologic condition may be for example Haemophilia or any other acquired or inherited deficiency of at least one coagulation factor such as Factor VIII, IX, or XIII.

The term "amelioration" as referred to herein, relates to a decrease in the intensity of a subject's symptoms due to a disease or condition. More specifically, "amelioration" relates to an improvement in a subject's coagulation properties. For instance, as a non-limiting example, the symptoms of a subject suffering from haemophilia are ameliorated by the pro-coagulative treatment with the composition of the invention.

More specifically, deficiencies in coagulation factors may be acquired (due to other diseases) or inherited, mild or severe, permanent or temporary. Those that are inherited are rare and tend to involve only one factor, which may be reduced or absent. Hemophilia A and B are the most common examples of inherited disorders. They are X-linked deficiencies of factors VIII and IX that occur almost exclusively in men (women are usually carriers who are asymptomatic or have mild bleeding). Other inherited factor deficiencies, not associated with the X chromosome, are found equally in both men and women.

The severity of symptoms experienced by a patient with an inherited factor deficiency depends on the factor involved and amount available. Symptoms may vary from episode to episode, from excessive bleeding after dental procedures to severe recurrent bleeding into joints or muscles. Patients with a modest reduction in coagulation factor level may experience few symptoms and may discover their deficiency as an adult—after a surgical procedure or trauma or during screening that includes a Prothrombin Time (PT) or Partial Thromboplastin Time (PTT) test. Those with severe factor deficiencies may have their first bleeding episode very early; for example, a male infant with a deficiency of Factor VIII, IX, or XIII may bleed excessively after circumcision.

Acquired deficiencies may be due to chronic diseases, such as liver disease or cancer; to an acute condition such as disseminated intravascular coagulation (DIC), which uses up clotting factors at a rapid rate; or to a deficiency in vitamin K or treatment with a vitamin K antagonist like warfarin (the production of factors II, VII, IX, and X require vitamin K). If more than one clotting factor is decreased, it is usually due to an acquired condition. Factors may be decreased as a reason of at least one of: consumption due to extensive clotting, liver disease, Uremia, some cancers, bone marrow disorders, exposure to snake venom, vitamin K deficiency, anticoagulation therapy, accidental ingestion of the anticoagulant warfarin, multiple blood transfusions (stored units of blood lose some of their clotting factors). Elevated levels of several factors are seen in situations of acute illness, stress, or inflammation. Some patients have persistent elevations of factor VIII that may be associated with an increased risk of venous thrombosis.

In another aspect, the invention provides a pharmaceutical composition for treating, preventing or ameliorating a coagulation-related pathologic condition in a subject in need thereof, said composition comprising as active ingredient a therapeutically effective amount of a combination of at least one heparanase molecule and any fragments, derivative or peptides thereof and at least one tissue factor (TF) molecule and any fragments, derivatives or peptides thereof. The combined composition of the invention optionally further comprises at least one additional therapeutic agent and at least one of a pharmaceutically acceptable carrier, diluent, excipient or additive.

It should be noted that the pharmaceutical composition of the invention may comprise the active compound in free form and be administered directly to the subject to be treated. Alternatively, depending on the size of the active molecule, it may be desirable to conjugate it to a carrier prior to administration. Therapeutic formulations may be administered in any conventional dosage formulation. Formulations typically comprise at least one active ingredient, as defined above, together with one or more acceptable carriers thereof.

Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intraperitoneal (IP), intravenous (IV) and intradermal) administration.

The pharmaceutical forms suitable for injection use include sterile aqueous solutions or dispersions and sterile powders for the extemporaneous preparation of sterile injectable solutions or dispersions. In all cases the form must be sterile and must be fluid to the extent that easy syringeability exists. It must be stable under the conditions of manufacture and storage and must be preserved against the contaminating action of microorganisms, such as bacteria and fungi.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above.

In the case of sterile powders for the preparation of the sterile injectable solutions, the preferred method of preparation are vacuum-drying and freeze drying techniques which yield a powder of the active ingredient plus any additional desired ingredient from a previously sterile-filtered solution thereof.

The pharmaceutical compositions of the invention generally comprise a buffering agent, an agent who adjusts the osmolarity thereof, and optionally, one or more pharmaceutically acceptable carriers, excipients and/or additives as known in the art. Supplementary active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

As used herein "pharmaceutically acceptable carrier" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

The pharmaceutical compositions of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers. The pharmaceutical compositions of the present invention also include, but are not limited to, emulsions and liposome-containing formulations.

The nature, availability and sources, and the administration of all such compounds including the effective amounts necessary to produce desirable effects in a subject are well known in the art and need not be further described herein. The preparation of pharmaceutical compositions is well known to the skilled man of the art and has been described in many articles and textbooks, see e.g., Remington's Pharmaceutical Sciences, Gennaro A. R. ed., Mack Publishing Co., Easton, Pa., 1990, and especially pp. 1521-1712 therein.

In yet another aspect, the present invention provides a method for the activation of a pro-coagulation process in a subject in need thereof. The method of the invention comprises the step of administrating to the subject a therapeutically effective amount of a combination of at least one heparanase molecule and any fragments, derivative or peptides thereof and at least one tissue factor (TF) molecule and any fragments, derivatives or peptides thereof, or any composition comprising the same, as described by the invention.

In a further aspect, the present invention provides a method for the treatment, amelioration and prevention of a coagulation-related pathologic condition. The method of the invention comprises the step of administering to a subject in need thereof an effective amount of a combination of at least one heparanase molecule and any fragments, derivative or peptides thereof and at least one tissue factor (TF) molecule and any fragments, derivatives or peptides thereof, or any composition comprising the same. The combined composition may optionally further comprise at least one additional therapeutic agent and pharmaceutically acceptable carrier, diluent, excipient and/or additive.

According to a specific embodiment, the methods and uses described by the invention are particularly applicable for treating coagulation-related disorders connected to impaired, reduced or deficient coagulation activity. Such disorders may be for example Haemophilia, acquired or inherited deficiency of at least one of the coagulation factors such as: VIII, IX, or XIII, wherein said deficiency may be caused by at least one of vitamin K dependent factor deficiency, liver disease, uremia, proliferative disorders, and uncontrolled bleeding caused by anticoagulation therapy, trauma, surgery, delivery and disseminated intravascular coagulation (DIC).

According to one embodiment, the method of the invention may be used for the treatment of a subject suffering of Haemophilia. More specifically, Haemophilia (also spelled as hemophilia in North America, from the Greek haima "blood" and philia "friend") is a group of hereditary genetic disorders that impair the body's ability to control blood clotting or coagulation, which is used to stop bleeding when a blood vessel is broken. In its most common form, Haemophilia A, clotting factor VIII is reduced. In Haemophilia B, factor IX is deficient. Haemophilia A occurs in about 1 in 5,000-10,000 male births, while Haemophilia B occurs at about 1 in about 20,000-34,000. The effects of this sex-linked, X chromosome disorder are manifested almost entirely in males, and females are almost exclusively carriers of the disorder. Bleeding is increased, especially into muscles, joints, or bleeding into closed spaces. Major complications include hemarthrosis and gastrointestinal bleeding).

In yet another embodiment, the method of the invention is applicable in the treatment of DIC. DIC, also known as consumptive coagulopathy, is a pathological activation of coagulation (blood clotting) mechanisms that happens in response to a variety of diseases. As its name suggests, it leads to the formation of small blood clots inside the blood vessels throughout the body. As the small clots consume all the available coagulation proteins and platelets, normal coagulation is disrupted and abnormal bleeding occurs from the skin (e.g. from sites where blood samples were taken), the digestive tract, the respiratory tract and surgical wounds. The small clots also disrupt normal blood flow to organs (such as the kidneys), which may malfunction as a result. DIC can occur acutely but also on a slower, chronic basis, depending on the underlying problem.

It should be noted that the invention further encompasses methods using the combined composition of the invention of treating coagulation-related disorders caused by anticoagulant treatment, for example, with heparinoids or "heparin-like molecules". The term heparin-like molecule as used herein refers to a molecule that possesses anti-coagulant activity and chemical structure sufficiently similar to that of heparin such that said molecule is considered as a possible alternate therapy to a patient requiring heparin. A heparin-like molecule includes, but is not limited to, a low molecular weight heparin, a heparin analogue, and the like. However, due to their potency, heparin and LMWH suffer drawbacks. Their major drawback is increased bleeding which can be life threatening. Moreover, approximately 5% (range up to 30%) of patients treated with heparin develop immune-mediated thrombocytopenia (HIT) which may be complicated by arterial and venous thrombosis due to intravascular platelet clumping.

As used herein by the methods of the invention, the term "pathologic condition", or "condition", refers to a condition in which there is a disturbance of normal functioning. Such condition is any abnormal condition of the body or mind that causes discomfort, dysfunction, or distress to the person affected or those in contact with the person. Sometimes the term is used broadly to include injuries, disabilities, syndromes, symptoms, deviant behaviors, and atypical variations of structure and function, while in other contexts these may be considered distinguishable categories. It should be noted that the terms "disease", "disorder", "condition" and "illness", are equally used herein.

By "patient" or "subject in need" it is meant any mammal who may be affected by the above-mentioned conditions, and to whom the treatment methods herein described is desired, including human, bovine, equine, canine, murine and feline subjects. Preferably said patient is a human. It should be noted that administering of the drug combination of the invention to the patient includes both self-administration and administration to the patient by another person.

According to another specific embodiment, the active ingredients or compositions comprising the same or combination thereof used by the method of the invention may be administered via any mode of administration. For example, oral, intravenous, intramuscular, subcutaneous, intraperitoneal, parenteral, transdermal, intravaginal, intranasal, mucosal, sublingual, topical, rectal or subcutaneous administration, or any combination thereof.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician.

In yet a further aspect, the present invention provides the use of a therapeutically effective amount of a combination of at least one heparanase molecule and any fragments, derivative or peptides thereof and at least one tissue factor (TF) molecule and any fragments, derivatives or peptides thereof, in the preparation of a medicament for the treatment of a coagulation-related pathologic condition.

The invention further provides a pharmaceutical unit dosage form comprising at least one heparanase molecule and any fragments, derivative or peptides thereof and at least one tissue factor (TF) molecule and any fragments, derivative or peptides thereof, and a pharmaceutically acceptable carrier or diluent.

The present invention therefore particularly relates to safe, non-interfering, additive or synergistic combinations of heparanase and TF, or of pharmaceutically acceptable salts thereof, whereby those additive and synergistic combinations are useful in treating subjects suffering from a coagulation-related pathologic disorder having undesired impaired coagulation activity. The non-interfering, synergistic and additive compositions of the invention may also be used for the treatment of subjects presenting with symptoms or signs of such disorders.

By synergic combination is meant that the effect of both heparanase and TF is greater than the sum of the therapeutic effects of administration of any of these compounds separately, as a sole treatment.

The combined compounds of the present invention are generally administered in the form of a pharmaceutical composition comprising both compounds of this invention together with a pharmaceutically acceptable carrier or diluent, and optionally a further therapeutic agent. Thus, the compounds used by this invention can be administered either individually in a kit or together in any conventional dosage form.

More particularly, since the present invention relates to the treatment of diseases and conditions with a combination of active ingredients which may be administered separately, the invention also relates as a further aspect, to combining separate pharmaceutical compositions in kit form. The kit includes two separate pharmaceutical compositions:
(a) at least one of any heparanase molecule, or any pharmaceutically acceptable fragments, derivatives, peptides thereof, and a pharmaceutically acceptable carrier or diluent, optionally, in a first unit dosage form.

(b) at least one TF molecule, any pharmaceutically acceptable fragments, derivatives, peptides thereof and a pharmaceutically acceptable carrier or diluent, optionally, in a second unit dosage form.

The kit of the invention further includes container means for containing both separate compositions; such as a divided bottle or a divided foil packet however, the separate compositions may also be contained within a single, undivided container. Typically the kit includes directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

According to one embodiment the kit of the invention is intended for achieving a therapeutic effect in a subject suffering from a coagulation-related pathologic disorder connected to impaired, reduced or deficient coagulation activity. Such disorders may be for example Haemophilia, acquired or inherited deficiency of at least one of the coagulation factors such as: VIII, IX, or XIII, wherein said deficiency may be caused by at least one of vitamin K dependent factor deficiency, liver disease, uremia, proliferative disorders, and uncontrolled bleeding caused by anticoagulation therapy, trauma, surgery, delivery and disseminated intravascular coagulation (DIC). Achieving a therapeutic effect is meant for example, preventing or slowing the progression of coagulation-related condition.

Still further, the invention provides a method of treatment of a pathologic disorder comprising the step of administering to a subject in need thereof a therapeutically effective amount of a first and a second unit dosage forms comprised in the kit according to the invention.

It should be appreciated that both components of the kit, the heparanase in the first dosage form and the TF molecule in the second dosage form may be administered simultaneously.

Alternatively, said first compound or dosage form and said second compound or dosage form are administered sequentially in either order.

The invention further provides a method for preventing or reducing the risk of developing coagulation-related disease comprising the administration of a prophylactically effective amount of a first and a second unit dosage forms comprised in the kit of the invention, to a person at risk of developing coagulation related disease.

The term "prophylaxis" refers to prevention or reduction the risk of occurrence of the biological or medical event that is sought to be prevented in a tissue, a system, animal or human by a researcher, veterinarian, medical doctor or other clinician, and the term "prophylactically effective amount" is intended to mean that amount of a pharmaceutical composition that will achieve this goal.

The invention shows for the first time a direct interaction between the heparanase and the TF molecule. This interaction leads to activation of a pro-coagulation process as initiated by activation of factor Xa that catalyzes the conversion of prothrombin to thrombin, thereby leading to fibrin formation, platelets activation and generation of a thrombus in the treated subject. These results clearly demonstrate the role of the heparanase-TF interaction as a key element in this coagulation pathway, and therefore as a potential target for modulation of the coagulation process. The invention thus provides the use of the TF-heparanase complex as a target for searching coagulation-modulating compounds.

Thus, in another aspect, the present invention provides a screening method for a coagulation modulatory compound, wherein said compound binds the heparanase-TF binding site within any one of the heparanase molecule or the TF molecule, and modulates the interaction of heparanase and TF and thereby modulating the coagulation activity in a subject suffering from a coagulation-related disorder. According to one embodiment, the screening method of the invention comprising the steps of:

(a) obtaining a candidate compound which binds to any one of heparanase molecule or to any fragment, variant, derivative and mutant thereof or to TF molecule or to any fragment, variant, derivative and mutant thereof;

(b) selecting from the candidate compounds obtained in step (a) a compound that modulates the direct interaction between said TF and heparanase or to any fragment, variant, derivative and mutant thereof; and (c) determining the effect of the compound selected in step (b) on the heparanase-TF complex mediated pro-coagulation activity.

Key to the application of high-throughput screening for high-affinity binding of coagulation-modulating compounds to the heparanase or the TF molecules is the development of a sensitive and convenient screening assay.

More specifically, development of a robust screening assay for coagulation-modulating compounds through their affinity for heparanase or TF in the domain where the interaction between both occurs will be the first step in said screening method.

Therefore, the candidate coagulation-modulating compound may be obtained by the steps of: (a) providing a mixture comprising the heparanase molecule or any fragment, variant, derivative and mutant thereof or the TF molecule or any fragment, variant, derivative and mutant thereof; (b) contacting the mixture with a candidate compound under suitable conditions for said binding; and (c) determining the effect of the candidate compound on an end-point indication. It should be noted that modulation of the end point indicates the binding of the tested candidate compound to TF or heparanase.

According to one specific embodiment, the end point indication may be the binding of an anti-heparanase or TF antibody to the heparanase or TF molecules, respectively, which leads to a visually detectable signal. In such case, an increase in this end point is indicative of binding of said test compound to the heparanase or the TF molecule, respectively.

More particularly, each candidate compound, that may be for example a peptide or any small molecule, may be placed in a well and direct binding of the heparanase or the TF-molecule or any fragments thereof, is detected, preferably by an antibody specific for heparanase or TF, respectively. Conditions for effective binding of the heparanase or TF molecule or any fragments thereof to a candidate coagulation-modulating compound on the plate may be optimized involving study of pH, salt and buffer composition, and carrier proteins such as BSA. This robust screening yields compounds that bind to any one of the heparanase or TF molecules. Such compounds that bind to heparanase or TF are pooled and then assayed as described below.

In the second step of the screening method of the invention, the candidate coagulation-modulating compounds which bind either heparanase or TF, and were preferably obtained as described above, may be further selected for their ability to specifically bind heparanase or TF at the novel TF-heparanase binding site of the invention. Such selected compounds will desirably be capable of preventing or modulating the interaction between said heparanase and TF. According to this embodiment, the selection may be performed by the steps of: (a) providing a mixture comprising heparanase molecule or any fragment, variant, derivative and mutant thereof, or alternatively, TF molecule or any fragment, variant, derivative and mutant thereof; (b) contacting said mixture with the tested candidate compound under suitable conditions for specific binding of the heparanase-TF via the interaction, or binding site; and (c) determining the effect of the tested candidate compound on an end-point indication. Modulation of such end point is indicative of binding of the tested candidate compound to the heparanase or the TF molecules via said heparanase-TF binding site.

According to another embodiment, the mixture used for the selection stage of the screening method of the invention comprises: (a) heparanase molecule or any fragment, variant, derivative, homologue and mutant thereof; (b) a TF molecule which specifically binds to heparanase, via the TF binding site in heparanase; and (c) optionally solutions, buffers and compounds which provide suitable conditions for interaction of the heparanase molecule with the TF molecule and for the detection of an end-point indication for the interaction. According to one embodiment, the end point indication may be the binding of TF to heparanase, which leads to a visually detectable signal.

The term "homologue" as referred to herein, refers to any protein, gene encoding said protein or morphological structure that is similar in both amino-acid sequence and function between organisms or in a single organism. Said similarity of amino-acid sequence is of at least 50%, at least 60%, at least 70%, at least 80%, at least 90%, or at least 95%.

In a further embodiment of the invention, an inhibition observed in such end point indicates direct binding of the tested candidate compound to the TF binding site in heparanase. Accordingly, the binding of the candidate compound competes with the binding of the TF to the binding site and thereby modulates and/or inhibits said binding.

For performing this competition assay, the TF or heparanase molecules may be directly labeled, for example by biotinylation or by addition of fluorescein, or alternatively may be indirectly labeled by a specific anti-TF or anti-heparanase antibody.

The mixture used for obtaining and selecting candidate compounds by the screening method of the invention may be a cell mixture or a cell-free mixture.

According to one alternative embodiment, the mixture utilized by the method of the invention may be a cell-free mixture. Such mixture comprises the heparanase molecule or any functional fragment thereof (preferably, a fragment comprising the TF binding site), that may be provided as any one of a peptide, a purified recombinant protein, a fusion protein and a cell lysate or membrane preparation of a transformed host cell expressing the said heparanase molecule.

In a particular and non limiting example, such selection step of the screening method of the present invention may be performed, where heparanase is bound onto the wells of a microplate. Then, each well is incubated with a limiting amount of the TF molecule, in the presence of the candidate coagulation-modulating compound. Supernatant is collected from each well. Unbound TF is detected in the supernatant by the use of anti-TF specific antibody ELISA. Should the test compound bind tightly to heparanase in the domain recognized by the TF molecule, it will compete in the binding of TF to heparanase and release free TF that can be detected over a zero background, rendering the assay sensitive. Candidate compounds binding outside the domain involved in the heparanase/TF interaction will be eliminated by this approach.

An alternative approach is to use a labeled TF and assay for the ability of the candidate compounds to displace labeled TF from binding to heparanase on the plate.

Alternatively, the mixture utilized for the selection step by the method of the invention may be a cell mixture. In this particular embodiment, each candidate compound, for example a peptide is placed in a well and the well is then blocked with BSA or fetal calf serum. Binding of cells that express heparanase on is scored visually, or by anti-heparanase ELISA. Alternatively, cell membranes or other fractions prepared from the heparanase-expressing cells may be used, and binding is detected using anti-heparanase antibody. Positive candidate compounds are then re-examined in the presence of the TF molecule, as competitor.

It should be noted that the heparanase or TF molecules or any fragment thereof comprised in the mixture, may be provided as any one of a purified recombinant protein, and a cell lysate or membrane preparation of a transformed host cell expressing the heparanase or the TF molecules. The terms fragments and functional fragments used herein mean the heparanase, or TF molecules or any fragment thereof, with any insertions, deletions, substitutions and modifications, that include the TF or heparanase, respectively, binding site and is capable of binding to each other and thereby inducing specific activation of a pro-coagulation process (hereafter referred to as "fragment/s"), as reflected for example by elevation in factor Xa or thrombin levels.

According to another embodiment, the candidate compound examined by the screening method of the invention may be selected from the group consisting of: protein based, nucleic acid based, carbohydrates based, lipid based, natural organic based, synthetically derived organic based, inorganic based, and peptidomimetics based compounds.

According to another embodiment, the compound may be product of any one of positional scanning of combinatorial libraries of peptides, libraries of cyclic peptidomimetics, and random or dedicated phage display libraries.

According to another specific embodiment, the third stage of the screening method of the invention involves further evaluation of the feasibility of the selected candidate compounds to actually modulate the levels of thrombin or factor Xa and thereby, their ability to modulate coagulation process. Therefore, the selected candidate compounds are next evaluated for their ability to modulate elevation in Factor Xa levels. This evaluation stage involves the steps of: (a) providing a test system comprising heparanase and TF molecule or any fragment, variant, derivative, homologue and mutant thereof; (b) contacting the test system with a tested candidate compound obtained and selected by the previous stages of the screening method of the invention, under conditions suitable for interaction of heparanase with the TF molecule; and (c) determining the effect of the candidate compound on an end-point indication as compared to a control, wherein said effect is indicative of the ability of the tested candidate to modulate the direct interaction between said heparanase molecule and the TF molecule, which leads to modulating the levels of Factor Xa or thrombin.

The test system used for evaluating the candidate coagulation-modulating compound isolated by the screening method of the invention may be an in-vitro/ex-vivo cell culture, or an in-vivo animal model. Such test system optionally further comprises endogenous and/or exogenous compounds which provide suitable conditions for the TF-heparanase activation of factor Xa or thrombin and for the detection of an end-point indication for determining the modulatory effect of the candidate compound. More specifically, said activation or modulation is determined by the levels of thrombin or factor Xa.

The test system utilized by the screening method of the invention for evaluation may be an in-vitro/ex-vivo cell culture comprising an endogenously expressed heparanase molecule.

The end point indication in this particular test system may therefore be the TF-heparanase complex-induced elevation in the levels of either factor Xa or thrombin, which leads to a visually detectable signal. More specifically, using a chromogenic substrate of either factor Xa or thrombin, respectively. Thus, any modulation, inhibition or even reduction of said end point is indicative of the ability of the candidate compound to specifically modulate and probably inhibit the interaction of heparanase with the TF molecule. Such inhibition or modulation leads to modulation of the TF-heparanase-mediated activation of a pro-coagulation process, specifically, as reflected by elevation in factor Xa or thromin levels. The TF-heparanase-induced increase in factor Xa or thrombin levels may be detected, for example, by quantitative estimation of the product using a chromogenic substrate of these factors.

It should be noted that the test system used by the invention optionally further comprises endogenous and/or exogenous compounds which provide suitable conditions for activation of factor Xa or thrombin and for the detection of an end-point indication for determining the coagulation-modulatory effect of the candidate compound.

In another preferred embodiment, the modulation of factor Xa or thrombin activation may be any one of increasing or decreasing the activation or the levels of these factors as compared to a control.

In another aspect, the present invention provides a coagulation modulatory compound obtained by the method as described above, wherein said compound inhibits the direct interaction between heparanase and TF and thereby reduces the heparanase-TF complex mediated pro-coagulation activity. Such compounds may be therefore used for treating disorders associated with enhanced coagulation activity.

In an even further aspect, the present invention provides a pharmaceutical composition comprising a coagulation modulatory compound obtained by the method described above, said composition being for the treatment, amelioration and prevention of a coagulation-related disorder.

Thus, according to one embodiment, the composition of the invention may be specifically applicable for the treatment of conditions associated with increased coagulation activity, such thrombotic diseases may be for example, cardiovascular complications including unstable angina, acute myocardial infraction (heart attack), cerebral vascular accident (stroke), arterial thrombosis, arterial aneurisms, artherosclerosis, peripheral arterial disease, stent thrombosis, venous thrombosis, Antiphospholipid syndrome (APLA), Protein C deficiency and other thrombophilia, superficial thrombophlebitis or deep vein thrombosis (DVT), pulmonary embolism (PE), vascular gestational complications such as recurrent abortions, abruption placenta, intra uterine fetal death (IUFD) and severe preeclampsia, inflammation, malignancy and infectious processes.

In one embodiment, the invention provides a compound identified by the screening method of the invention for the treatment of a thrombotic disorder such as anti-phospholipid antibodies (APLA). APLA is a disorder of coagulation, which causes blood clots (thrombosis) in both arteries and veins, as well as pregnancy-related complications such as miscarriage, preterm delivery, or severe preeclampsia. The syndrome occurs due to the autoimmune production of antibodies against phospholipid (aPL), a cell membrane substance. In particular, the disease is characterised by antibodies against cardiolipin (anti-cardiolipin antibodies) and $\beta_2$ glycoprotein I.

The term "primary antiphospholipid syndrome" is used when APLA occurs in the absence of any other related disease. APLA is commonly seen in conjunction with other autoimmune diseases. The term "secondary antiphospholipid syndrome" is used when APLA coexists with other diseases such as systemic lupus erythematosus (SLE). In rare cases, APLA leads to rapid organ failure due to generalised thrombosis and a high risk of death.

In yet another embodiment, the compound identified by the screening method of the invention, inhibiting the TF-heparanase complex formation may be used for treating a thrombotic disorder such as anticardiolipin syndrome. The Anticardiolipin syndrome is characterized by recurrent venous or arterial thrombosis (clots), recurrent fetal loss, and thrombocytopenia (a reduction in the number of platelets) and can be either primary or secondary to other diseases such as lupus.

In another embodiment, the compound identified by the screening method of the invention, may be used for treating a thrombotic disorder caused by protein C deficiency. Protein C deficiency is a rare genetic trait that predisposes to thrombotic disease. It was first described in 1981. The disease belongs to a group of genetic disorders known as thrombophilias. The prevalence of protein C deficiency has been estimated to about 0.2% to 0.5% of the general population. Protein C deficiency is associated with an increased incidence of venous thromboembolism (relative risk 8-10). The main function of protein C is its anticoagulant property as an inhibitor of coagulation factors V and VIII.

According to another specific embodiment, the anti-coagulating compound obtained by the screening method of the invention may be applicable in conditions having an undesired increased coagulation activity, for example, cardiovascular complications including unstable angina, acute myocardial infraction (heart attack), cerebral vascular accident (stroke), arterial thrombosis, arterial aneurisms, artherosclerosis, peripheral arterial disease, stent thrombosis, venous thrombosis, Antiphospholipid syndrome (APLA), Protein C deficiency and other thrombophilia, superficial thrombophlebitis or deep vein thrombosis (DVT), pulmonary embolism (PE), vascular gestational complications such as recurrent abortions, abruption placenta, intra uterine fetal death (IUFD) and severe preeclampsia, inflammation, malignancy and infectious processes.

As used herein to describe the present invention, the terms "malignant proliferative disorder", "cancer", "tumor" and "malignancy" all relate equivalently to a hyperplasia of a tissue or organ. If the tissue is a part of the lymphatic or immune systems, malignant cells may include non-solid tumors of circulating cells. Malignancies of other tissues or organs may produce solid tumors. In general, the composition as well as the methods of the present invention may be used in the treatment of non-solid and solid tumors, for example, carcinoma, melanoma, leukemia, and lymphoma, that are associated with increased coagulation.

In yet another alternative embodiment, the coagulation-modulatory compound obtained by the screening method of the invention may modulates the direct interaction between heparanase and TF and thereby enhance the heparanase-TF complex mediated pro-coagulation activity. In such particular embodiment, the modulatory compound may be applicable for treating conditions associated with impaired coagulation activity, for example, Haemophilia, acquired or inherited deficiency of at least one of the coagulation factors such as: VIII, IX, or XIII, wherein said deficiency may be caused by at least one of vitamin K dependent factor deficiency, liver disease, uremia, proliferative disorders, and uncontrolled bleeding caused by anticoagulation therapy, trauma, surgery, delivery and disseminated intravascular coagulation (DIC).

According to another specific aspect, the invention provides the use of an inhibitor of the TF-heparanase complex for the treatment of coagulation-related disorders, particularly, disorders associated with increased coagulation. More specifically, the invention provides a method for the treatment of conditions associated with increased coagulation activity, comprising the step of administering to a subject in need thereof an inhibitor of TF-heparanase complex. Such inhibitor may be any compound interfering with said interaction. A non-limiting example for such inhibitors may be any one of anti-Xa derivative, TFPI, TFPI-2 and UFH in an amount effective for inhibiting the formation of said complex and thereby inhibiting the coagulation activity.

Still further, the invention provides the use of a compound that inhibits the interaction of heparanase and TF. Such compound may be, for example, any one of anti-Xa derivative, TFPI, TFPI-2 and UFH for the preparation of a composition for the treatment of coagulation-related disorders associated with increased coagulation activity. Such conditions may be for example, cardiovascular complications including unstable angina, acute myocardial infraction (heart attack), cerebral vascular accident (stroke), arterial thrombosis, arterial aneurisms, artherosclerosis, peripheral arterial disease, stent thrombosis, venous thrombosis, Antiphospholipid syndrome (APLA), Protein C deficiency and other thrombophilia, superficial thrombophlebitis or deep vein thrombosis (DVT), pulmonary embolism (PE), vascular gestational complications such as recurrent abortions, abruptio placenta, intra uterine fetal death (IUFD) and severe preeclampsia, inflammation, malignancy and infectious processes.

In a further aspect, the invention provides a method for determining heparanase procoagulant contribution to TF/factor VIIa activity in a biological sample obtained from a mammalian subject.

The method of the invention is of particular relevance for assessing the procoagulant role of heparanase in various medical conditions. In particular, the method can be employed to diagnose and/or monitor coagulation-related disorders in pregnant women or at delivery.

As known in the art, pregnancy is an acquired hypercoagulable state that increases as pregnancy advances and peaks at the puerperium. Women with a prior tendency to thrombosis may present with clinical symptoms of placental vascular complications. At present, maternal thrombophilia is believed to be responsible for placental vascular events, although 30-50% of vascular gestational pathologies cannot be accounted for by the current available tests for thrombophilia [Lanir N et al., Semin Thromb Hemost 2003, 29:175-84]. Thus, the need to understand the delicate haemostatic balance throughout pregnancy is essential.

As mentioned above, the inventors found out that heparanase serve as a cofactor of TF, implying that heparanase is directly involved in activation of the coagulation cascade in an enzymatically independent manner. The method of the invention is based on the presence of TF/heparanase complex and the ability of heparins or other inhibitors to completely abrogate the complex interaction.

The present invention demonstrates the ability to discriminate heparanase and TF procoagulant activities from the TF/heparanase complex, using purified proteins (FIGS. 9A-9C and 10A-10C). Analyzing fifty five plasma samples, heparanase procoagulant activity was more dominant in pregnant women compared to age matched non-pregnant controls (FIG. 12). Additionally, heparanase procoagulant relative contribution to the complex was significantly higher in all pregnant women compared to non-pregnant and with no difference in the casarian section (CS), vaginal or intrauterine growth restriction (IUGR) groups. Interestingly, heparanase procoagulant activity was higher in the CS group, representing late third trimester plasma haemostatic state, compared to normal vaginal delivery. This result may represent the real hemostatic balance similar to women with von Willebrand factor deficiency that may bleed following delivery due to dramatic reduction in factor VIII [Mannucci P M, Blood 2001; 97:1915-9]. Similarly, Xiong et al reported that maternal plasma levels of TFPI-2 in normal pregnant women compared with healthy non-pregnant women reached a maximum level at 39 weeks of gestation, and dramatically decreased to nearly a non-pregnant level on the first day of postpartum [Xiong Y et al, Thromb Res 2010; 125:e317-22]. Another possible explanation is a hypercoagulable state resulting in consumption coagulopathy and decreased plasma coagulation factors during delivery. Levels of heparanase by ELISA were statistically borderline lower in the CS patients and with no difference in the vaginal and IUGR patients compared to controls. One of the ELISA major limitations is the ability to detect mainly the active form of heparanase (50+8 kDa) and not the full-length heparanase (65 kDa) that the inventors discovered as being able to enhances TF activity too. Thus inability to measure actual total levels of plasma heparanase at present may possibly explain the discrepancy between heparanase levels and its procoagulant activity. Lack of correlation between heparanase procoagulant assay compared to Xa and thrombin levels (FIG. 13) can be explained by contributing factors to activation of the coagulation system during pregnancy such as elevated levels of factor VIII and reduced protein S activity [Mahieu B et al., Blood Coagul Fibrinolysis 2007, 18:685-8; Walker M C et al., Am J Obstet Gynecol 1997; 177:162-9]. Thus, factor Xa and thrombin levels reflect common final coagulation pathways. No difference was found in antithrombin activity between cases (FIG. 13) in accordance with recently published data by Szecsi et al [Szecsi P B et al., Thromb Haemost 2010, 103:718-27] and strengthening the ability of the assay to evaluate heparanase procoagulant activity. Although TFPI levels were decreased in pregnant compared to non-pregnant women, the difference was not statistically significant. According to Boer at al. TFPI activity in plasma of women 1-2 hours post delivery was not different from that in late third trimester [Boer K et al., J Thromb Haemost 2007; 5:2415-20], supporting the present findings regarding levels of free TFPI in the study groups (FIG. 13). Overall, although prominent differences exist in TF activity, heparanase by ELISA, factor Xa and thrombin levels among the groups (FIGS. 12 and 13), differences in heparanase activity and relative contribution to the complex are much more dramatic (FIG. 12). The present data may indicate on a major role of heparanase in the hemostasis of delivery and a good ability of the suggested assay to measure the changes.

Placental involvement of heparanase was recently described. Presence of heparanase in normal and abnormal placentas and in a variety of trophoblast subpopulations with different invasive potential was demonstrated [Haimov-Kochman R et al., Mol Hum Reprod 2002, 8:566-7; Dempsey L A e al., Glycobiology 2000; 10:467-75]. In a previous work of the inventors using immunostaining and RT-PCR, levels of heparanase were higher in placentas of vaginal and IUGR deliveries compared to levels in placentas of CS deliveries in maternal as well as in fetal placenta elements [Nadir Y et al., Thromb Res 2010; 126:e444-50]. These previous placental findings support the suggested consumption coagulopathy mechanism occurring in plasma during vaginal and IUGR deliveries and implies to placental source of heparanase in the plasma. Further placental analysis of heparanase levels in complicated pregnancies may be a way to better elucidate these pathologies, which might have hypothetically been caused by a change in the haemostatic system due to heparanase induction.

The extent of TF protein induction in vascular cells does not always correlate with TF activity [Steffel J et al., Circulation, 2005, 112:341-9; Camera M et al., Arterioscler Thromb Vasc Biol 1999, 19:531-7]. A possible explanation is the concomitant secretion of TFPI, the endogenous inhibitor of TF. Another possible reason is cellular localization and structural modification that appear to determine the net procoagulant effect elicited by a given mediator [Camera M. et al., Arterioscler Thromb Vasc, Biol 1999, 19:531-7; Schecter A D et al., J Clin Invest 1997, 100:2276-85; Wolberg A S et al., Blood Coagul Fibrinolysis 1999, 10:201-10]. The present finding of the presence of TF/heparanase complex and the ability to quantify the relative contribution of heparanase to the complex widen our understanding on the factors affecting TF activity in different clinical setups.

Various heparin derivatives have been tested by the inventors in the heparanase procoagulant kit of the invention. Limitation of all derivatives was turbidity formed in the presence of plasma and the chromogenic substrate. With fondaparinux, possibly due to its low molecular weight (~1.5 kDa), at concentration of 2.5 µg/ml, the assay remains clear without obscuring turbidity. Heparins are strong inhibitors of heparanase, although they are not specific inhibitors and exert multiple interactions with other molecules [Vlodaysky I et al., Thromb Res 2007; 120(Suppl 2):S112-20]. Although heparins effect on plasma anti-thrombin can be regarded in the assay as a constant, developing specific inhibitors to heparanase or to TF/heparanase complex may reveal superior. The assay of the present invention is easy to perform, results are available in a short time and are reproducible. Except heparanase ELISA, no other acceptable assays to measure heparanase in plasma exist. The main strength of the assay of the invention is its ability to assess the relative contribution of heparanase to the TF/heparanase complex.

Therefore, another aspect the invention is a method for determining heparanase procoagulant activity in a biological sample of a mammalian subject, said method comprising the steps of:
(a) preparing a first test solution (TS1) comprising a buffer solution, factor VIIa, and factor X;
(b) preparing a second test solution (TS2) comprising a buffer solution, factor VIIa, factor X, and an inhibitor capable of disrupting the Heparanase/Tissue Factor (Hepa/TF) complex;
(c) contacting aliquots of said biological sample with TS1 and TS2;
(d) adding to TS1 and to TS2 a substrate to factor Xa suitable to produce an optically detectable product;
(e) measuring the level of said optically detectable product in TS1 (L1); and
(f) measuring the level of said optically detectable product in TS2 (L2); wherein heparanase procoagulant activity (HPA) is obtained by subtracting L2 from L1, and heparanase relative contribution to the coagulation system is obtained by dividing HPA by L1.

In this method, the biological sample, factor VIIa and factor X may belong to the same mammalian species or from different ones. More specifically, factor VIIa and factor X, may be either recombinant proteins or natural plasma-derived proteins.

The inhibitor capable of disrupting the Heparanase/TF complex, as appearing in step (c), may have been identified via the screening method of the invention. Alternatively, any known compound binding the heparanase-TF binding site within any one of the heparanase molecule or the TF molecule, and modulating the interaction of heparanase and TF would be suitable. Particularly suitable are inhibitors selected from the group consisting of anti-Xa derivatives, unfractionated heparin (UFH), low molecular weight heparins (LMWH), fondaparinux, rivaroxaban, enoxaparin, tissue factor pathway inhibitor (TFPI), and tissue factor pathway inhibitor 2 (TFPI2), and derivatives thereof.

In specific embodiments, the inhibitor capable of disrupting the Heparanase/TF complex of step (c) is a peptide having an amino acid sequence selected from the group consisting of SEQ ID: 1 (Leu Leu Arg Tyr Tyr Tyr Asp Arg Tyr Thr Gln Ser Cys Arg), SEQ ID: 2 (Asn Asn Phe Tyr Thr Trp Glu Ala Cys Asp Asp Ala Cys Trp), SEQ ID: 3(Ile Cys Leu Leu Pro Leu Asp Tyr Gly Pro Cys Arm Ala Leu), SEQ ID: 4 (Ala Glu Ile Cys Leu Leu Pro Leu Asp Tyr Gly Pro Cys Arg), SEQ ID: 5 (Asn Asn Ala Glu Ile Cys Leu Leu Pro Leu Asp Tyr Gly Pro), SEQ ID: 6 (Arg Tyr Tyr Tyr Asp Arg Tyr Thr Gln Ser Cys Arg Gln Phe), SEQ ID: 7 (Asn Ala Asn Asn Phe Tyr Thr Trp Glu Ala Cys), and derivatives thereof.

The substrate to factor Xa suitable to produce an optically detectable product may be either a chromogenic substrate or a fluorogenic substrate. The man skilled in the art would be aware of commercially available sources of substrate suitable to the present invention. Further to the addition of said substrate to the tests solutions, a reaction with Xa occurs, producing an optically detectable signal. Generally, a stopping solution is added to the test solution in order to interrupt the chromogenic or fluorogenic reaction before performing any optical measurement of the test solutions. An example of stopping solution comprises an amount of glacial acetic acid.

In yet a further aspect, the present invention provides a diagnostic method for the detection and/or monitoring of a coagulation-related pathologic disorder in a mammalian subject, comprising the steps of:
(a) determining the level of heparanase procoagulant activity in a biological sample of said subject; and optionally determining the value of heparanase procoagulant activity in a control biological sample;
(b) comparing the value of heparanase procoagulant activity of said biological sample to a predetermined control value or to the value of heparanase procoagulant activity of said control sample;
wherein an elevated or reduced level of heparanase procoagulant activity in said biological sample as compared to said control sample or said predetermined control value is indicative of a coagulation-related pathologic disorder in said subject.

The diagnostic method of the invention is for instance suitable for a mammalian subject suffering from a pathologic condition such as contraceptive treatments, proliferative diseases, inflammatory diseases, orthopedic surgery, diabetic foot, endometriosis, sepsis, pregnancy vascular complications, and avascular necrosis (AVN) of hip.

According to this specific embodiment, elevated pro-coagulating activity of heparanase indicates that the sample is of a subject suffering from a condition associated with increased coagulation activity or thrombophilia. Such thrombotic diseases may be for example, cardiovascular complications including unstable angina, acute myocardial infraction (heart attack), cerebral vascular accident (stroke), arterial thrombosis, arterial aneurisms, artherosclerosis, peripheral arterial disease, stent thrombosis, venous thrombosis, Antiphospholipid syndrome (APLA), Protein C deficiency and other thrombophilia, superficial thrombophlebitis or deep vein thrombosis (DVT), pulmonary embolism (PE), vascular gestational complications such as recurrent abortions, abruptio placenta, intra uterine fetal death (IUFD) and severe preeclampsia, inflammation, malignancy and infectious processes.

"Thrombophilia" as used herein is a term which includes a number of genetic conditions which increase the tendency of the blood to clot, leading to sometimes serious and/or life-threatening complications depending on the location of the clot. Severity of complications associated with thrombophilia vary depending upon location and size of the clot. Clots in the extremities can cause superficial thrombophlebitis or deep vein thrombosis (DVT), both painful conditions. Clots in other areas of the body, such as the veins of major organs like the brain, liver and lungs, can be acutely life-threatening, and arterial clots can cause stroke and heart attack. Persons with thrombophilia wishing to have children should be aware of possible complications including stillbirth, preeclampsia, and eclampsia.

According to another embodiment, conditions having an undesired increased coagulation activity that can be diagnosed by the method of the invention, may be for example, cardiovascular complications including unstable angina, acute myocardial infraction (heart attack), cerebral vascular accident (stroke), arterial thrombosis, arterial aneurisms, artherosclerosis, peripheral arterial disease, stent thrombosis, venous thrombosis, Antiphospholipid syndrome (APLA), Protein C deficiency and other thrombophilia, superficial thrombophlebitis or deep vein thrombosis (DVT), pulmonary embolism (PE), vascular gestational complications such as recurrent abortions, abruption placenta, intra uterine fetal death (IUFD) and severe preeclampsia, inflammation, malignancy and infectious processes.

According to an alternative embodiment, reduced pro-coagulating activity of heparanase indicates that the sample is of a subject suffering from a condition associated with reduced coagulation activity. Such condition or diseases may be for example, Haemophilia, acquired or inherited deficiency of at least one of the coagulation factors such as: VIII, IX, or XIII, wherein said deficiency may be caused by at least one of vitamin K dependent factor deficiency, liver disease, uremia, proliferative disorders, and uncontrolled bleeding caused by anticoagulation therapy, trauma, surgery, delivery and disseminated intravascular coagulation (DIC).

According to one specific embodiment, heparanase procoagulating activity may be determined by comparing the levels of factor Xa in the sample in the absence of a compound inhibiting the interaction of heparanase with TF to the levels of factor Xa in the presence of said inhibitor. Suitable inhibitors may be any one of heparins, direct anti Xa inhibitors, TFPI, TFPI-2 and any of the inhibitory compounds identified by the screening method of the invention.

The diagnostic method of the invention is based on quantitative determination of heparanase mediated pro-coagulation activity in a biological sample obtained from the tested subject, by a suitable means.

As used herein in the specification and in the claims section below, the term "biological sample" refers to cells and tissues extracts, cell lysates and tissue specimens, including, but not limited to cancer cells and tissues. The term farther relates to body fluids, as further detailed below.

In a preferred embodiment, the diagnostic method of the invention may be particularly suitable for examination of body fluid such as blood, lymph, serum, milk, plasma, plural effusion, urine, faeces, semen, saliva, brain extracts, spinal cord fluid (SCF), appendix, spleen and tonsillar tissue extracts. Specifically, as demonstrated by the following Examples, a serum sample may be used.

In a further embodiment, the diagnostic method of the invention is intended for the diagnosis and monitoring of a pathological disorder in a mammalian subject. By "patient" or "mammalian subject" is meant any mammal for which such diagnosis is desired, including human, bovine, equine, canine, and feline subjects, preferably, human patient.

In a yet even further aspect, the present invention relates to a diagnostic kit for the detection and/or monitoring of a coagulation-related pathologic condition in a mammalian subject, comprising:

(a) coagulating agents, comprising factor X and factor VIIa;
(b) a compound inhibiting the interaction of heparanase and TF;
(c) substrate to factor Xa; and optionally
(d) one or more components selected from the group consisting of instructions for carrying out the detection of the procoagulant activity of heparanase in said subject; control samples; and predetermined calibration curve and instructions for using the same.

Quantitative analysis of heparanase coagulation activity can be carried out by interpolation into a standard curve, as is known in the art. Therefore, the kit of the invention may preferably include multiplicity of container means, each one having a different amount of heparanase.

The method and the kit of the invention for the diagnosis of a coagulation-related disorder in a mammalian subject is particularly suitable in the field of surgery, and more particularly in the field of orthopedic surgery, as discussed below.

Patients undergoing hip and knee-replacement surgery require effective thromboprophylaxis, and anticoagulants, and mechanical methods are now standard therapies. Despite prophylaxis, however subclinical deep vein thrombosis (DVT) develops in approximately 15 to 20% of patients soon after surgery, and symptomatic venous thromboembolism develops in 2 to 4% during the first 3 months post surgery [Geerts W H et al., Chest 2008; 133:381 S-453S]. The Inventors studied herein heparanase level and procoagulant activity in patient's plasma undergoing hip or knee surgery due to ostheoarthrosis or trauma.

Orthopedic surgery is a major risk factor for thrombosis. Data indicating increased heparanase expression in synovial fluid and synovial tissue of patients with osteoarthrosis [Li R W et al., Arthritis Rheum, 2008, 58:1590-600] encouraged the inventors to look for the systemic effects of heparanase level and procoagulant activity during the first month post surgery. According to the results disclosed therein there was a rapid increase in heparanase following surgery as found in the samples at one hour post surgery, potentially from the synovial fluid leak into the systemic circulation (FIG. 1). After 1 week the wound healing process was dominant parallel to further increase in heparanase. Interestingly, one month post operation, heparanase levels and procoagulant activity were still significantly high, although an equal contribution to TF/heparanase complex was TF activity (FIGS. 15A-15D). TF activity was shown to be determined by several parameters [Teffel J. et al, Circulation 2005, 112:341-9; Camera M et al., Arterioscler Thromb, Vasc Biol 1999; 19:531-7]. One of them is the concomitant secretion of TFPI, the endogenous inhibitor of TF. Another possible cause is cellular localization and structural modification that appear to determine the net procoagulant effect elicited by a given mediator [Camera M et al., Arterioscler Thromb, Vasc Biol 1999; 19:531-7; Schecter A D et al., J Clin Invest 1997; 100:2276-85; Wolberg A S et al., Blood Coagul Fibrinolysis 1999; 10:201-10].

The present invention which discloses the existence of TF/heparanase complex and the ability to quantify the relative contribution of heparanase to the complex enable to better understand the factors affecting TF activity in different clinical setups. According to the results, despite expected increase in TF activity 1 hour post surgery due to trauma to tissues and endothelial cells, TF activity was not significantly changed. Furthermore, the increase in TF activity 1 month post operation may potentially imply that in wound healing process, of the two complex components, heparanase increase the activity in an earlier response while TF activity changes in a delayed response when fibrosis become predominant. Samples at 1 week and 1 month were taken 24 hours after enoxaparin injection. Effect of very low dose enoxaparin was not previously determined. Low levels of enoxaparin can potentially reduce the result of TF/heparanase activity, implying that without enoxaparin treatment the results would have been even more significant. In addition, as disclosed previously, the assay of heparanase procoagulant activity excess exogenous factor VIIa and factor X were added to saturate the system with these two factors. Level of plasma factor X is 0.14 µM [Biggs R et al., Br J Haematol 1963; 9:532-47] and in the assay ten times higher level of exogenous factor X (1.4 µM) was added, further attenuating enoxaparin effect via anti-thrombin.

Fracture of the lower extremities is followed by coagulation activation detected by higher levels of prothrombin fragment 1+2 (F 1+2), thrombin-antithrombin (TAT) complex and fibrin degradation product (FDP) compared to control levels [Sorensen J V et al., Thromb Res 1992; 65:479-86]. High levels of F 1+2 TAT and D-Dimer before elective hip surgery were associated with increased risk of thrombosis [Cofrancesco E et al., Thromb Haemost 1997; 77:267-9]. Hemostatic markers following orthopedic surgery were previously studied. Thromboprophylaxis dis-continued a week after surgery is followed by increase in plasma TAT and D-Dimer levels between the 6th and 35th postoperative day and may predict DVT formation [Dahl O E et al., Thromb Res 1995; 80:299-306]. Siemens at al. assessed procoagulant and fibrinolytic parameters including TAT, D-Dimer, plasminogen activator inhibitor 1 (PAI-1), anti-thrombin and protein C levels, in four different types of surgeries. Among patients with total hip replacement, receiving low molecular weight heparin (LMWH) prophylaxis, coagulation changes were most pronounced. Samples were drown before, 1-2 hours post-operation, and on the mornings of postoperative days 1-5. Maximum activation of the coagulation system was reached 1-2 hours post operatively and decreased until normal on the fifth postoperative day. Parameters displaying the greatest changes were TAT complex and D-Dimer [Siemens H J et al., J Clin Anesth, 1999; 11:622-9]. In contrast, López et al. compared hemostatic markers in orthopedic vs. abdominal surgery in patients receiving LMWH prophylaxis. Samples were taken before operation and on postoperative days 1, 3 and 7. The following parameters were assessed: F 1+2, TAT complex, fibrinopeptide A, tissue plasminogen activator (TPA), PAI-1, plasmin-antiplasmin complex and FDP. Significant increase in the clotting markers postoperatively compared to preoperative values was found, which remained until post operative day 7 [Lopez Y, Int J Clin Lab Res, 1997; 27:233-7]. Cofrancesco et al. found that after total hip replacement, despite thromboprophylaxis, F 1+2, TAT and D-Dimer plasma levels measured on days 1, 3 and 6 were higher than at baseline [Cofrancesco E et al., Thromb Haemost 1996; 75:407-11]. In the present study, no significant differences were found in thrombin and factor Xa levels during the first week, potentially indicating that these down stream coagulation products may not be sufficient to represent the hemostatic balance, probably due to short half-life of these molecules.

Currently, the time of stopping prophylactic anticoagulants after surgery is not individualized. In the present study, both patients with a thrombotic event (FIGS. 17A-17B) were mobile 1 month post surgery, and at least in the patient with PE, no further signs or symptoms could predict the thrombosis. In these two patients heparanase and TF activity at 1 month compared to baseline were much higher then the average increase in the entire study group. It is probable that if the assay of the present invention enabling the determination of TF/heparanase procoagulant activity would have been routinely done preoperatively and at one month post surgery, enoxaparin wouldn't have been stopped a week later the surgery in these two patients.

Increased heparanase levels probably represent the endogenous potential of the patient to express heparanase and the extent of wound healing process. Differences in heparanase levels and procoagulant activity might be partially attributed to recently found heparanase gene single nucleotide polymorphisms (SNPs). Ostrovsky et al. found that genotype and allele frequencies in Jewish populations were different from non-Jewish populations, except for a certain similarity to Caucasians [Ostrovsky O et al., Acta Haematol 2007; 117: 57-64]. This group also demonstrated an association of heparanase gene SNPs with hematological malignancies [Ostrovsky O et al., Leukemia 2007; 21:2296-303]. Ralph et al. reported on association between a specific heparanase SNPs and stage of ovarian cancer disease while the association was not found in vascular endothelial growth factor (VEGF) SNPs [Ralph S et al., Cancer Sci 2007; 98:844-9]. Further research is needed to explore the clinical relevance of heparanase gene polymorphism for thrombotic risk assessment.

In summary, the above example demonstrates the involvement of heparanase in the orthopedic postoperative period, as well as the clinical relevance of providing heparanase procoagulant activity assay to evaluate the thrombotic potential after orthopedic surgery.

The invention will be described in more detail on basis of the following Examples, which are illustrative only and do not in any way limit the invention. Many modifications and variations of the present invention are possible in light of the present teachings. It is therefore understood, that within the scope of the appended claims, the invention may be practiced otherwise than specifically described.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Example A

Heparanase Procoagulant Activity

Design and Methods
Study Group

Thirty five consecutive patients with newly diagnosed acute leukemia were enrolled over a 7-month period. The patient's age ranged from 18-78 (mean, 47±20 years), 21 males and 14 females. Twenty-two patients had acute myeloid leukemia M1-2, nine had acute myeloid leukemia M4-5 and four had acute lymphocytic leukemia. The patients were diagnosed according to established morphological, immunophenotypic and molecular criteria. After obtaining informed consent, peripheral blood was taken at the time of diagnosis and prior to chemotherapy treatment. The patients were followed-up prospectively for the occurrence of symptomatic thrombotic manifestations during the first month following the start of chemotherapy. Twenty control samples were obtained from healthy donors (age 24-55, mean 36±12 years, 14 males and 6 females). A total of 3 ml of peripheral blood was collected, applying sodium citrate 3.2% (0.12 M) sodium citrate (1:10) as an anticoagulant. Plasma was obtained by centrifugation (1500 g for 15 minutes at 4° C.) and all plasma samples were frozen and thawed once.
Cell Culture and Transfection.

HEK-293 cells were purchased from the American Type Culture Collection (ATCC). Cells were grown in Dulbecco's modified Eagle's medium (DMEM) supplemented with 10% fetal calf serum and antibiotics (Biological Industries, Beit Haemek, Israel). Cells were stably transfected with full-length human heparanase (65 kDa) cDNA cloned into the pSecTag2 vector (Invitrogen, Carlsbad, Calif.), using the FuGENE 6 reagent, according to the manufacturer's instructions (Roche Applied Science, Indianapolis, Ill.) [Gingis-Velitski S. et al., J. Biol. Chem. 2004, 279(42):44084-92; Zetser A, et al., Cancer Res. 2003, 63(22):7733-41; Zetser A. et al., J Cell Sci. 2004, 117(Pt 11):2249-58]. Transfection proceeded for 48 hours, followed by selection with Zeocin (Invitrogen, Carlsbad, Calif.) for 2 weeks. Stable transfectant pools were further expanded and analyzed. Modified species of heparanase were used: a single chain GS3 active heparanase gene construct, comprising the 8 and 50 kDa heparanase subunits (8+50) (kindly provided by Dr. Christian Steinkuhler, IRMB/Merck Research Laboratories, Pomezia, Italy) [Nardella C. et al., Biochemistry, 2004, 43(7):1862-73], and heparanase gene construct mutated at $Glu^{225}$ and $Glu^{343}$, critical for the enzyme catalytic activity [Zetser A. et al., Cancer Res. 2006; 66(3):1455-63: Hulett M D, Biochemistry. 2000; 39(51): 15659-67].
Reagents and Antibodies The single chain GS3 active heparanase gene construct, comprised of the 8 kDa and 50 kDa heparanase heterodimer (8+50) was purified from the conditioned medium of baculovirus-infected cells [Nadir Y. et al., J. Thromb. Haemost. 2006, 4(11):2443-51]. GS3 active heparanase was assayed for the presence of bacterial endotoxin by Biological Industries (Beit Haemek, Israel), using the gel-clot technique (*Limulus* amebocyte lysate—LAL test) and was found to contain less than 10 pg/ml endotoxin. Polyclonal antibody 1453 was raised in rabbits against the entire 65 kDa heparanase precursor isolated from the conditioned medium of heparanase-transfected HEK-293 cells. The antibody was affinity purified on immobilized bacterially expressed 50 kDa heparanase GST fusion protein [Zetser, A. J. et al. Cell Sci. 117:2249-2258 (2004)]. Anti-heparanase monoclonal antibody 130 was kindly provided by InSight Pharmaceuticals (Rehovot, Israel). Lipidated recombinant human TF, monoclonal and polyclonal anti-human TF antibodies, and monoclonal anti human factor X and Xa heavy chain (I.D. 5010) were purchased from American Diagnostica (Stanford, Conn., USA). Recombinant human factor VIIa, recombinant human inactivated factor VIIa, recombinant TFPI, plasma-derived human factor X, plasma-derived human prothrombin, chromogenic substrate for factor Xa (I.D. 222, Formula: MeO—CO-D-CHG-Gly-Arg-pNA.AcOH solubility: Tris buffer, pH 8.4) and chromogenic substrate for thrombin (I.D. 238, Formula: H-D-HHT-Ala-Arg-pNA.2AcOH solubility: Tris buffer, pH 8.4) were purchased from American Diagnostica (Stanford, Conn., USA). Recombinant TFPI-2 was purchased from R&D (Minneapolis, Minn., USA) and unfractionated heparin was purchased from Sigma (St. Louis, Mo., USA). Rivaroxaban was purchased from Bayer (Leverkusen, Germany). All coagulation factors were dissolved in double-distilled water.
Activated Factor X Generation Assay Following preliminary experiments to quantify the appropriate protein doses, we performed a basic experiment of factor Xa generation in the following manner: the concentrations mentioned are the final concentrations. Lipidated recombinant human TF (0.004 µM, 200 pg/mL), recombinant human factor VIIa (0.04 µM) and plasma-derived human factor X (1.4 µM) were incubated in 50 µL assay buffer (0.06 M Tris, 0.04 M NaCl, 2 mM CaCl 2, 0.04% bovine serum albumin, pH 8.4) to a total volume of 125 µL in a 96-well sterile plate. After 15 min at 37° C., chromogenic substrate for factor Xa was added (1 mM). After 20 min, the reaction was stopped with 50 µL of glacial acetic acid and the level of factor Xa generation was determined using an enzyme-linked immunosorbent assay (ELISA) plate reader (Power Wave XS, BIO-TEK, VT, USA). In order to visualize the increased production of factor Xa by western blotting, the experiment was repeated with 7 µM factor X. After 15 min at 37° C., half of the reaction volume was subjected to blotting using monoclonal anti-human factor X/Xa heavy chain antibody.
Sodium Dodecylsulfate Polyacrylamide Gel Electrophoresis and Immunoblot Analysis Proteins were subjected to 10% Sodium dodecylsulfate polyacrylamide gel electrophoresis and transferred to a polyvinylidene fluoride membrane (BioRad, Maylands, Calif., USA). The membrane was probed with the appropriate antibody followed by horseradish peroxidase-conjugated secondary antibody (Jackson ImmunoResearch, West Grove, Pa., USA) and chemiluminescence substrate (Pierce, Rockford, Ill., USA), as described in [Nadir (2006) ibid.].
Thromboelastography The assay was performed according to the manufacturer's recommendations. Briefly, 3 mL of healthy donor's whole blood were collected in a bottle containing 3.2% (0.12M) sodium citrate and stored at room temperature. Recalcification and TEG® measurements at 37° C. were performed in disposable cups of the Thrombelastograph® coagulation analyzer (Haemoscope Corporation, Skokie, Ill., USA).

Heparanase Enzyme-Linked Immunosorbent Assay (ELISA)

Wells of microtiter plates were coated (18 h, 4° C.) with 2 µg/ml of anti-heparanase monoclonal antibody in 50 µl of coating buffer (0.05 M $Na_2CO_3$, 0.05 M $NaHCO_3$, pH 9.6) and were then blocked with 2% bovine serum albumine in phosphate buffer saline for 1 h at 37° C. Samples (200 µl) were loaded in duplicates and incubated for 2 h at room temperature, before the addition of 100 µl antibody 1453 (1 µl/ml) for an additional period of 2 h at room temperature. Horseradish peroxidase-conjugated goat anti-rabbit IgG (1:20,000) in blocking buffer was added (1 h, room temperature) and the reaction was visualized by the addition of 50 µl chromogenic substrate (TMB; MP Biomedicals, Germany) for 30 minutes. The reaction was stopped with 100 µl $H_2SO_4$ and absorbance at 450 nm was measured using an ELISA plate reader (Power Wave XS, BIO-TEK, VT). Plates were washed five times with washing buffer (PBS, pH 7.4 containing 0.1% (v/v) Tween 20) after each step. As a reference for quantification, a standard curve was established by serial dilutions of recombinant 8+50 GS3 active heparanase (390 pg/ml-25 ng/ml) [Shafat, I. et al. Biochem. Biophys. Res. Commun. 341:958-963 (2006)]. The assay detects almost exclusively the active heparanase and only poorly the full-length heparanase (65 kDa).

Co-Immunoprecipitation

The interaction between TF and heparanase was analyzed by co-immunoprecipitation (Co-IP). The ProFound™ Co-Immunoprecipitation Kit in which the antibody is coupled to gel support, was employed according to the manufacturer's instruction (Pierce, Rockford, Ill., USA). Briefly, coupling gel was washed with coupling buffer. Polyclonal anti-TF or polyclonal anti-heparanase (1453) antibodies (100 µg) and 5 M sodium cyanoborohydride, were added to the gel support and incubated at 4° C. for 4 hours. The gel was then washed with quenching buffer and incubated with the quenching buffer and sodium cyanoborohydride at 20° C. for 30 minutes. Next, the gel was washed 4 times with wash solution, once with elution buffer, and twice with coupling buffer. Purified proteins (0.5 µg) were added to the gel and incubated for 2 hours at 4° C. The gel was washed four times with coupling buffer and bound proteins were eluted with elution buffer (pH 2.5) neutralized by 1 M Tris-HCl, pH 9.5, and subjected to immunoblot analysis. Monoclonal anti-TF and monoclonal anti-heparanase antibodies were used to detect the respective coupled protein. Irrelevant anti-GST polyclonal antibody (100 µg) and uncoupled beads were used as controls.

Statistical Analysis

Data were evaluated by SPSS software for Windows version 13.0 (SPSS Inc., Chicago, Ill., USA). Pearson's correlation (r) was used to assess the link between patients and controls regarding heparanase levels and factor Xa levels. Values are reported as mean±standard deviation. P values less than 0.05 were considered statistically significant.

Results

Example A1

Heparanase Increases Activated Factor X Levels

The factor Xa generation assay was performed as described in the Design and Methods section with increasing doses of recombinant human heparanase (GS3) added prior to the addition of the coagulation factors. Surprisingly, heparanase increased factor Xa production in a dose-dependent manner visualized by a chromogenic substrate (FIG. 1A) and by western blot (FIG. 1B). It should be noted that factor X is composed of two polypeptide chains, a heavy chain with a molecular weight of 38 kDa and a light chain with a molecular weight of 18 kDa joined by a dipeptide Arg-Arg. The factor VIIa-TF complex activates the conversion of factor X to factor Xa by cleaving the heavy chain to a 33 kDa peptide. The factor Xa produced in the presence of heparanase has the same molecular weight as factor Xa produced without heparanase, indicating that the site of cleavage in factor X heavy chain is most likely the same. In order to exclude contamination of the heparanase preparation during the routine procedure of purification described in the Design and Methods section, the inventors tested the effect of overnight serum-free without phenol medium of 293 HEK cells overexpressing heparanase and its derivatives compared to mock. The proteins were further purified from the culture medium and analyzed. Similar quantities of proteins were obtained from the culture media. A 2-fold increase in factor Xa levels was observed with the medium of full-length heparanase and active heparanase (FIG. 1C). The double mutant inactive heparanase also increased factor Xa levels, indicating that the effect is non-enzymatic (FIG. 1C).

Example A2

Heparanase Increases Thrombin Levels

In order to verify that factor Xa produced in the presence of heparanase is active, thrombin generation, the next step in the coagulation cascade, was examined. The experiment described above (FIG. 1A) was repeated and plasma-derived human prothrombin (222 µM) was added following the addition of factor X. After 15 minutes at 37° C., chromogenic substrate for thrombin was added (1 mM). In the presence of heparanase, thrombine generation was increased (FIG. 1D).

Example A3

Heparanase Increases Coagulation without Substituting One of the Coagulation Factors In order to verify that the heparanase molecule is a cofactor for the factor VIIa-TF complex, heparanase was added to the conditions described in FIG. 1A. Factor Xa was not generated in the absence of each of the essential factors (i.e., TF, factor VIIa, and factor X) or in the presence of inactivated VIIa, as shown in FIG. 1E, indicating that the heparanase preparation is neither contaminated with, nor does it replace, any of these coagulation factors. Moreover, no factor Xa was generated when heparanase was added to factor X for 15 min at 37° C., followed by the addition of a chromogenic substrate for Xa. Similarly, when heparanase was incubated (15 min, 37° C.) with pro-thrombin followed by the addition of a chromogenic substrate for thrombin, no thrombin was generated (data not shown). These experiments confirm that heparanase does not activate factor X or prothrombin directly, but rather serves as a cofactor for the TF-factor VIIa complex.

Example A4

Heparanase Increases Coagulation in Normal Human Plasma

Figure 2:
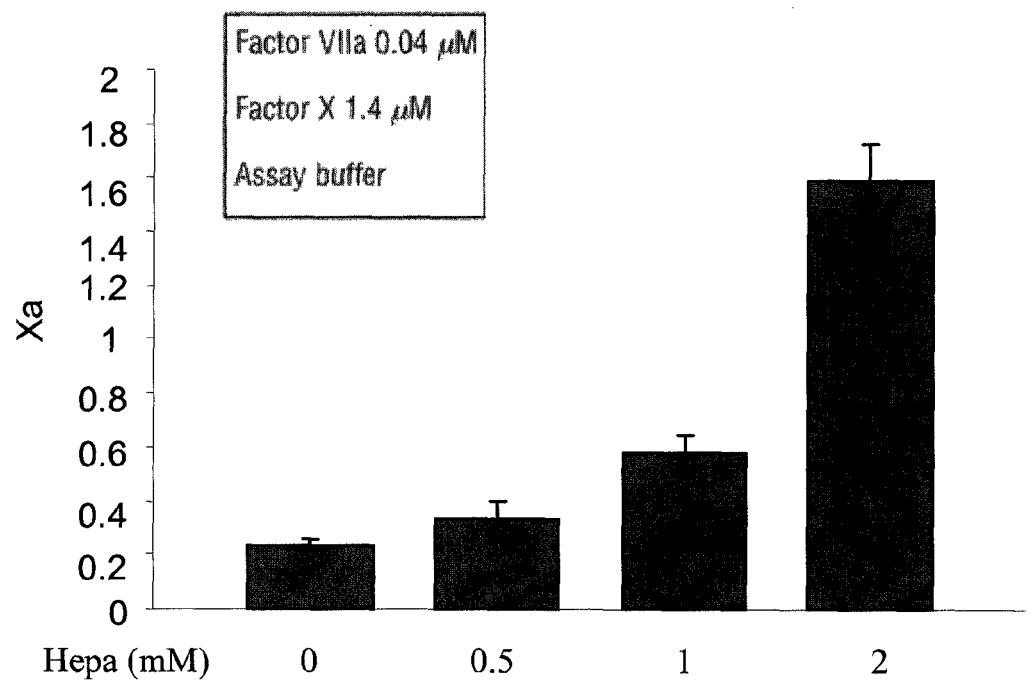
Figure 3:
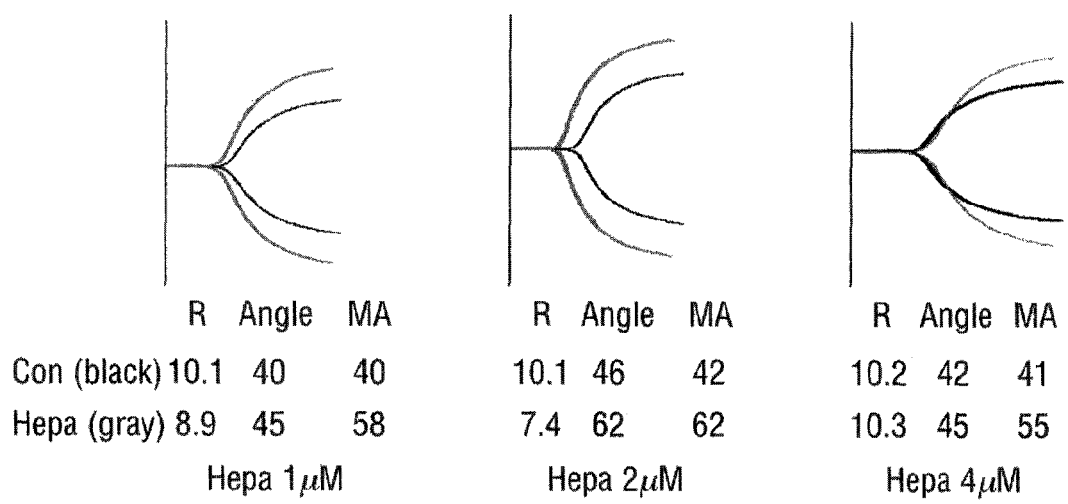

Next, the procoagulant effect of heparanase in human plasma was tested. Using an ELISA method [Shafat I. et al., Biochem Biophys Res. Commun. 2006, 341(4):958-63] it was found that the level of active heparanase (GS3 8+50 kDa) in plasma drawn in sodium citrate was 500±29 pg/mL (0.0085 µM) [Shafat I., Neoplasia 2007, 9(11):909-16]. When heparanase, factor VIIa and factor X were incubated (15 min, 37° C.) with pooled normal human plasma from five healthy donors, followed by the addition of a chromogenic substrate for factor Xa, a 7- to 8-fold increase in factor Xa levels was obtained compared to levels in plasma incubated in the absence of heparanase (FIG. 2). In this condition the coagulation was mainly dependent on the concentration of endogenous TF, as described previously [Suefuji H. et al., Am Heart J. 1997, 134(2 Pt. 1):253-9; Kim H K et al., Cardiology. 2000, 93(1-2):31-6]. The effect of heparanase was also tested in whole blood using thromboelastography. Citrated blood samples from healthy donors to which factor VIIa (0.04 µM) and factor X (1.4 µM) were added were recalcified according to the manufacturer's recommendations (final concentration of $CaCl_2$ 8 mM) and arranged in the disposable cups of the thromboelastogram. With increasing doses of heparanase there was a significant reduction in time to clot formation and an increase in thrombus strength (FIG. 3). At the highest dose (4 µM) the effect on time to clot formation was abolished (FIG. 3). In order to attribute clinical relevance to the newly identified function of heparanase, 55 plasma samples were tested for their heparanase content using ELISA and the heparanase content correlated to factor Xa levels using a chromogenic substrate for Xa. Thirty-five samples were from patients with acute leukemia and 20 samples were from healthy donors. Using Pearson's analysis, a strong positive correlation was found between the two parameters (r=0.735, P=0.001), indicating a potential in vivo effect of heparanase on factor Xa levels in plasma (FIG. 4). Using a t-test for independent samples, a significant difference was found between patients and controls in heparanase levels (1091±352 versus 499±129, respectively; P=0.0001) and factor Xa levels (0.83±0.32 versus 0.51±0.17, P=0.004), respectively. Four thrombotic manifestations (two pulmonary emboli, one catheter-related deep vein thrombosis, and one myocardial infarction) occurred in the group of patients in the first month during which chemotherapy was initiated. The levels of heparanase in these patients were exceedingly high (1353, 1276, 1220, and 1276 pg/mL) as were the levels of factor Xa (1.23, 0.61, 1.12, and 0.87; optical density of 405-490 nm). The subgroup with thrombotic manifestations is, however, too small for statistical analysis.

Example A5

Heparanase Increases Coagulation by Enhancing TF Activity Rather than VIIa Activity In intent to further examine the mode of heparanase effect on the coagulation cascade, the inventors wished to establish whether heparanase enhances the effect of TF or factor VIIa. For this aim the experiment described in Example 1 was repeated using reduced levels of TF. As shown in FIG. 5A, the effect of heparanase (gray bars) on Xa levels compared to control (white bars, without heparanase) are in line with the results presented above. Interestingly, even with very low levels of TF (3.13 pg), the addition of heparanase increased Xa generation by three folds. In contrast, as demonstrated in FIG. 5B, the effect of heparanase was abolished in the absence of sufficient factor VIIa, indicating that VIIa level became the limiting factor of the reaction, without any additional contribution of heparanase to Xa generation. This experiment supports the notion that heparanase serve as a cofactor to TF activity rather than to VIIa activity.

Example A6

Inhibition of Heparanase Procoagulant Activity

Four inhibitors were tested: unfractionated heparin, TFPI, TFPI-2, and anti-Xa derivative (rivaroxaban). Whereas unfractionated heparin and the anti-Xa derivative abolished the procoagulant effect of heparanase (FIG. 6A, 6C), TFPI and TFPI-2 attenuated the effect (FIG. 6B). As far as we know, rivaroxaban does not inhibit the TF-factor VIIa complex but it succeeded in abolishing the factor Xa effect generated in the presence of heparanase. Interestingly, when heparanase, was added, TFPI-2 was a more effective inhibitor than TFPI (FIG. 6B).

Example A7

Co-Interaction Between TF and Heparanase

Using co-immunoprecipitation and far-western analyses, we demonstrated that heparanase actually interacts with TF (FIGS. 7A and 7B). Unfractionated heparin abrogated this interaction completely (FIG. 7A), in accordance with the abolishment of the heparanase procoagulant effect (FIG. 6A).

Example B

Heparanase Procoagulant Activity Assay

Materials and Methods
Study Group
Thirty five third-trimester pregnant women (weeks 36-41) who were in labor or came for appointed elective cesarean section (CS) were enrolled, over a 5 month period, between December 2008 and April 2009, at the Rambam Medical Center. Exclusion criteria included age less than 18 years, concomitant medications other than supplement minerals and vitamins, acute or chronic illness. Ten cases were of CS for accepted obstetric indications (previous CS or fetal breech presentation). Emergency cesarean deliveries were not included in this study. Sixteen patients experienced normal spontaneous vaginal deliveries. Two of the 16 vaginal deliveries were induced by oxytocin. Nine cases were of intrauterine growth restriction (IUGR) defined as weight below the 10 percentile for gestational age (6 CS and 3 vaginal deliveries). Two IUGR CS deliveries were complicated by high blood pressure and IUGR without other signs or symptoms of preeclampsia and without blood pressure reduction medications. One IUGR CS delivery was complicated by oligohydramnios. In one of the 6 CS IUGR deliveries an attempt using prostaglandin $E_2$ ($PGE_2$) and oxytocin was made, before surgery. Two IUGR vaginal deliveries were induced with $PGE_2$. All IUGR babies were examined by pediatricians and were found to have no morphological abnormalities and no indication of infection. Twenty control samples were of non-pregnant healthy women not taking oral contraceptives or any other medications. After obtaining informed consent, peripheral blood was taken 1-8 hours before vaginal delivery and 24 hour before elective CS. A total of 3 ml of peripheral blood was collected, with 3.2% sodium citrate as an anticoagulant. Plasma was obtained by centrifugation (1500 g for 15 minutes at 4° C.) and all plasma samples were frozen and thawed once.

Reagents and Antibodies

Single chain GS3 heparanase gene construct, comprising the 8 and 50 kDa heparanase subunits (8+50) was purified from the conditioned medium of baculovirus-infected cells [Nadir Y. et al., J. Thromb. Haemost 2006, 4:2443-51]. GS3 heparanase was assayed for the presence of bacterial endotoxin by Biological Industries (Beit Haemek, Israel), using the gel-clot technique (*Limulus* amebocyte lysate—LAL test) and was found to contain less than 10 pg/ml endotoxin. Monoclonal anti-heparanase antibody 1E1 was generated by immunizing Balb/C mice with the entire 65 kDa heparanase protein [Shafat I et al., Biophys. Res. Commun 2006, 341: 958-63]. Polyclonal antibody 1453 was raised in rabbits against the entire 65 kDa heparanase precursor isolated from the conditioned medium of heparanase-transfected HEK-293 cells. The antibody was affinity-purified on immobilized bacterially expressed 50 kDa heparanase GST fusion protein [Zetser A et al., J Cell Sci. 2004, 117:2249-58]. Lipidated recombinant human TF, recombinant human factor VIIa and plasma-derived human factor X were purchased from American Diagnostica (Stanford, Conn.). Fondaparinux (Arixtra) was purchased from GlaxoSmithKline (London, UK). All coagulation factors were dissolved in double-distilled water.

Heparanase Procoagulant Activity Assay

A basic experiment of factor Xa generation was performed in the following manner: the concentrations mentioned are the final concentrations. Heparanase GS3 (1.5 µM), lipidated recombinant human TF (0.004 µM, 200 pg/ml), recombinant human factor VIIa (0.04 µM) and plasma-derived human factor X (1.4 µM) were incubated in 50 µl assay buffer (0.06 M Tris, 0.04 M NaCl, 2 mM $CaCl_2$, 0.04% BSA, pH 8.4) to a total volume of 125 µl in a 96-well sterile plate. After 15 minutes at 37° C., chromogenic substrate to factor Xa was added (1 mM). Following 20 minutes, the reaction was stopped with 50 µl of glacial acetic acid and the level of Xa generation was determined using an ELISA plate reader (Power Wave XS, BIO-TEK, VT). Heparins were shown to abrogate the TF heparanase complex [Nadir Y. et al., Haematologica 2010, 95(11):1927-1934], so in parallel, the same assay was performed except that fondaparinux (2.5 µg/ml) was added to the assay buffer. The subtraction of the first assay result from the second assay result determines heparanase procoagulant activity. Heparanase procoagulant activity/(TF+heparanase activity) results in heparanase relative contribution (%). When the assay was done in plasma, 25 µl of plasma was used and the only difference was that no exogenous TF or heparanase was added.

Heparanase Enzyme-Linked Immunosorbent Assay (ELISA)

Wells of microtiter plates were coated (18 h, 4° C.) with 2 µg/ml of anti-heparanase monoclonal antibody in 50 µl coating buffer (0.05 M $Na_2CO_3$, 0.05 M $NaHCO_3$, pH 9.6) and were then blocked with 2% BSA in PBS for 1 h at 37° C. Samples (200 µl) were loaded in duplicates and incubated for 2 h at room temperature, followed by the addition of 100 µl antibody 1453 (1 µl/ml) for an additional period of 2 h at room temperature. HRP-conjugated goat anti-rabbit IgG (1:20,000) in blocking buffer was added (1 h, room temperature) and the reaction was visualized by the addition of 50 µl chromogenic substrate (TMB; MP Biomedicals, Germany) for 30 minutes. The reaction was stopped with 100 µl $H_2SO_4$ and absorbance at 450 nm was measured using an ELISA plate reader (Power Wave XS, BIO-TEK, VT). Plates were washed five times with washing buffer (PBS, pH 7.4 containing 0.1% (v/v) Tween 20) after each step. As a reference for quantification, a standard curve was established by serial dilutions of recombinant 8+50 GS3 heparanase (390 pg/ml-25 ng/ml) [10].

Factor Xa and Thrombin Chromogenic Assays

Chromogenic substrate to factor Xa (I.D. 222, solubility: Tris buffer pH −8.4) and chromogenic substrate to thrombin (I.D. 238, solubility Tris buffer, pH −8.4) were purchased from American Diagnostica (Stanford, Conn.). 50 µl plasma was added to 50 µl Tris buffer (0.06 M, pH 8.4) and 25 µl of chromogenic substrate to factor Xa (5 mM) or 25 µl of chromogenic substrate to thrombin (5 mM). After 30 minutes the reaction was stopped with glacial acetic and the absorbance at 405 nm-490 nm was measured using an ELISA plate reader (Power Wave XS, BIO-TEK, VT).

Antithrombin Activity

Antithrombin activity in plasma was measured on the STA compact analyzer using STASTACHROM® kit (Diagnostica STAGO, France).

Free TFPI ELISA

Plasma free TFPI levels were determined using the ASSERACHROM® FREE TFPI ELISA according to the manufacturer's (Diagnostica STAGO, France) instructions. Briefly, the internal wall of a plastic microwell was precoated with the first monoclonal antibody to TFPI. The second anti-Free TFPI monoclonal antibody that is coupled with peroxidase is added to the precoated microwell at the same time as the plasma (diluted 1:20). The Free TFPI of the plasma being tested was simultaneously captured by the two monoclonal antibodies. Next the bound peroxidase was revealed by its activity on the substrate ortho-phenylenediamine producing a yellow color. After stopping the reaction with sulfuric acid the absorbance at 492 nm was measured using an ELISA plate reader (Power Wave XS, BIO-TEK, VT). As a reference for quantification, a standard curve was established by serial dilutions of TFPI.

Statistical Analysis

Data were evaluated by SPSS software for Windows version 13.0 (SPSS Inc., Chicago, Ill.). Pearson's correlation (r) was used to assess the link between plasma heparanase procoagulant activity and TF activity, heparanase, TFPI, thrombin and factor Xa levels. The T-TEST for independent variables was used. $P<0.05$ was considered statistically significant. Values are reported as mean±SD.

Results

Example B1

Description of the Heparanase Procoagulant Activity Assay

According to our knowledge regarding the presence of TF/heparanase complex [Nadir Y. et al., ibid.], the descriptive method to perform the assay discriminating the effect of TF from that of heparanase is described in FIG. 8. The assay is sensitive to heparanase activity, since TF+heparanase activity increased when heparanase levels were gradually elevated (FIGS. 9A-9C). Note, TF+heparanase slope was less prominent than heparanase slope due to stable levels of TF (FIGS. 9A and 9C, respectively). In a similar manner, it is demonstrated that the assay is also sensitive to TF levels (FIGS. 10A-10C). Note, TF+heparanase slope was less prominent compared to that of TF slope due to stable levels of heparanase (FIGS. 10A and 10C, respectively).

Example B2

Heparanase Procoagulant Activity Assay, TF Activity and Heparanase Levels by ELISA in Pregnant Women at Delivery Subsequently, we searched for clinical data supporting this newly identified assay to determine heparanase procoagulant activity. In plasma, fondaparinux not only abrogates TF/heparanase complex but also enhances anti-thrombin, thus less chromogenic substrate will be cleaved by factor Xa. In plasma from healthy individuals, the range of anti-thrombin as detected by immunologic or functional tests is reasonably narrow. Fondaparinux used in the assay at a concentration of 2.5 µg/ml (12.5 mg/5 liter) is approximately twice the recommended therapeutic anticoagulant dose [Samama M M et al., Thromb. Res. 2003, 109:1-11]. Heparins accelerate anti-thrombin activity about 1000-fold increase [Craig P A et al., J Biol Chem 1989, 264:5452-61]. The dramatic amplification in anti-thrombin activity actually maximizes anti-thrombin potential effect, rendering differences in plasma levels neglectable. Thus, the suggested assay cannot be used for anti-thrombin activity determination as the excess of heparin obscures results. Since fondaparinux, that has a very predictable effect in plasma, is added to the assay in a fixed dose, we can consider the effect on anti-thrombin as constant. Fifty-five plasma samples were tested. The characteristics of the study group are described in the Material and Methods section and in Table 1 (FIG. 11). The only statistically significant differences between the groups were the birth weight and birth week of delivery in the IUGR group compared to the vaginal and CS groups. No difference in heparanase levels by ELISA were found in pregnant compared to non-pregnant women. Using the heparanase procoagulant assay differences in heparanase activity were found to be much more dramatic and the relative contribution of heparanase to the complex (percentage of total) revealed a major role of heparanase at delivery compared to controls (FIG. 12). In the CS group, TF+heparanase, TF and heparanase activities were significantly higher compared to that of the vaginal and IUGR groups. Nevertheless, these activities were still much higher in the vaginal and IUGR cases compared to non-pregnant women. Differences in TF+heparanase or heparanase activities were more prominent compared to TF activity. Good correlations were found between heparanase and TF+heparanase assays ($r=0.95$, $p=0.0001$), TF and TF+heparanase assays ($r=0.65$, $p=0.0001$), heparanase and TF assays ($r=0.46$, $p=0.01$). No correlation was found between heparanase ELISA and heparanase assay ($r=-0.29$, $p=0.1$). The 55 samples were analyzed 1-6 months from the collection day. Thirty samples were re-analyzed 3-9 months from the collection day for heparanase procoagulant assay. The correlation between the two runs was $r=0.9$, $p=0.001$, but the Xa generated in the second run was ~30% less compared to the first run, probably reflecting decay of the analyzed proteins within time.

Example B3

Antithrombin Activity, Factor Xa, Thrombin, and Free TFPI Levels in Pregnant Women at Delivery Differences in Xa and thrombin were significant in pregnant vs. non-pregnant women (FIG. 13). No differences were found in free TFPI levels or antithrombin activity in the study groups (FIG. 13). Additionally, all antithrombin results were in the normal range (80-120%). A good correlation was found between Xa levels and thrombin levels ($r=0.6$, $p=0.001$). No correlations were found between heparanase procoagulant assay and: Xa levels ($r=0.24$, $p=0.3$), thrombin levels ($r=0.26$, $p=0.18$), TFPI levels ($r=-0.07$, $p=0.9$) and antithrombin activity ($r=0.12$, $p=0.4$).

Example C

Heparanase Procoagulant Activity in Orthopedic Surgery Patients Receiving Prophylactic Dose of Enoxaparin Material and Methods
Study Group.
Patients were enrolled over a 6 month period at the Orthopedic B department of Rambam Medical Center. The study group included 50 orthopedic patients. 31 patients underwent hip surgery and 19 had knee operation. 15 individuals suffered from traumatic hip fractures and 35 had osteoarthrosis. All patients received a prophylactic dose of enoxaparin (40 mg/day for weight 50-90 kg, 60 mg/day >90 kg) starting 6-8 hours post operation and lasting for 5 weeks according to acceptable guidelines [Geerts W H et al., Chest 2008; 133: 381 S-453S]. After obtaining informed consent, peripheral blood was drawn 1 hour preoperatively and at 1 hour, 1 week and 1 month post operation. Samples were taken 24 hours after enoxaparin injection. A total of 6 ml of peripheral blood was collected, with 3.2% sodium citrate as an anticoagulant. Plasma was obtained by centrifugation (1500 g for 15 minutes at 4° C.) and all plasma samples were frozen (−86° C.) and thawed once.
Reagents and Antibodies
Single chain GS3 heparanase gene construct, comprising the 8 and 50 kDa heparanase subunits (8+50) was purified from the conditioned medium of baculovirus-infected cells [Nadir Y. et al., J. Thromb. Haemost. 2006, 4:2443-2451]. GS3 heparanase was assayed for the presence of bacterial endotoxin by Biological Industries (Beit Haemek, Israel), using the gel-clot technique (*Limulus* amebocyte lysate—LAL test) and was found to contain <10 pg/ml endotoxin. Monoclonal anti-heparanase antibody 1E1 was generated by immunizing BALB/c mice with the entire 65 kDa heparanase protein [Shafat I et al., Biochem Biophys Res Commun 2006; 341:958-63]. Polyclonal antibody 1453 was raised in rabbits against the entire 65 kDa heparanase precursor isolated from the conditioned medium of heparanase-transfected HEK-293 cells. The antibody was affinity-purified on immobilized bacterially expressed 50 kDa heparanase GST fusion protein [Zetser A et al., J Cell Sci 2004; 117:2249-58]. Recombinant human factor VIIa and plasma-derived human factor X were purchased from American Diagnostica (Stanford, Conn.). Fondaparinux (Arixtra) was purchased from GlaxoSmithKline (London, UK). All coagulation factors were dissolved in double-distilled water. Chromogenic substrate to factor Xa (I.D. 222, solubility: Tris buffer, pH −8.4) and chromogenic substrate to thrombin (I.D. 238, solubility: Tris buffer, pH −8.4) were purchased from American Diagnostica (Stanford, Conn.).
Heparanase Procoagulant Activity Assay.
A basic experiment of factor Xa generation was performed as follows: the concentrations mentioned are the final concentrations. To 25 µl of plasma and 50 µl assay buffer (0.06 M Tris, 0.04 M NaCl, 2 mM $CaCl_2$, 0.04% BSA, pH 8.4), recombinant human factor VIIa (0.04 µM) and plasma-derived human factor X (1.4 µM) were added to a total volume of 125 µl in a 96-well sterile plate. After 15 minutes at 37° C., chromogenic substrate to factor Xa was added (1 mM). Following 20 minutes, the reaction was stopped with 50 µl of glacial acetic acid and the level of Xa generation was determined using an ELISA plate reader (Power Wave XS, BIO-TEK, VT). In parallel, the same assay was performed except that fondaparinux (2.5 µg/ml) was added to the assay buffer.

The subtraction of the first assay result from the second assay result determined heparanase procoagulant activity.

Heparanase Enzyme-Linked Immunosorbent Assay (ELISA).

Wells of microtiter plates were coated (18 h, 4° C.) with 2 μg/ml of anti-heparanase monoclonal antibody in 50 μl coating buffer (0.05 M $Na_2CO_3$, 0.05 M $NaHCO_3$, pH 9.6) and were then blocked with 2% BSA in PBS for 1 h at 37° C. Samples (200 μl) were loaded in duplicates and incubated for 2 h at room temperature, followed by the addition of 100 μl antibody 1453 (1 μl/ml) for an additional period of 2 h at room temperature. HRP-conjugated goat anti-rabbit IgG (1:20,000) in blocking buffer was added (1 h, room temperature) and the reaction was visualized by the addition of 50 μl chromogenic substrate (TMB; MP Biomedicals, Germany) for 30 minutes. The reaction was stopped with 100 μl $H_2SO_4$ and absorbance at 450 nm was measured using an ELISA plate reader (Power Wave XS, BIO-TEK, VT). Plates were washed five times with washing buffer (PBS, pH 7.4 containing 0.1% (v/v) Tween 20) after each step. As a reference for quantification, a standard curve was established by serial dilutions of recombinant 8+50 GS3 heparanase (390 pg/ml-25 ng/ml) [Shafat I et al., Biochem Biophys Res Commun 2006; 341:958-63].

Factor Xa and Thrombin Chromogenic Assays.

50 μl plasma was added to 50 μl Tris buffer (0.06 M, pH 8.4) and 25 μl of chromogenic substrate to factor Xa (5 mM) or 25 μl of chromogenic substrate to thrombin (5 mM). After 30 minutes the reaction was stopped with glacial acetic and the absorbance at 405 nm-490 nm was measured using an ELISA plate reader (Power Wave XS, BIO-TEK, VT).

Statistical Analysis.

Data were evaluated by SPSS software for Windows version 13.0 (SPSS Inc., Chicago, Ill.). The T-TEST for dependent variables was used. $P<0.05$ was considered statistically significant. Values are reported as mean±SEM Results Characteristics of the 50 patients undergoing hip and knee surgery are presented in table 1. The majority of patients had hip surgery (31/50, 62%), and osteoarthrosis (hip or knee) was the prevalent indication for surgery (35/50, 70%). Half of the hip surgeries were due to trauma (15/31, 48%).

Example C1

Plasma Heparanase Levels and Procoagulant Activity

Heparanase levels were adjusted due to variability in ELISA plate batches (FIG. 14). Samples of each patient were tested in the same plate. The lowest level of the patient samples was referred as 1, and other results of the same patient, were calculated relative to the lowest sample. Levels of heparanase increased after 1 hour, reached maximum after 1 week and remained increased 1 month post operation. Differences in TF/heparanase activity were more significant reaching maximum 0.1 week after surgery, without a significant decline at 1 month. At 1 hour and 1 week post surgery, the major contribution to TF/heparanase activity is heparanase activity, while at 1 month, TF activity is the dominant parameter (FIGS. 15A-15D).

Example C2

Plasma Factor Xa and Thrombin Levels

Levels of factor Xa and thrombin increased at 1 month post surgery, similar to the pattern of TF activity, although statistical significance was reached only in factor Xa levels.

Example C3

Patient Subpopulations Analysis

Evaluation of the 35 patients with osteoarthrosis and 15 patients with trauma regarding all tested coagulation parameters did not revealed significant differences between the groups. In addition, there was also no significant difference comparing the 31 patients with hip surgery to 19 patients with knee surgery (data not shown).

Example C4

Clinical Thrombotic Events

Three thrombotic events occurred. The first was in a 75 old male patient with hypertension, non-insulin dependent diabetes type II and hypercholesterolemia who had an acute myocardial infarction 24 hours post operation. Surgery was due to osteoarthrosis and his weight was 75 kg. As sample was not taken 24 hours after surgery in this study, we cannot exclude a rise in the studied hemostatic parameters at this time point. No significant differences were found between the patient's samples and the means of the study group. The second thrombosis occurred in a 70 years old female patient with hypertension. Surgery was due to osteoarthrosis. Her weight was 66 kg. The postoperative period was uneventful. One month post surgery she was walking using a stick and reported decrease in pain. She stopped enoxaparin injections after five weeks. At the sixth week she was re-hospitalized due to pulmonary emboli (PE). In her coagulation tests, the most dramatic change was the increased heparanase procoagulant activity at 4 weeks post operation (FIG. 17A, sample number 4), reaching 8 fold increase, compared to baseline level (sample number 1) while the mean heparanase procoagulant activity of the study group at 1 month reached only a 2 fold increase compared to baseline level (FIGS. 15A-15D). The third patient was a 76 years old female during chemotherapy treatment due to breast cancer. Additionally she had hypertension and osteoporosis. Surgery was due to traumatic hip fracture and her weight was 62 kg. The postoperative period was uneventful. One month post surgery she was walking without any help or pain. She stopped enoxaparin injections after five weeks. At the sixth week she was re-hospitalized due to proximal DVT in the affected leg. In the coagulation tests, although heparanase procoagulant activity at 1 month was two fold increased compared to baseline, the most striking increase was in TF activity reaching 4 fold increase as well as in factor Xa and thrombin levels, reaching 9 fold increase (FIG. 17B), while in the study group the increase was 1.7 folds (FIGS. 15A-15D and 16A-16B).

Example D

Heparanase Procoagulant Activity in Endometriosis

Background:

The purpose of this study was to determine whether in women with endometriosis an increase of heparanase and heparanase procoagulant activity is noticeable in the blood, when compared with women without endometriosis. A second objective of the study was to determine whether in women with endometriosis, a correlation between the level of heparanase in blood and the clinical status of the patient as determined by anamnesis and clinical examination, exists.
Methods:

Blood samples (about 6 cc) were taken from women over 18 years old showing a positive diagnosis for endometriosis, and transferred into 2 tubes with citrate (PT test tubes). Blood samples from healthy women over 18 years old were used as a control. Pregnant women or women presenting with known active cancer, kidney failure or liver failure were excluded from the study. Additional samples of the same women were taken in three additional visits to the clinic. Blood samples were immediately centrifuged at 1500 g at room temperature for 15 minutes. 250 cc of plasma was transferred in Eppendorf tubes (6-8 tubes were prepared) and placed in deep freeze (−86° C.). Heparanase plasma level was determined by an ELISA test, and heparanase procoagulant activity was determined by using the chromogenic assay of the invention. Activation of the coagulation system was assessed by determining the level of thrombin and factor Xa via a chromogenic assay, and the level of D-dimer was determined by ELISA.

Example E

Involvement of Heparanase in Diabetic Foot

Background:

Heparanase was recently shown to be increased in plasma and urine of NIDDM patients. In addition, a good correlation between serum glucose levels and urinary heparanase [Shafat I. et al., *PLoS One* 2011, 6:e17312]. In immunostaining studies of biopsies from retina in diabetic rats and kidney from diabetic patients heparanase staining was more prominent compared to control biopsies [Ma P. et al. Can J Ophthalmol 2010, 45:46-51; Van den Hoven M J et al., Kidney Int 2006, 70:2100-2108]. Glucose was found to up-regulate heparanase expression in renal tubular cells (HEK 293) and in endothelial cells [Maxhimer J B et al., Diabetes 2005, 54:2172-2178]. Suggested mechanism of heparanase involvement in diabetic pathology include degradation of heparan sulfate chains on glomerular cell surfaces resulting in increased glomerular permeability [Wijnhoven T J et al., *Diabetologia* 2008, 51:372-382]. In order to widen the knowledge of heparanase involvement in diabetic microcirculation complications, the present example has been focused on the role of heparanase in diabetic foot.
Methods:

The study group included patients with diabetic foot coming to the orthopedic surgery word due to inevitable need for amputation. The control group included patients having surgery in the foot due to trauma. 6 ml citrated blood immediately before and following leg amputation (1 hour, 1 week, 2 months following surgery) were drown. Samples were taken at least 23 hours after prophylactic enoxaparin (clexan) treatment. Biopsies from amputations included skin biopsy and bone biopsy from the diabetic wound, in between and from the surgical edge (6 biopsies from each patients). Plasma analysis were performed for heparanase procoagulant activity by chromogenic substrate, heparanase levels by ELISA and heparanase polymorphisms [Ostrovsky O et al., Acta Haematol 2007, 117:57-64; Ostrovsky O et al., Blood 2010, 115:2319-2328; Wang L D et al., Nat Genet. 2010, 42:759-763] by RT-PCR. Biopsies were stained for heparanase, tissue factor, tissue factor pathway inhibitor (TFPI), fibrin, heparan sulfate chains. The study group included 40 patients with diabetic foot and 40 patients with trauma in the foot. No biopsy were taken if it has any potential to complicate the surgery or against the patients optimal care. Inclusion criteria: Age above 18. Exclusion criteria: Active infection in the foot, arterial or venous thrombosis in the amputated leg in the last 6 months.

Example F

Heparanase Procoagulant Activity Assay as a Marker for Thrombotic Potential and Survival in Cancer Patients Background:

Heparanase activity is implicated in tumor growth, neovascularization, inflammation and autoimmunity [Dempsey L A et al., Trends Biochem Sci 2000, 25:349-351; Parish C R et al., Biochim Biophys Acta 2001, 1471:M99-108; Vlodaysky I et al., J Clin Invest 2001, 108:341-347]. A single human heparanase cDNA sequence was independently reported by several groups [Hulett M D et al., Nat Med 1999, 5:803-809; Kussie P H et al., Biochem Biophys Res Commun 1999, 261:183-187; Toyoshima M et al., J Biol Chem 1999, 274: 24153-24160; Vlodaysky I. et al., Nat Med 1999, 5:793-802]. Thus, unlike the large number of proteases that can degrade polypeptides in the extracellular matrix (ECM), one enzyme appears to be used by cells to degrade the HS side chains of HS proteolycans. Applying heparanase that lacks enzymatic activity, it was noted that heparanase exerts also non-enzymatic activities, independent of its involvement in ECM degradation and alterations in the extracellular microenvironment associated with tissue remodeling, angiogenesis, and cell invasion [Goldshmidt O. et al, Faseb J 2003, 17:1015-1025; Gingis-Velitski S et al., J Biol Chem 2004, 279:23536-23541; Zetser A et al., Cancer Res 2006, 66:1455-1463]. The clinical significance of the enzyme in tumor progression emerges from a systematic evaluation of heparanase expression in primary human tumors. Patients with biopsy positive heparanase staining exhibited a significantly higher rate of local and distant metastasis as well as reduced post-operative survival, compared with patients that were diagnosed as heparanase-negative [Tang W et al., Mod Pathol 2002, 15:593-598; Kelly T et al., Cancer Res 2003, 63:8749-8756; Gohji K et al., J Urol 2001, 166:1286-1290; Rohloff J et al., Br J Cancer 2002, 86:1270-1275; Sato T et al.; J Surg Oncol 2004, 87:174-181]. In addition, heparanase up regulation in primary human tumors correlated in some cases with tumors larger in size [Tang W et al., Mod Pathol 2002, 15:593-598; Maxhimer J B et al., Surgery 2002, 132:326-333; El-Assal O N et al., Clin Cancer Res 2001, 7:1299-1305], and with enhanced micro vessel density [Kelly T. et al, Cancer Res 2003, 63:8749-8756; 15; Sato T et al., J Surg Oncol 2004, 87:174-181; El-Assal O N et al., Clin Cancer Res 2001, 7:1299-1305; Gohji K et al., Int J Cancer 2001, 95:295-301], providing a clinical support for the pro-angiogenic function of the enzyme. In the present example, the heparanase procoagulant activity assay of the invention has been tested in patients with solid malignancies. Results have been correlated to heparanase level by ELISA and heparanase polymorphisms.
End Points:

The primary end point was to demonstrate a significant difference in heparanase procoagulant activity in patients with active malignancy compared to non-malignant control cases. Secondary end points included: 1. correlating heparanase levels and polymorphisms to heparanase procoagulant activity. 2. Correlating clinical thromboembolic events and survival to heparanase procoagulant activity.

Methods:

A prospective controlled study. The study has been approved by the institutional Ethic Committee on human research at the Rambam Medical Center. The study group included solid cancer patients before starting chemotherapy or radiotherapy. The control group included volunteers without known active malignancy and with comparable demographic characteristics. 10 ml blood were drawn, 6 ml with citrate 3.2% (1:9) and 3 ml with EDTA. Analysis were performed for heparanase procoagulant activity, heparanase levels by ELISA and heparanase polymorphisms [Ostrovsky O et al., Acta Haematol 2007, 117:57-64; Ostrovsky O et al., Blood 2010, 115:2319-2328; Wang L D et al. Nat Genet. 2010, 42:759-763] by RT-PCR. Women still having the period have been tested for βHCG level by urine analysis to exclude pregnancy at the time of blood sampling. Patients have been followed-up using the charts for thromboembolic events and survival for 2 years. Inclusion criteria: Patients diagnosed with malignancy and before starting chemotherapy or radiotherapy. At least 2 months post surgery. Exclusion criteria: Non-ambulatory with performance status WHO 4, Anticoagulant (anti-platelets therapy is allowed) or hormone therapy, evidence of active infection, elevated serum bilirubin, serum transaminases >2 upper limit and creatinine >1.5 mg/dl. Sample size: it was shown by the inventors that in pregnant women or on oral contraceptives heparanase procoagulant activity was 3-4 fold increased compared to controls with a statistically significant difference. Groups in these studies included about 40 cases and 40 controls.

Example G

Heparanase Procoagulant Activity Assay as a Thrombophilic Marker in Pregnancy Vascular Complications Background:

Heparanase is an endo-β-d-glucuronidase capable of cleaving heparan sulfate (HS) side chains at a limited number of sites, yielding HS fragments of still appreciable size (~5-7 kDa) [Freeman C et al., Biochem J 1998, 330 (Pt 3):1341-1350; Pikas D S et al., J Biol Chem 1998, 273:18770-18777]. Heparanase activity was correlated with metastatic potential of tumor-derived cells, attributed to enhanced cell dissemination as a consequence of HS cleavage and remodeling of the extracellular matrix (ECM) barrier [Parish C R et al., Biochim Biophys Acta 2001, 1471:M99-108; Vlodaysky I et al., J Clin Invest 2001, 108:341-347]. Similarly, heparanase activity was implicated in neovascularization, inflammation and autoimmunity, involving migration of vascular endothelial cells and activated cells of the immune system [Parish C R et al., Biochim Biophys Acta 2001, 1471:M99-108; Vlodaysky I et al., J Clin Invest 2001, 108:341-347; Dempsey L A et al., Trends Biochem Sci 2000, 25:349-351]. Recently, the inventors have demonstrated that heparanase may also affect the hemostatic system in a non-enzymatic manner. Heparanase was shown to up-regulate tissue factor (TF) expression [Nadir Y. et al., J Thromb Haemost 2006, 4:2443-2451] and interact with tissue factor pathway inhibitor (TFPI) on cell surface, leading to dissociation of TFPI from cell membrane of endothelial and tumor cells, resulting in increased cell surface coagulation activity [Nadir Y. et al., Thromb Haemost 2008, 99:133-141]. More recently, heparanase was shown to directly enhance TF/factor VIIa activity resulting in increased factor Xa production. This effect was demonstrated with purified proteins and normal human plasma using chromogenic substrate, western blot and thromboelastography assays [Nadir Y. et al., Haematologica 2010]. The heparanase procoagulant activity assay of the present invention is based on the presence of TF/heparanase complex and the ability of an inhibitor to completely abrogate the complex interaction.

End Points:

The primary end point was to demonstrate increased heparanase procoagulant activity and heparanase levels in women with pregnancy vascular complications compared to women with normal obstetric history. Secondary end points included finding heparanase polymorphisms that correlate with pregnancy vascular complications and heparanase procoagulant activity.

Methods:

A prospective controlled study. The study group included patients coming to the Thrombosis and Hemostasis clinic with a history of pregnancy vascular complications requiring thrombophilia work-up. The routine thrombophilia work-up has been down by health care serves. The control group included healthy non-pregnant volunteers with comparable demographic characteristics. 10 ml blood has been drawn, 6 ml with citrate 3.2% (1:9) and 3 ml with EDTA. Analysis have been performed for heparanase procoagulant activity, heparanase levels by ELISA and recently found heparanase polymorphisms [Ostrovsky O et al., Acta Haematol 2007, 117:57-64; Ostrovsky O et al., Blood 2010, 115:2319-2328; Wang L D et al. Nat Genet. 2010, 42:759-763] by RT-PCR. All women have been tested for βHCG level by urine analysis to exclude pregnancy at the time of blood sampling. Inclusion criteria: Non-pregnant women. History of pregnancy vascular complications including at least one of the followings: 3 consecutive early pregnancy losses, 2 pregnancy losses in the second trimester and one intra-uterine death (IUFD), placental abruption, intra-uterine growth restriction below 10 percentile, pre-term delivery (before 36 weeks), eclampsia and pre-eclampsia starting before 32 weeks. Inclusion criteria of control group: healthy non-pregnant volunteers with previous at least 2 normal pregnancies. Exclusion criteria: Signs and/or symptoms of infection in the mothers or the fetus during pregnancy, macroscopic morphologic abnormality in the fetus according to routine US follow-up or post-delivery, medications use (including any hormonal therapy) other than supplement vitamins and minerals. Known abnormal liver or kidney laboratory tests. Exclusion criteria for the control group: medications use (including any hormonal therapy) other than supplement vitamins and minerals. Known abnormal liver or kidney laboratory tests. Sample size: an increased heparanase procoagulant activity has been found in women taking oral contraceptives and women at the end of pregnancy compared to women not on oral contraceptive and not pregnant. The present study was the first attempt to demonstrate increased heparanase procoagulant activity as a thrombophilia marker. The prevalence of known thrombophilias in the general population is 1-10% while in women with pregnancy complications 40-60% (~4-5 fold increase).

Example H

Heparanase Procoagulant Activity is Elevated in Women Taking Oral Contraceptives Background:

Estrogen therapy increasing the risk of thrombosis was found to up-regulate heparanase expression. Heparanase, known to be involved in angiogenesis and metastasis, has been now found to directly interact with tissue factor (TF) and to enhance the generation of factor Xa. The present invention discloses an assay evaluating heparanase procoagulant. In the present study heparanase level and procoagulant activity in women taking oral contraceptives (OC) were assessed.

Methods:

Plasma samples of 34 healthy women taking OC and 41 control women not on hormonal therapy were investigated. TF/heparanase complex activity, TF activity, heparanase procoagulant activity and factor Xa levels were studied using chromogenic substrate. Heparanase and thrombin-antithrombin (TAT) levels were analyzed by ELISA.

Results:

TF/heparanase activity, TF activity, heparanase procoagulant activity and factor Xa were significantly higher in the OC group compared to the control group. The most dramatic difference was observed in heparanase procoagulant activity, reaching a 3.3 fold increase ($p<0.0001$) and a 24% elevation in heparanase contribution to TF/heparanase complex. Levels of heparanase and TAT measured by ELISA did not statistically differ among the study groups.

Conclusions:

OC activate the extrinsic coagulation pathway and the most dominant change occurs in heparanase procoagulant activity. The findings of the present study suggest a new potential mechanism of hypercoagulability in OC users.

Example I

Heparanase Activation of the Coagulation System In a Mice Sepsis Model and Implication of TF/Heparanase Inhibitory Peptides Background:

Heparanase that is abundant in platelets and neutrophils is implicated in cell invasion, tumor metastasis and angiogenesis. The inventors have demonstrated that heparanase is directly involved in the regulation of the hemostatic system. Heparanase was shown to form a complex and enhance tissue factor (TF) activity, resulting in increased factor Xa production. In the present example the effect of heparanase in sepsis was studied.

Methods:

ICR mice, heparanase knock-out mice and heparanase over-expression mice were studied. Sepsis was induced by intra-peritoneal injection of lipopolysaccharides (LPS). Inhibitory peptides to TF/heparanase complex (number 11, 22, 5, 6, 7, 12, and 21 [SEQ IDs: 1-7]) were injected intra-peritoneal half an hour after heparanase or LPS. After 4 hours blood was obtained via sub-mandibular plexus puncture followed by mice sacrificing. Levels of thrombin-antithrombin (TAT), D-Dimer and IL-6 were tested using ELISA. Western blot to plasma factor VII and immunostaining of fibrinogen in lung, kidney and spleen were performed.

Results:

Intra-peritoneal injection of heparanase (0.5 µg/mg) compared to PBS injection increased TAT ($p<0.05$) and D-Dimer ($p<0.05$) levels to similar levels induced by LPS (5 µg/mg), although levels of IL-6 did not rise and mice did not show signs of illness. Injection of heparanase half an hour following LPS resulted in reduced levels of TAT, D-Dimer, fibrinogen by immunostaining and factor VII by western blot ($p<0.001$), maximal levels of IL-1 ($p<0.001$) and profuse blood leak from puncture, compatible with severe disseminated intravascular coagulation (DIC). In accordance, injection of LPS to heparanase knock-out mice resulted in reduced levels of TAT ($p<0.001$), D-Dimer ($p<0.001$) and IL-6 ($p<0.001$) compared to control mice, while injection of LPS to heparanase over-expression mice resulted in DIC. TF/heparanase inhibitory peptides abolished the procoagulant effect of heparanase and markedly attenuated the coagulation and inflammation in sepsis.

Conclusions:

Heparanase induce activation of the coagulation system without inflammatory response. Heparanase contributes to laboratory enhancement of sepsis resulting in DIC. Inhibitors of heparanase may potentially attenuate morbidity and mortality in sepsis.

The invention claimed is:

1. A method of treating at least one condition associated with increased coagulation activity in a subject in need thereof, the method comprising the steps of:

determining increased heparanase procoagulant activity in the subject, comprising (a) providing a biological sample from the subject;

(b) contacting aliquots of said biological sample with a first test solution (TS1) comprising a buffer solution, factor VIIa, and factor X and with a second test solution (TS2) comprising a buffer solution, factor VIIa, factor X, and an inhibitor capable of disrupting the Heparanase/Tissue Factor complex;

(c) adding to TS1 and to TS2 a substrate to factor Xa suitable to produce an optically detectable product;

(d) measuring the level of said optically detectable product in TS1 (L1);

(e) measuring the level of said optically detectable product in TS2 (L2);

(f) obtaining heparanase procoagulant activity (HPA) by subtracting L2 from L1, and obtaining heparanase relative contribution to the coagulation system by dividing HPA by L1;

(g) comparing said value of heparanase procoagulant activity to a predetermined control value or to a value of heparanase procoagulant activity of a control sample, wherein an elevated level of heparanase procoagulant activity in said biological sample as compared to said control sample or said predetermined control value is indicative that said subject is having a coagulation-related pathologic disorder associated with increased coagulation activity, overactive coagulation activity, or thrombophilia; and wherein reduced level of heparanase procoagulant activity in said biological sample as compared to said control sample or said predetermined control value is indicative that said subject is having a coagulation-related pathologic disorder associated with impaired, reduced or deficient coagulation activity; and administering to the subject a pharmaceutical composition comprising an inhibitor selected from the group consisting of anti-Xa derivatives, unfractionated heparin, low molecular weight heparins, fondaparinux, rivaroxaban, enoxaparin, tissue factor pathway inhibitor 1 and derivatives thereof, a tissue factor pathway inhibitor 2 and derivatives thereof, a peptide of SEQ ID: 1, a peptide of SEQ ID: 2, a peptide of SEQ ID: 3, a peptide of SEQ ID: 4, a peptide of SEQ ID: 5, a peptide of SEQ ID: 6, and a peptide of SEQ ID: 7, wherein said subject is suffering from a pathologic condition associated with increased coagulation activity, selected from the group consisting of a pathologic condition associated with contraceptive treatments, proliferative disorders, inflammatory diseases, orthopedic surgery, diabetic foot, endometriosis, pregnancy vascular complications, cardiovascular complications, hyperplasia, and avascular necrosis of hip.

2. The method of claim 1, wherein the biological sample, factor VIIa and factor X are of the same mammalian species.

3. The method of claim 1, wherein one or more of factor VIIa and factor X is a recombinant protein.

4. The method of claim 1, wherein one or more of factor VIIa and factor X is a natural plasma-derived protein.

5. The method of claim 1, wherein the inhibitor is selected from the group consisting of anti-Xa derivatives, unfractionated heparin, low molecular weight heparins, fondaparinux, rivaroxaban, enoxaparin, tissue factor pathway inhibitor 1 and derivatives thereof, and tissue factor pathway inhibitor 2 and derivatives thereof.

6. The method of claim 1, wherein the inhibitor is a peptide having an amino acid sequence selected from the group consisting of SEQ ID: 1, SEQ ID: 2, SEQ ID: 3, SEQ ID: 4, SEQ ID: 5, SEQ ID: 6, SEQ ID: 7, and derivatives thereof.

7. The method of claim 1, wherein treating comprises treating, ameliorating or preventing increased coagulation activity.

8. The method of claim 1, wherein said subject is human.

9. The method of claim 1, wherein the step of administering involves injecting pharmaceutical composition comprising the inhibitor into the subject in need thereof.

10. A method of treating at least one condition associated with increased coagulation activity in a subject in need thereof, the method comprising the steps of:

determining increased heparanase procoagulant activity in the subject, comprising
(a) providing a biological sample of a mammalian subject;
(b) contacting aliquots of said biological sample with a first test solution (TS1) comprising a buffer solution, factor VIIa, and factor X and with a second test solution (TS2) comprising a buffer solution, factor VIIa, factor X, and an inhibitor capable of disrupting the Heparanase/Tissue Factor complex;
(c) adding to TS1 and to TS2 a substrate to factor Xa suitable to produce an optically detectable product;
(d) measuring the level of said optically detectable product in TS1 (L1);
(e) measuring the level of said optically detectable product in TS2 (L2); and
(f) determining an elevated level of heparanase procoagulant activity in said biological sample as compared to a predetermined control value or to a value of heparanase procoagulant activity of a control sample, thereby determining that said subject is having a coagulation-related pathologic disorder associated with increased coagulation activity, overactive coagulation activity, or thrombophilia; and
(g) administering to the subject a pharmaceutical composition comprising an inhibitor selected from the group consisting of anti-Xa derivatives, unfractionated heparin, low molecular weight heparins, fondaparinux, rivaroxaban, enoxaparin, tissue factor pathway inhibitor 1 and derivatives thereof, a tissue factor pathway inhibitor 2 and derivatives thereof, a peptide of SEQ ID: 6, wherein heparanase procoagulant activity (HPA) is obtained by subtracting L2 from L1, and heparanase relative contribution to the coagulation system is obtained by dividing HPA by L1.

* * * * *

SEQUENCE LISTING

<160> NUMBER OF SEQ ID NOS: 7

<210> SEQ ID NO 1
<211> LENGTH: 14
<212> TYPE: PRT
<213> ORGANISM: Artificial sequence
<220> FEATURE:
<223> OTHER INFORMATION: Peptide

<400> SEQUENCE: 1

Leu Leu Arg Tyr Tyr Tyr Asp Arg Tyr Thr Gln Ser Cys Arg
1               5                   10

<210> SEQ ID NO 2
<211> LENGTH: 14
<212> TYPE: PRT
<213> ORGANISM: Artificial sequence
<220> FEATURE:
<223> OTHER INFORMATION: Peptide

<400> SEQUENCE: 2

Asn Asn Phe Tyr Thr Trp Glu Ala Cys Asp Asp Ala Cys Trp
1               5                   10

```
<210> SEQ ID NO 3
<211> LENGTH: 14
<212> TYPE: PRT
<213> ORGANISM: Artificial sequence
<220> FEATURE:
<223> OTHER INFORMATION: Peptide

<400> SEQUENCE: 3

Ile Cys Leu Leu Pro Leu Asp Tyr Gly Pro Cys Arg Ala Leu
1               5                   10

<210> SEQ ID NO 4
<211> LENGTH: 14
<212> TYPE: PRT
<213> ORGANISM: Artificial sequence
<220> FEATURE:
<223> OTHER INFORMATION: Peptide

<400> SEQUENCE: 4

Ala Glu Ile Cys Leu Leu Pro Leu Asp Tyr Gly Pro Cys Arg
1               5                   10

<210> SEQ ID NO 5
<211> LENGTH: 14
<212> TYPE: PRT
<213> ORGANISM: Artificial sequence
<220> FEATURE:
<223> OTHER INFORMATION: Peptide

<400> SEQUENCE: 5

Asn Asn Ala Glu Ile Cys Leu Leu Pro Leu Asp Tyr Gly Pro
1               5                   10

<210> SEQ ID NO 6
<211> LENGTH: 14
<212> TYPE: PRT
<213> ORGANISM: Artificial sequence
<220> FEATURE:
<223> OTHER INFORMATION: Peptide

<400> SEQUENCE: 6

Arg Tyr Tyr Tyr Asp Arg Tyr Thr Gln Ser Cys Arg Gln Phe
1               5                   10

<210> SEQ ID NO 7
<211> LENGTH: 11
<212> TYPE: PRT
<213> ORGANISM: Artificial sequence
<220> FEATURE:
<223> OTHER INFORMATION: Peptide

<400> SEQUENCE: 7

Asn Ala Asn Asn Phe Tyr Thr Trp Glu Ala Cys
1               5                   10
```